United States Patent
Anderson et al.

(10) Patent No.: US 10,253,054 B2
(45) Date of Patent: *Apr. 9, 2019

(54) PRODRUGS OF PYRIDONE AMIDES USEFUL AS MODULATORS OF SODIUM CHANNELS

(71) Applicant: VERTEX PHARMACEUTICALS INCORPORATED, Boston, MA (US)

(72) Inventors: Corey Anderson, San Diego, CA (US); Sara Sabina Hadida-Ruah, LaJolla, CA (US); Julian Marian Charles Golec, Abingdon (GB); Beili Zhang, San Diego, CA (US); Benjamin Joseph Littler, Carlsbad, CA (US); Ali Keshavarz-Shokri, San Diego, CA (US); Tim Edward Alcacio, San Diego, CA (US); Daniel T. Belmont, Grafton, MA (US)

(73) Assignee: VERTEX PHARMACEUTICALS INCORPORATED, Boston, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/791,982

(22) Filed: Oct. 24, 2017

(65) Prior Publication Data

US 2018/0044361 A1 Feb. 15, 2018

Related U.S. Application Data

(63) Continuation of application No. 15/260,778, filed on Sep. 9, 2016, now Pat. No. 9,828,397, which is a continuation of application No. 14/858,635, filed on Sep. 18, 2015, now Pat. No. 9,464,102, which is a continuation of application No. 14/568,391, filed on Dec. 12, 2014, now Pat. No. 9,163,042.

(60) Provisional application No. 61/915,937, filed on Dec. 13, 2013.

(51) Int. Cl.
| | |
|---|---|
| *C07F 9/58* | (2006.01) |
| *C07F 9/59* | (2006.01) |
| *A61K 31/675* | (2006.01) |
| *A61K 45/06* | (2006.01) |
| *C07F 9/576* | (2006.01) |
| *C07D 211/80* | (2006.01) |

(52) U.S. Cl.
CPC .............. *C07F 9/58* (2013.01); *A61K 31/675* (2013.01); *A61K 45/06* (2013.01); *C07F 9/576* (2013.01); *C07F 9/59* (2013.01)

(58) Field of Classification Search
None
See application file for complete search history.

(56) References Cited

U.S. PATENT DOCUMENTS

| | | | |
|---|---|---|---|
| 5,304,121 A | 4/1994 | Sahatjian | |
| 5,886,026 A | 3/1999 | Hunter et al. | |
| 6,099,562 A | 8/2000 | Ding et al. | |
| 8,389,734 B2 | 3/2013 | Chen | |
| 8,466,188 B2 | 6/2013 | Chafeev et al. | |
| 8,486,950 B2 | 7/2013 | Goodacre et al. | |
| 8,519,137 B2 | 8/2013 | Joshi | |
| 8,779,197 B2 | 7/2014 | Chen | |
| 8,841,483 B2 | 9/2014 | Joshi | |
| 8,865,771 B2 | 10/2014 | Chen | |
| 8,883,840 B2 | 11/2014 | Chafeev et al. | |
| 9,051,270 B2 | 6/2015 | Hadida Ruah | |
| 9,108,903 B2 | 8/2015 | Hadida Ruah | |
| 9,139,529 B2 | 9/2015 | Hadida Ruah | |
| 9,163,008 B2 | 10/2015 | Ni et al. | |
| 9,163,042 B2 | 10/2015 | Anderson | |
| 9,393,235 B2 | 7/2016 | Hadida Ruah | |
| 9,421,196 B2 | 8/2016 | Hadida Ruah | |
| 9,464,102 B2 | 10/2016 | Anderson | |
| 9,656,959 B2 | 5/2017 | Ni et al. | |
| 9,758,483 B2 | 9/2017 | Hadida Ruah | |
| 9,783,501 B2 | 10/2017 | Hadida Ruah | |

(Continued)

FOREIGN PATENT DOCUMENTS

| | | |
|---|---|---|
| CN | 101855210 | 10/2010 |
| CN | 101883758 | 11/2010 |

(Continued)

OTHER PUBLICATIONS

Akopian, A.N., L. Sivilotti, and J.N. Wood, A tetrodotoxin-resistant voltage-gated sodium channel expressed by sensory neurons. *Nature*, 1996. 379(6562): p. 257-62.

(Continued)

*Primary Examiner* — Zinna Northington Davis
(74) *Attorney, Agent, or Firm* — Brinks Gilson & Lione

(57) ABSTRACT

The invention relates to prodrug compounds of formula I:

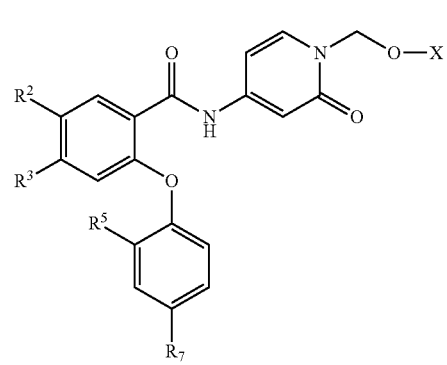

wherein $R^2$, $R^3$, $R^5$, $R^7$ and X are as defined herein. The invention also provides pharmaceutically acceptable compositions comprising the compounds of the invention and methods of using the compositions in the treatment of various disorders, including pain. The compounds of formula I possess advantageous solubility and physicochemical properties.

38 Claims, 4 Drawing Sheets

(56) References Cited

U.S. PATENT DOCUMENTS

| | | |
|---|---|---|
| 9,828,397 B2 | 11/2017 | Anderson |
| 10,087,143 B2 | 10/2018 | Hadida-Ruah et al. |
| 2007/0238733 A1 | 10/2007 | Joshi |
| 2009/0099233 A1 | 4/2009 | Joshi |
| 2009/0118333 A1 | 5/2009 | Chen |
| 2009/0118338 A1 | 5/2009 | Chen |
| 2010/0105906 A1 | 4/2010 | Bissantz et al. |
| 2013/0231370 A1 | 9/2013 | Chen |
| 2013/0303535 A1 | 11/2013 | Tsuboi et al. |
| 2014/0213616 A1 | 7/2014 | Hadida Ruah |
| 2014/0221435 A1 | 8/2014 | Hadida Ruah |
| 2014/0228371 A1 | 8/2014 | Hadida Ruah |
| 2015/0166589 A1 | 6/2015 | Anderson |
| 2015/0246028 A1 | 9/2015 | Hadida Ruah |
| 2015/0328196 A1 | 11/2015 | Hadida Ruah |
| 2015/0336945 A1 | 11/2015 | Hadida Ruah |
| 2015/0376174 A1 | 12/2015 | Kawana et al. |
| 2016/0009743 A1 | 1/2016 | Anderson |
| 2016/0152561 A1 | 6/2016 | Hadida Ruah |
| 2016/0376295 A1 | 12/2016 | Anderson |
| 2017/0037009 A1 | 2/2017 | Hadida Ruah |
| 2018/0016235 A1 | 1/2018 | Hadida Ruah |
| 2018/0044361 A1 | 2/2018 | Anderson |

FOREIGN PATENT DOCUMENTS

| | | |
|---|---|---|
| CN | 102264722 | 11/2011 |
| CN | 103429571 | 12/2013 |
| JP | 2003/034671 | 2/2003 |
| JP | 2005-531501 | 10/2005 |
| JP | 2011-500599 | 1/2011 |
| JP | 2011-500600 | 1/2011 |
| JP | 2012506887 | 3/2012 |
| JP | 2016506963 | 3/2016 |
| JP | 2016508500 | 3/2016 |
| JP | 2016525122 | 8/2016 |
| RU | 2010/118467 | 11/2011 |
| RU | 2010/118481 | 11/2011 |
| TW | 201331186 | 8/2013 |
| WO | WO2002/008748 | 1/2002 |
| WO | WO 2003/068230 | 8/2003 |
| WO | WO 2005/013914 | 2/2005 |
| WO | WO2006/011050 | 2/2006 |
| WO | WO 2007/120647 | 10/2007 |
| WO | WO2008/135826 | 11/2008 |
| WO | WO2009/049181 | 4/2009 |
| WO | WO2009/049183 | 4/2009 |
| WO | WO 2010/072607 | 7/2010 |
| WO | WO 2010/137351 | 12/2010 |
| WO | WO2011/026240 | 3/2011 |
| WO | WO2011/140425 | 11/2011 |
| WO | WO2012/106499 | 8/2012 |
| WO | WO2012/112743 | 8/2012 |
| WO | WO2012/116440 | 9/2012 |
| WO | WO2012/125613 | 9/2012 |
| WO | WO2013/061205 | 5/2013 |
| WO | WO2013/109521 | 7/2013 |
| WO | WO2013/114250 | 8/2013 |
| WO | WO2013/131018 | 9/2013 |
| WO | WO 2013/132376 A1 | 9/2013 |
| WO | WO2014/120808 | 8/2014 |
| WO | WO2014/120815 | 8/2014 |
| WO | WO2014/120820 | 8/2014 |
| WO | WO 2015/010065 | 1/2015 |

OTHER PUBLICATIONS

Black, J.A., et al., Multiple sodium channel isoforms and mitogen-activated protein kinases are present in painful human neuromas. *Ann Neurol*, 2008. 64(6): p. 644-53.
Blair, N.T. and B.P. Bean, Roles of tetrodotoxin (TTX)-sensitive $Na^+$ current, TTX-resistant $Na^+$ current, and $Ca^{2+}$ current in the action potentials of nociceptive sensory neurons. *J Neurosci.*, 2002. 22(23): p. 10277-90.
CAS Registry No. 1119379-37-1 (Mar. 12, 2009).
CAS Registry No. 1223014-19-4 (May 13, 2010).
CAS Registry No. 1241310-16-6 (Sep. 15, 2010).
CAS Registry No. 1252156-94-7 (Nov. 9, 2010).
CAS Registry No. 1258714-13-4 (Jan. 7, 2011).
CAS Registry No. 1258742-89-0 (Jan. 7, 2011).
CAS Registry No. 1281024-95-0 (Apr. 17, 2011).
CAS Registry No. 1281059-52-6 (Apr. 17, 2011).
CAS Registry No. 1281112-60-4 (Apr. 17, 2011).
CAS Registry No. 1287712-50-8 (Apr. 29, 2011).
CAS Registry No. 1301902-75-9 (May 29, 2011).
CAS Registry No. 1311734-41-4 (Jul. 7, 2011).
CAS Registry No. 1394673-41-6 (Sep. 18, 2012).
CAS Registry No. 1394698-15-7 (Sep. 18, 2012).
Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005).
Chahine, M., Chatelier, A., Babich, O., and Krupp, J. J., Voltage-gated sodium channels in neurological disorders. *CNS Neurol Disord Drug Targets* 7 (2), p. 144-58 (2008).
Choi, J.S. and S.G. Waxman, Physiological interactions between $Na_v1.7$ and $Na_v1.8$ sodium channels: a computer simulation study. *J Neurophysiol.* 106(6): p. 3173-84, (2011).
Coward, K., et al., Immunolocalization of SNS/PN3 and NaN/SNS2 sodium channels in human pain states. *Pain*, 2000. 85(1-2): p. 41-50.
Dieleman, J.P., et al., Incidence rates and treatment of neuropathic pain conditions in the general population. *Pain*, 2008. 137(3): p. 681-8.
Dong, X.W., et al., Small interfering RNA-mediated selective knockdown of $Na_{(v)}1.8$ tetrodotoxin-resistant sodium channel reverses mechanical allodynia in neuropathic rats. *Neuroscience*, 2007. 146(2): p. 812-21.
England, S., Voltage-gated sodium channels: the search for subtype-selective analgesics. *Expert Opin Investig Drugs* 17 (12), p. 1849-64 (2008).
Huang, H.L., et al., Proteomic profiling of neuromas reveals alterations in protein composition and local protein synthesis in hyper-excitable nerves. *Mol Pain*, 2008. 4: p. 33.
International Search Report and Written Opinion of the International Searching Authority for International Application No. PCT/US2014/069916 (dated Feb. 12, 2015).
International Search Report and Written Opinion of the International Searching Authority for International Application No. PCT/US2014/013652 (dated Apr. 2, 2014).
Jarvis, M.F., et al., A-803467, a potent and selective $Na_v1.8$ sodium channel blocker, attenuates neuropathic and inflammatory pain in the rat. *Proc Natl Acad Sci. U S A*, 2007. 104(20): p. 8520-5.
Joshi, S.K., et al., Involvement of the TTX-resistant sodium channel Nav1.8 in inflammatory and neuropathic, but not post-operative, pain states. *Pain*, 2006. 123(1-2): pp. 75-82.
Krafte, D. S. and Bannon, A. W., Sodium channels and nociception: recent concepts and therapeutic opportunities. *Curr Opin Pharmacol* 8 (1), p. 50-56 (2008).
Lai, J., et al., Inhibition of neuropathic pain by decreased expression of the tetrodotoxin-resistant sodium channel, $Na_v1.8$. *Pain*, 2002. 95(1-2): p. 143-52.
Qiu, F., et al., Increased expression of tetrodotoxin-resistant sodium channels $Na_v1.8$ and $Na_v1.9$ within dorsal root ganglia in a rat model of bone cancer pain. *Neurosci. Lett.* 512(2): p. 61-6), (2012).
Renganathan, M., T.R. Cummins, and S.G. Waxman, Contribution of $Na_{(v)}1.8$ sodium channels to action potential electrogenesis in DRG neurons. *J Neurophysiol.*, 2001. 86(2): p. 629-40.
Roza, C., et al., The tetrodotoxin-resistant $Na^+$ channel $Na_v1.8$ is essential for the expression of spontaneous activity in damaged sensory axons of mice. *J. Physiol.*, 2003. 550(Pt 3): p. 921-6.
Ruangsri, S., et al., Relationship of axonal voltage-gated sodium channel 1.8 ($Na_v1.8$) mRNA accumulation to sciatic nerve injury-induced painful neuropathy in rats. *J Biol Chem.* 286(46): p. 39836-47, (2011).

(56) References Cited

OTHER PUBLICATIONS

Rush, A.M. and T.R. Cummins, *Painful Research: Identification of a Small-Molecule Inhibitor that Selectively Targets $Na_v1.8$ Sodium Channels*. Mol Interv, 2007. 7(4): p. 192-5).

Rush, A.M., et al., A single sodium channel mutation produces hyper- or hypoexcitability in different types of neurons. *Proc Natl Acad Sci USA*, 2006. 103(21): p. 8245-50.

Soderpalm, B., Anticonvulsants: aspects of their mechanisms of action. *Eur J Pain* 6 Suppl A, p. 3-9 (2002).

Strickland, I.T., et al., Changes in the expression of NaV1.7, $Na_v1.8$ and $Na_v1.9$ in a distinct population of dorsal root ganglia innervating the rat knee joint in a model of chronic inflammatory joint pain. *Eur J Pain*, 2008. 12(5): p. 564-72.

Sun, W., et al., Reduced conduction failure of the main axon of polymodal nociceptive C-fibres contributes to painful diabetic neuropathy in rats. *Brain*. 135(Pt 2): p. 359-75, (2011).

Wang, G. K., Mitchell, J., and Wang, S. Y., Block of persistent late $Na^+$ currents by antidepressant sertraline and paroxetine. *J Membr Biol* 222 (2), p. 79-90 (2008).

Yiangou, Y., et al., SNS/PN3 and SNS2/NaN sodium channel-like immunoreactivity in human adult and neonate injured sensory nerves. *FEBS Lett*, 2000. 467(2-3): p. 249-52.

PRODRUGS OF PYRIDONE AMIDES USEFUL AS MODULATORS OF SODIUM CHANNELS

CROSS REFERENCE TO RELATED APPLICATIONS

This application is a continuation of U.S. patent application Ser. No. 15/260,778, filed Sep. 9, 2016, which is a continuation of U.S. patent application Ser. No. 14/858,635, filed Sep. 18, 2015, which is a continuation of U.S. patent application Ser. No. 14/568,391, filed Dec. 12, 2014, which claims the benefit of U.S. Provisional Patent Application No. 61/915,937 filed Dec. 13, 2013, all of which are incorporated by reference in their entirety.

BACKGROUND OF THE APPLICATION

Pain is a protective mechanism that allows healthy animals to avoid tissue damage and to prevent further damage to injured tissue. Nonetheless there are many conditions where pain persists beyond its usefulness, or where patients would benefit from inhibition of pain. Neuropathic pain is a form of chronic pain caused by an injury to the sensory nerves (Dieleman, J. P., et al., Incidence rates and treatment of neuropathic pain conditions in the general population. *Pain*, 2008. 137(3): p. 681-8). Neuropathic pain can be divided into two categories, pain caused by generalized metabolic damage to the nerve and pain caused by a discrete nerve injury. The metabolic neuropathies include post herpetic neuropathy, diabetic neuropathy, and drug-induced neuropathy. Discrete nerve injuries indications include post amputation pain, post-surgical nerve injury pain, and nerve entrapment injuries like neuropathic back pain.

Voltage-gated sodium channels ($Na_V$'s) play a critical role in pain signaling. $Na_V$'s are key biological mediators of electrical signaling as they are the primary mediators of the rapid upstroke of the action potential of many excitable cell types (e.g. neurons, skeletal myocytes, cardiac myocytes). The evidence for the role of these channels in normal physiology, the pathological states arising from mutations in sodium channel genes, preclinical work in animal models, and the clinical pharmacology of known sodium channel modulating agents all point to the central role of $Na_V$'s in pain sensation (Rush, A. M. and T. R. Cummins, *Painful Research: Identification of a Small-Molecule Inhibitor that Selectively Targets $Na_V1.8$ Sodium Channels*. Mol Interv, 2007. 7(4): p. 192-5); England, S., Voltage-gated sodium channels: the search for subtype-selective analgesics. *Expert Opin Investig Drugs* 17 (12), p. 1849-64 (2008); Krafte, D. S. and Bannon, A. W., Sodium channels and nociception: recent concepts and therapeutic opportunities. *Curr Opin Pharmacol* 8 (1), p. 50-56 (2008)). $Na_V$'s are the primary mediators of the rapid upstroke of the action potential of many excitable cell types (e.g. neurons, skeletal myocytes, cardiac myocytes), and thus are critical for the initiation of signaling in those cells (Hille, Bertil, *Ion Channels of Excitable Membranes*, Third ed. (Sinauer Associates, Inc., Sunderland, Mass., 2001)). Because of the role $Na_V$'s play in the initiation and propagation of neuronal signals, antagonists that reduce $Na_V$ currents can prevent or reduce neural signaling and $Na_V$ channels have long been considered likely targets to reduce pain in conditions where hyper-excitability is observed (Chahine, M., Chatelier, A., Babich, O., and Krupp, J. J., Voltage-gated sodium channels in neurological disorders. *CNS Neurol Disord Drug Targets* 7 (2), p. 144-58 (2008)). Several clinically useful analgesics have been identified as inhibitors of $Na_V$ channels. The local anesthetic drugs such as lidocaine block pain by inhibiting $Na_V$ channels, and other compounds, such as carbamazepine, lamotrigine, and tricyclic antidepressants that have proven effective at reducing pain have also been suggested to act by sodium channel inhibition (Soderpalm, B., Anticonvulsants: aspects of their mechanisms of action. *Eur J Pain* 6 Suppl A, p. 3-9 (2002); Wang, G. K., Mitchell, J., and Wang, S. Y., Block of persistent late $Na^+$ currents by antidepressant sertraline and paroxetine. *J Membr Biol* 222 (2), p. 79-90 (2008)).

The $Na_V$'s form a subfamily of the voltage-gated ion channel super-family and comprises 9 isoforms, designated $Na_V1.1$-$Na_V1.9$. The tissue localizations of the nine isoforms vary greatly. $Na_V1.4$ is the primary sodium channel of skeletal muscle, and $Na_V1.5$ is primary sodium channel of cardiac myocytes. $Na_V$'s 1.7, 1.8 and 1.9 are primarily localized to the peripheral nervous system, while $Na_V$'s 1.1, 1.2, 1.3, and 1.6 are neuronal channels found in both the central and peripheral nervous systems. The functional behaviors of the nine isoforms are similar but distinct in the specifics of their voltage-dependent and kinetic behavior (Catterall, W. A., Goldin, A. L., and Waxman, S. G., International Union of Pharmacology. XLVII. Nomenclature and structure-function relationships of voltage-gated sodium channels. *Pharmacol Rev* 57 (4), p. 397 (2005)).

Immediately upon their discovery, $Na_V1.8$ channels were identified as likely targets for analgesia (Akopian, A. N., L. Sivilotti, and J. N. Wood, A tetrodotoxin-resistant voltage-gated sodium channel expressed by sensory neurons. *Nature*, 1996. 379(6562): p. 257-62). Since then, $Na_V1.8$ has been shown to be the most significant carrier of the sodium current that maintains action potential firing in small DRG neurons (Blair, N. T. and B. P. Bean, Roles of tetrodotoxin (TTX)-sensitive Na+ current, TTX-resistant $Na^+$ current, and $Ca^{2+}$ current in the action potentials of nociceptive sensory neurons. *J Neurosci.*, 2002. 22(23): p. 10277-90). $Na_V1.8$ is essential for spontaneous firing in damaged neurons, like those that drive neuropathic pain (Roza, C., et al., The tetrodotoxin-resistant $Na^+$ channel $Na_V1.8$ is essential for the expression of spontaneous activity in damaged sensory axons of mice. *J. Physiol.*, 2003. 550(Pt 3): p. 921-6; Jarvis, M. F., et al., A-803467, a potent and selective $Na_V1.8$ sodium channel blocker, attenuates neuropathic and inflammatory pain in the rat. *Proc Natl Acad Sci. USA*, 2007. 104(20): p. 8520-5; Joshi, S. K., et al., Involvement of the TTX-resistant sodium channel NaV1.8 in inflammatory and neuropathic, but not post-operative, pain states. *Pain*, 2006. 123(1-2): pp. 75-82; Lai, J., et al., Inhibition of neuropathic pain by decreased expression of the tetrodotoxin-resistant sodium channel, $Na_V1.8$. *Pain*, 2002. 95(1-2): p. 143-52; Dong, X. W., et al., Small interfering RNA-mediated selective knockdown of $Na(_V)1.8$ tetrodotoxin-resistant sodium channel reverses mechanical allodynia in neuropathic rats. *Neuroscience*, 2007. 146(2): p. 812-21; Huang, H. L., et al., Proteomic profiling of neuromas reveals alterations in protein composition and local protein synthesis in hyper-excitable nerves. *Mol Pain*, 2008. 4: p. 33; Black, J. A., et al., Multiple sodium channel isoforms and mitogen-activated protein kinases are present in painful human neuromas. *Ann Neurol*, 2008. 64(6): p. 644-53; Coward, K., et al., Immunolocalization of SNS/PN3 and NaN/SNS2 sodium channels in human pain states. *Pain*, 2000. 85(1-2): p. 41-50; Yiangou, Y., et al., SNS/PN3 and SNS2/NaN sodium channel-like immunoreactivity in human adult and neonate injured sensory nerves. *FEBS Lett*, 2000. 467(2-3): p. 249-52; Ruangsri, S., et al., Relationship of axonal voltage-gated sodium channel 1.8 ($Na_V1.8$) mRNA accumulation to sciatic nerve injury-induced painful neuropathy in rats. *J Biol Chem.* 286(46): p. 39836-47). The small DRG neurons where $Na_V1.8$ is expressed include the nociceptors critical for pain signaling. $Na_V1.8$ is the primary channel that mediates large amplitude action potentials in small neurons of the dorsal root ganglia (Blair, N. T. and B. P. Bean, Roles of tetrodotoxin (TTX)-sensitive $Na^+$ current, TTX-resistant $Na^+$ current, and $Ca^{2+}$ current in the action potentials of nociceptive sensory neurons. *J Neurosci.*, 2002. 22(23): p. 10277-90). $Na_V1.8$ is necessary for rapid repetitive action potentials in nociceptors, and for spontaneous activity of damaged neurons. (Choi, J. S. and S. G. Waxman, Physiological interactions between $Na_V1.7$ and $Na_V1.8$ sodium channels: a computer simulation study. *J Neurophysiol.* 106(6): p. 3173-84; Renganathan, M., T. R. Cummins, and S. G. Waxman, Contribution of $Na(_v)1.8$ sodium channels to action potential electrogenesis in DRG neurons. *J Neurophysiol.*, 2001. 86(2): p. 629-40; Roza, C., et al., The tetrodotoxin-resistant $Na^+$ channel $Na_V1.8$ is essential for the expression of spontaneous activity in damaged sensory axons of mice. *J Physiol.*, 2003. 550(Pt 3): p. 921-6). In depolarized or damaged DRG neurons, $Na_V1.8$ appears to be the primary driver of hyper-excitablility (Rush, A. M., et al., A single sodium channel mutation produces hyper- or hypo-excitability in different types of neurons. *Proc Natl Acad Sci USA*, 2006. 103(21): p. 8245-50). In some animal pain models, $Na_V1.8$ mRNA expression levels have been shown to increase in the DRG (Sun, W., et al., Reduced conduction failure of the main axon of polymodal nociceptive C-fibres contributes to painful diabetic neuropathy in rats. *Brain.* 135(Pt 2): p. 359-75; Strickland, I. T., et al., Changes in the expression of NaV1.7, $Na_V1.8$ and $Na_V1.9$ in a distinct population of dorsal root ganglia innervating the rat knee joint in a model of chronic inflammatory joint pain. *Eur J Pain*, 2008. 12(5): p. 564-72; Qiu, F., et al., Increased expression of tetrodotoxin-resistant sodium channels $Na_V1.8$ and $Na_V1.9$ within dorsal root ganglia in a rat model of bone cancer pain. *Neurosci. Lett.* 512(2): p. 61-6).

The primary drawback to the known $Na_V$ inhibitors is their poor therapeutic window, and this is likely a consequence of their lack of isoform selectivity. Since $Na_V1.8$ is primarily restricted to the neurons that sense pain, selective $Na_V1.8$ blockers are unlikely to induce the adverse events common to non-selective $Na_V$ blockers. Accordingly, there remains a need to develop additional $Na_V$ channel antagonists preferably those that are more NaV1.8 selective and more potent with increased metabolic stability, increased solubility and with fewer side effects.

SUMMARY OF THE INVENTION

It has now been found that compounds of this invention, and pharmaceutically acceptable salts and compositions thereof, are useful as inhibitors of voltage-gated sodium channels. These compounds have the general formula I:

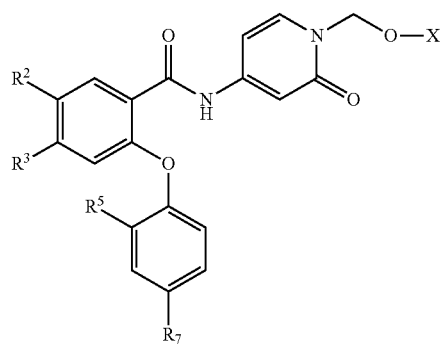

I wherein, independently for each occurrence:
$R^2$ and $R^3$ are independently hydrogen, halogen, or $C_1$-$C_6$ alkyl wherein said $C_1$-$C_6$ alkyl is substituted with 0-6 halogen;
$R^5$ is hydrogen, halogen, OH, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^7$ is hydrogen, halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation; provided that $R^2$, $R^3$, $R^5$, and $R^7$ are not simultaneously hydrogen.

The present invention also relates to novel, solid forms of (4-(2-(4-fluoro-2-methylphenoxy)-4-(trifluoromethyl)benzamido)-2-oxopyridin-1(2H)-yl)methyl dihydrogen phosphate ('compound 9"). In one embodiment, the present invention provides solid Form B of compound 9, which is characterized by an X-ray powder diffraction (XRPD) comprising at least three approximate peak positions (degrees 2 theta [2θ]±0.2) when measured using Cu K$_\alpha$ radiation, selected from the group consisting of 4.4, 12.7, 13.3, 14.7, 15.2, 16.4, 18.0, 19.1, 19.3, 19.9, 20.2, 20.5, 21.0, 22.2, 23.5 24.2, 24.8, 26.3, 29.6, 30.1 and 31.3, when the XPRD is collected from about 4 to about 40 degrees two theta (2θ). Solid Form B may also be characterized by an X-ray powder diffraction pattern, as measured using Cu K$_\alpha$ radiation, substantially similar to FIG. 2 and an endothermic peak having an onset temperature at about 210° C. as measured by differential scanning calorimetry in which the temperature is scanned at about 10° C. per minute. The present application also provides a method for preparing crystal Form B of compound 9 by suspending a solid material of free compound 9 in a solvent system comprising water, an organic solvent or an organic solvent/water mixture and isolating the solid. In another embodiment, the present invention provides amorphous Form C of compound 9, which is characterized by an X-ray powder diffraction (XRPD) substantially similar to that in FIG. 5. In another embodiment, the present invention provides a spray dry dispersion of amorphous Form C of compound 9, which is characterized by an X-ray powder diffraction (XRPD) substantially similar to that in FIG. 6.

In addition to the compounds provided herein, the present invention further provides pharmaceutically acceptable compositions comprising a compound of formula I and a pharmaceutically acceptable carrier, adjuvant, or vehicle.

In another embodiment, the present invention relates to a pharmaceutical composition comprising a compound of formula I; a pharmaceutically acceptable carrier, adjuvant, or vehicle; and an additional therapeutic agent.

In another embodiment, the present invention relates to a method of treating or lessening the severity of a variety of diseases, disorders, or conditions in a subject, including, but not limited to, chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia comprising administering to the subject a therapeutically effective amount of a compound of formula I.

In another embodiment, the present invention relates to a method of treating or lessening the severity of a variety of diseases, disorders, or conditions in a subject, including, but not limited to, chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia comprising administering to the subject a therapeutically effective amount of a compound of formula I and an additional therapeutic agent.

DETAILED DESCRIPTION OF THE INVENTION

Figure 1:
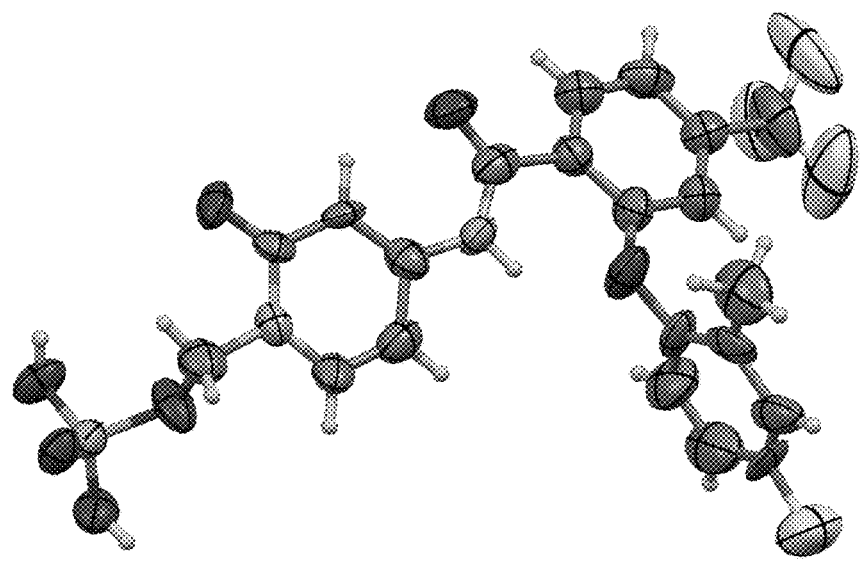
FIG. 1 is a thermal ellipsoid plot of one symmetry independent molecule of crystalline Form B of (4-(2-(4-fluoro-2-methylphenoxy)-4-(trifluoromethyl)benzamido)-2-oxopyridin-1(2H)-yl)methyl dihydrogen phosphate.

The instant compounds of formula I are prodrugs of their respective parent compounds. Thus, the activity exhibited upon administration of the prodrug is principally due to the presence of the parent compound that results from cleavage of the prodrug.

The present invention also relates to novel, solid forms of (4-(2-(4-fluoro-2-methylphenoxy)-4-(trifluoromethyl)benzamido)-2-oxopyridin-1 (2H)-yl)methyl dihydrogen phosphate ("compound 9"). In one embodiment, the present invention provides a free crystalline form of compound 9 (Form B). In another embodiment, the present invention provides a process for preparing solid Form B of compound 9. In another embodiment, the present invention provides an amorphous form of compound 9 (Form C). In yet another embodiment, the present invention provides a method of preparing amorphous Form C of compound 9.

The term "prodrug" refers to compounds which are drug precursors which, following administration and absorption, release the drug in vivo via some metabolic process. In general, a prodrug possesses less biological activity than its parent drug. A prodrug may also improve the physical properties of the parent drug and/or it may also improve overall drug efficacy, for example through the reduction of toxicity and unwanted effects of a drug by controlling its absorption, blood levels, metabolic distribution and cellular uptake.

The term "parent compound" or "parent drug" refers to the biologically active entity that is released via enzymatic action of a metabolic or a catabolic process, or via a chemical process following administration of the prodrug. The parent compound may also be the starting material for the preparation of its corresponding prodrug.

The monovalent cations defined by $M^+$ include ammonium (e.g., $N(R^9)_4$, wherein $R^9$ is H or $C_1$-$C_4$ alkyl), alkali metal ions such as sodium, lithium and potassium ions, dicyclohexylamine ion, and N-methyl-D-glucamine ion. The divalent cations defined by $D^{2+}$ include-alkaline earth metal ions such as calcium and magnesium ions, as well as divalent aluminum ions. Also included are amino acid cations such as monovalent or divalent ions of arginine, lysine, ornithine, and so forth. If $M^+$ is a monovalent cation, it is recognized that if the definition $2M^+$ is present, each of $M^+$ may be the same or different. In addition, it is similarly recognized that if the definition $2M^+$ is present, a divalent cation $D^{2+}$ may instead be present. Also, the basic nitrogen-containing groups may be quaternized with such agents as: lower alkyl halides, such as methyl, ethyl, propyl, and butyl chloride, bromides and iodides; dialkyl sulfates like dimethyl, diethyl, dibutyl; diamyl sulfates; long chain halides such as decyl, lauryl, myristyl and stearyl chlorides, bromides and iodides; aralkyl halides like benzyl bromide and others.

The prodrugs and solid forms of the present invention are characterized by unexpectedly high aqueous solubility. This solubility facilitates administration of higher doses of the prodrug, resulting in a greater drug load per unit dosage.

For purposes of this invention, the chemical elements are identified in accordance with the Periodic Table of the Elements, CAS version, Handbook of Chemistry and Physics, 75th Ed. Additionally, general principles of organic chemistry are described in "Organic Chemistry," Thomas Sorrell, University Science Books, Sausalito: 1999, and "March's Advanced Organic Chemistry," 5th Ed., Ed.: Smith, M. B. and March, J., John Wiley & Sons, New York: 2001, the entire contents of which are hereby incorporated by reference.

As one of ordinary skill in the art will recognize, combinations of substituents envisioned by this invention are those combinations that result in the formation of stable or chemically feasible compounds. The term "stable," as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "alkyl" as used herein, means a straight-chain (i.e., unbranched) or branched, substituted or unsubstituted hydrocarbon chain that is completely saturated or that contains one or more units of unsaturation. Suitable alkyl groups include, but are not limited to, linear or branched, and substituted or unsubstituted alkyl.

The term "halogen" or "halo" as used herein, means F, Cl, Br or I.

The phrase "up to," as used herein, refers to zero or any integer number that is equal or less than the number following the phrase. For example, "up to 4" means any one of 0, 1, 2, 3, and 4.

Within a definition of a term as, for example, 127 when a $CH_2$ unit or, interchangeably, methylene unit may be replaced by —O—, it is meant to include any $CH_2$ unit, including a $CH_2$ within a terminal methyl group. For example, $CH_2CH_2CH_2OH$ is within the definition of $C_1$-$C_6$ alkyl wherein up to two non-adjacent $CH_2$ units may be replaced by —O— because the $CH_2$ unit of the terminal methyl group has been replaced by —O—.

Unless otherwise stated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Thus, included within the scope of the invention are tautomers of compounds of formula I. The structures also include zwitterioinc forms of the compounds or salts of formula where appropriate.

Additionally, unless otherwise stated, structures depicted herein are also meant to include compounds that differ only in the presence of one or more isotopically enriched or isotopically-labeled atoms. The isotopically-labeled compounds may have one or more atoms replaced by an atom having an atomic mass or mass number usually found in nature. Examples of isotopes present in compounds of formula I include isotopes of hydrogen, carbon, nitrogen, oxygen, phosphorus, fluorine and chlorine, such as, but not limited to, $^2H$, $^3H$, $^{13}C$, $^{14}C$, $^{15}N$, $^{18}O$, $^{17}O$, $^{35}S$ and $^{18}F$. Certain isotopically-labeled compounds of formula I, in addition to being useful as therapeutic agents, are also useful in drug and/or substrate tissue distribution assays, as analytical tools or as probes in other biological assays. In one aspect of the present invention, tritiated (e.g., $^3H$) and carbon-14 (e.g., $^{14}C$) isotopes are useful given their ease of detectability. In another aspect of the present invention, replacement of one or more hydrogen atoms with heavier isotopes such as deuterium, (e.g., $^2H$) can afford certain therapeutic advantages.

In one embodiment, the invention features a compound of formula I and the attendant definitions, wherein $R^2$ is H. In another embodiment, $R^2$ is halogen. In another embodiment, $R^2$ is Cl. In another embodiment, $R^2$ is F. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is H, Cl or $CF_3$.

In another embodiment, the invention features a compound of formula I and the attendant definitions, wherein $R^3$ is H. In another embodiment, $R^3$ is halogen. In another embodiment, $R^3$ is Cl. In another embodiment, $R^3$ is $C_1$-$C_6$ alkyl wherein said $C_1$-$C_6$ alkyl is substituted with 0-6 halogen. In another embodiment, $R^3$ is $CF_3$. In another embodiment, $R^3$ is $CF_2CF_3$.

In another embodiment, the invention features a compound of formula I and the attendant definitions, wherein $R^5$ is H. In another embodiment, $R^5$ is halogen. In another embodiment, $R^5$ is Cl. In another embodiment, $R^5$ is F. In another embodiment, $R^5$ is $C_1$-$C_6$ alkyl. In another embodiment, $R^5$ is $CH_3$. In another embodiment, $R^5$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$. In another embodiment, $R^5$ is OH. In another embodiment, $R^5$ is $OCF_3$.

In another embodiment, the invention features a compound of formula I and the attendant definitions, wherein $R^7$ is H. In another embodiment, $R^7$ is halogen. In another embodiment, $R^7$ is F. In another embodiment, $R^7$ is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_3$. In another embodiment, $R^7$ is $OCF_3$.

In another embodiment, the invention features a compound of formula I and the attendant definitions, wherein X is —PO(OH)O$^-$M$^+$, —PO(O$^-$)$_2$.2M$^+$; or —PO(O$^-$)$_2$.D$^{2+}$; M$^+$ is Li$^+$, Na$^+$, K$^+$ or N(R$^9$)$_4^+$; wherein each R$^9$ is independently H or a $C_1$-$C_4$ alkyl group and D$^{2+}$ is Mg$^{2+}$, Ca$^{2+}$ or Ba$^{2+}$.

In another embodiment, the invention features a compound of formula I and the attendant definitions, wherein X is —PO(OH)O$^-$M$^+$ and M$^+$ is Li$^+$. In one embodiment, X is PO(OH)O$^-$M$^+$ and M$^+$ is Na$^+$. In another embodiment, X is —PO(OH)O$^-$M$^+$ and M$^+$ is K. In another embodiment, X is —PO(OH)O$^-$M$^+$ and M$^+$ is N(R$^9$)$_4^+$; wherein each R$^9$ is independently H or a $C_1$-$C_4$ alkyl group. In another embodiment, X is —PO(OH)O$^-$M$^+$ and M$^+$ is N(R$^9$)$_4^+$; wherein each R$^9$ is a $CH_3$ group. In another embodiment, the invention features a compound of formula I and the attendant definitions, wherein X is —PO(O$^-$)$_2$.2M$^+$ and M$^+$ is Li$^+$. In one embodiment, X is PO(O$^-$)$_2$.2M$^+$ and M$^+$ is Na$^+$. In another embodiment, X is —PO(O$^-$)$_2$.2M$^+$ and M$^+$ is K$^+$. In another embodiment, X is —PO(O$^-$)$_2$.2M$^+$ and M$^+$ is N(R$^9$)$_4^+$; wherein each R$^9$ is independently H or a $C_1$-$C_4$ alkyl group. In another embodiment, X is —PO(O$^-$)$_2$.2M$^+$ and M$^+$ is N(R$^9$)$_4^+$; wherein each R$^9$ is a $CH_3$ group.

In another embodiment, the invention features a compound of formula I and the attendant definitions, wherein X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$. In another embodiment, X is —PO(O$^-$)$_2$.D$^{2+}$ and D$^{2+}$ is Ba$^{2+}$.

In another embodiment, the invention features a compound of formula I and the attendant definitions, wherein X is —PO(OH)$_2$.

In another embodiment, the invention features a compound of formula I and the attendant definitions, wherein $R^2$ is Cl, $R^3$ is Cl, $R^5$ is $OCH_3$, $R^7$ is F and X is —PO(OH)$_2$.

In another embodiment, the invention features a compound of formula I and the attendant definitions, wherein $R^2$ is Cl, $R^3$ is Cl, $R^5$ is $OCH_3$, $R^7$ is F and X is —PO(O$^-$)$_2$.2M$^+$, M$^t$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^2$ is Cl, $R^3$ is Cl, $R^5$ is $OCH_3$, $R^7$ is F and X is —PO(OH)O$^-$M$^+$, M$^+$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^3$ is $CF_2CF_3$, $R^5$ is $OCH_3$, $R^7$ is F and X is —PO(OH)$_2$.

In another embodiment, the invention features a compound of formula I and the attendant definitions, wherein $R^3$ is $CF_2CF_3$, $R^5$ is $OCH_3$, $R^7$ is F and X is —PO(O$^-$)$_2$.2M$^+$, M$^+$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^3$ is $CF_2CF_3$, $R^5$ is $OCH_3$, $R^7$ is F and X is —PO(OH)O$^-$M$^+$, M$^+$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^3$ is $CF_3$, $R^5$ is $CH_3$, $R^7$ is F and X is —PO(OH)$_2$.

In another embodiment, the invention features a compound of formula I and the attendant definitions, wherein $R^3$ is $CF_3$, $R^5$ is $CH_3$, $R^7$ is F, X is —PO(O$^-$)$_2$.2M$^+$, M$^+$ is Li$^+$, Na$^+$, K$^+$. In another embodiment, M$^+$ is Li$^+$. In yet another embodiment, M$^+$ is Na$^+$.

In another embodiment, the invention features a compound of formula I and the attendant definitions, wherein $R^3$ is $CF_3$, $R^5$ is $CH_3$, $R^7$ is F, X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$.

In another embodiment, the invention features a compound of formula I and the attendant definitions, wherein $R^2$ is $CF_3$, $R^5$ is $CH_3$, $R^7$ is F and X is —PO(OH)$_2$.

In another embodiment, the invention features a compound of formula I and the attendant definitions, wherein $R^2$ is $CF_3$, $R^5$ is $CH_3$, $R^7$ is F, X is —PO(O$^-$)$_2$.2M$^+$, M$^+$ is Li$^+$, Na$^+$, K$^+$. In another embodiment, M$^+$ is Li$^+$. In yet another embodiment, M$^+$ is Na$^+$.

In another embodiment, the invention features a compound of formula I and the attendant definitions, wherein $R^2$ is $CF_3$, $R^5$ is $CH_3$, $R^7$ is F, X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$.

In another embodiment, the invention features a compound of formula I and the attendant definitions, wherein $R^3$ is Cl, $R^5$ is $CH_3$, $R^7$ is F and X is —PO(OH)$_2$.

In another embodiment, the invention features a compound of formula I and the attendant definitions, wherein $R^3$ is Cl, $R^5$ is $CH_3$, $R^7$ is F and X is —PO(O$^-$)$_2$.2M$^+$, M$^+$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^3$ is Cl, $R^5$ is $CH_3$, $R^7$ is F and X is —PO(OH)O$^-$M$^+$, M$^+$ is Li$^+$, Na$^+$, K$^+$ or N(R$^9$)$_4^+$ wherein each R$^9$ is independently H or a $C_1$-$C_4$ alkyl group.

In another embodiment, the invention features a compound of formula I and the attendant definitions, wherein $R^2$ is $CF_3$, $R^5$ is $CH_3$, $R^7$ is F and X is —PO(OH)$_2$.

In another embodiment, the invention features a compound of formula I and the attendant definitions, wherein $R^2$ is $CF_3$, $R^7$ is F, X is —PO(O$^-$)$_2$.2M$^+$, M$^+$ is Li$^+$, Na$^+$, K$^+$. In another embodiment, M$^+$ is Li$^+$. In yet another embodiment, M$^+$ is Na$^+$.

In another embodiment, the invention features a compound of formula I and the attendant definitions, wherein $R^2$ is $CF_3$, $R^7$ is F, X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$.

In another embodiment, the invention provides a compound of formula I-A

I-A wherein, independently for each occurrence:
$R^2$ is halogen, or $C_1$-$C_6$ alkyl wherein said $C_1$-$C_6$ alkyl is substituted with 0-6 halogen;
$R^5$ is halogen, OH, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—;
$R^7$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

In another embodiment, the invention features a compound of formula I-A and the attendant definitions, wherein $R^2$ is halogen. In another embodiment, $R^2$ is Cl. In another embodiment, $R^2$ is F. In another embodiment, $R^2$ is $C_1$-$C_6$ alkyl wherein said $C_1$-$C_6$ alkyl is substituted with 0-6 halogen. In another embodiment, $R^2$ is $CF_3$. In another embodiment, $R^2$ is Cl or $CF_3$.

In another embodiment, the invention features a compound of formula I-A and the attendant definitions, wherein $R^5$ is halogen. In another embodiment, $R^5$ is Cl. In another embodiment, $R^5$ is F. In another embodiment, $R^5$ is $C_1$-$C_6$ alkyl. In another embodiment, $R^5$ is $CH_3$. In another embodiment, $R^5$ is $C_1$-$C_6$ alkyl wherein said $C_1$-$C_6$ alkyl is substituted with 0-6 halogen wherein one $CH_2$ unit of said $C_1$-$C_6$ alkyl is replaced with —O—. In another embodiment, $R^5$ is $OCH_3$. In another embodiment, $R^5$ is OH. In another embodiment, $R^5$ is $OCF_3$. In another embodiment, $R^5$ is F, Cl, $CH_3$, $OCH_3$, OH or $OCF_3$.

In another embodiment, the invention features a compound of formula I-A and the attendant definitions, wherein $R^7$ is halogen. In another embodiment, $R^7$ is F. In another embodiment, $R^7$ is $C_1$-$C_6$ alkyl wherein said $C_1$-$C_6$ alkyl is substituted with 0-6 halogen wherein two non-adjacent $CH_2$ units of said $C_1$-$C_6$ alkyl are replaced with —O—. In another embodiment, $R^7$ is $OCH_3$. In another embodiment, $R^7$ is $OCF_3$. In another embodiment, $R^7$ is F, $OCH_3$ or $OCF_3$.

In another embodiment, the invention features a compound of formula I-A and the attendant definitions, wherein X is —PO(OH)$_2$, —PO(OH)O$^-$M$^+$; PO(O$^-$)$_2$.2M$^+$ or —PO(O$^-$)$_2$.D$^{2+}$; wherein M$^+$ is Li$^+$, Na$^+$ or K$^+$ and wherein D$^{2+}$ is Mg$^{2+}$ or Ca$^{2+}$.

In another embodiment, the invention features a compound of formula I-A and the attendant definitions, wherein $R^2$ is $CF_3$, $R^5$ is Cl, $OCH_3$ or $CH_3$ and $R^7$ is F. In one embodiment, $R^2$ is $CF_3$, $R^5$ is Cl and $R^7$ is F. In another embodiment, $R^2$ is $CF_3$, $R^5$ is $OCH_3$ and $R^7$ is F. In another embodiment, $R^2$ is $CF_3$, $R^5$ is $CH_3$ and $R^7$ is F.

In another embodiment, the invention features a compound of formula I-A and the attendant definitions, wherein $R^2$ is $CF_3$, $R^5$ is Cl, $OCH_3$ or $CH_3$, $R^7$ is F and X is —PO(OH)$_2$. In one embodiment, $R^2$ is $CF_3$, $R^5$ is Cl, $R^7$ is F and X is —PO(OH)$_2$. In another embodiment, $R^2$ is $CF_3$, $R^5$ is $OCH_3$, $R^7$ is F and X is —PO(OH)$_2$. In another embodiment, $R^2$ is $CF_3$, $R^5$ is $CH_3$, $R^7$ is F and X is —PO(OH)$_2$.

In another embodiment, the invention features a compound of formula I-A and the attendant definitions, wherein X is —PO(OH)O$^-$M$^+$, —PO(O$^-$)$_2$.2M$^+$; or —PO(O$^-$)$_2$.D$^{2+}$; M$^+$ is Li$^+$, Na$^+$, K$^+$ or N(R$^9$)$_4^+$; wherein each R$^9$ is independently H or a $C_1$-$C_4$ alkyl group and D$^{2+}$ is Mg$^{2+}$, Ca$^{2+}$ or Ba$^{2+}$.

In another embodiment, the invention features a compound of formula I-A and the attendant definitions, wherein X is —PO(OH)O$^-$M$^+$ and M$^+$ is Li$^+$. In one embodiment, X is PO(OH)O$^-$M$^+$ and M$^+$ is Na$^+$. In another embodiment, X is —PO(OH)O$^-$M$^+$ and M$^+$ is K$^+$. In another embodiment, X is —PO(OH)O$^-$M$^+$ and M$^+$ is N(R$^9$)$_4^+$; wherein each R$^9$ is independently H or a $C_1$-$C_4$ alkyl group. In another embodiment, X is —PO(OH)O$^-$M$^+$ and M$^+$ is N(R$^9$)$_4^+$; wherein each R$^9$ is a CH$_3$ group.

In another embodiment, the invention features a compound of formula I-A and the attendant definitions, wherein X is —PO(O$^-$)$_2$.2M$^+$ and M$^+$ is Li$^+$. In one embodiment, X is —PO(O$^-$)$_2$.2M$^+$ and M$^+$ is Na$^+$. In another embodiment, X is —PO(O$^-$)$_2$.2M$^+$ and M$^+$ is K$^+$. In another embodiment, X is —PO(O$^-$)$_2$.2M$^+$ and M$^+$ is N(R$^9$)$_4^+$; wherein each R$^9$ is independently H or a $C_1$-$C_4$ alkyl group. In another embodiment, X is —PO(O$^-$)$_2$.2M$^+$ and M$^+$ is N(R$^9$)$_4^+$; wherein each R$^9$ is a CH$_3$ group.

In another embodiment, the invention features a compound of formula I-A and the attendant definitions, wherein X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$. In another embodiment, X is —PO(O$^-$)$_2$.D$^{2+}$ and D$^{2+}$ is Ba$^{2+}$.

In another embodiment, the invention features a compound of formula I-A and the attendant definitions, wherein X is —PO(OH)$_2$.

In another embodiment, the invention features a compound of formula I-A and the attendant definitions, wherein $R^2$ is $CF_3$, $R^5$ is $CH_3$, $R^7$ is F and X is —PO(OH)$_2$.

In another embodiment, the invention features a compound of formula I-A and the attendant definitions, wherein $R^2$ is $CF_3$, $R^5$ is $CH_3$, $R^7$ is F, X is —PO(O$^-$)$_2$.2M$^+$, M$^+$ is Li$^+$, Na$^+$, K$^+$. In another embodiment, M$^+$ is Li$^+$. In yet another embodiment, M$^+$ is Na$^+$.

In another embodiment, the invention features a compound of formula I-A and the attendant definitions, wherein $R^2$ is $CF_3$, $R^5$ is $CH_3$, $R^7$ is F, X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$.

In another embodiment, the invention provides a compound of formula I-B

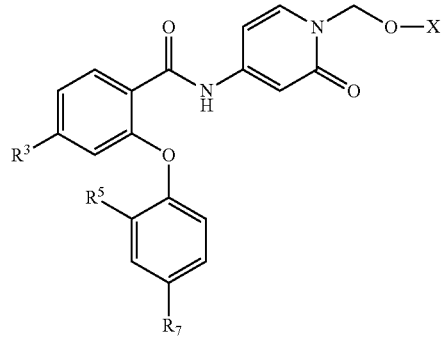

I-B wherein, independently for each occurrence:
$R^3$ is halogen, or $C_1$-$C_6$ alkyl wherein said $C_1$-$C_6$ alkyl is substituted with 0-6 halogen;
$R^5$ is halogen, OH, or $C_1$-$C_6$ alkyl wherein said $C_1$-$C_6$ alkyl is substituted with 0-6 halogen and wherein up to two non-adjacent CH$_2$ units of said $C_1$-$C_6$ alkyl may be replaced with —O—;
$R^7$ is halogen, or $C_1$-$C_6$ alkyl wherein said $C_1$-$C_6$ alkyl is substituted with 0-6 halogen and wherein up to two non-adjacent CH$_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

In another embodiment, the invention features a compound of formula I-B and the attendant definitions, wherein $R^3$ is halogen. In another embodiment, $R^3$ is Cl. In another embodiment, $R^3$ is $C_1$-$C_6$ alkyl wherein said $C_1$-$C_6$ alkyl is substituted with 0-6 halogen. In another embodiment, $R^3$ is $CF_3$. In another embodiment, $R^3$ is $CF_2CF_3$.

In another embodiment, the invention features a compound of formula I-B and the attendant definitions, wherein $R^5$ is halogen. In another embodiment, $R^5$ is Cl. In another embodiment, $R^5$ is F. In another embodiment, $R^5$ is $C_1$-$C_6$ alkyl. In another embodiment, $R^5$ is $CH_3$. In another embodiment, $R^5$ is $C_1$-$C_6$ alkyl wherein said $C_1$-$C_6$ alkyl is substituted with 0-6 halogen wherein one CH$_2$ unit of said $C_1$-$C_6$ alkyl is replaced with —O—. In another embodiment, $R^5$ is $OCH_3$. In another embodiment, $R^5$ is OH. In another embodiment, $R^5$ is $OCF_3$.

In another embodiment, the invention features a compound of formula I-B and the attendant definitions, wherein $R^7$ is halogen. In another embodiment, $R^7$ is F. In another embodiment, $R^7$ is $C_1$-$C_6$ alkyl wherein said $C_1$-$C_6$ alkyl is substituted with 0-6 halogen wherein two non-adjacent CH$_2$ units of said $C_1$-$C_6$ alkyl are replaced with —O—. In another embodiment, $R^7$ is $OCH_3$. In another embodiment, $R^7$ is $OCF_3$.

In another embodiment, the invention features a compound of formula I-B and the attendant definitions, wherein X is X is —PO(OH)$_2$, —PO(OH)O$^-$M$^+$; PO(O$^-$)$_2$.2M$^+$ or —PO(O$^-$)$_2$.D$^{2+}$; wherein M$^+$ is Li$^+$, Na$^+$ or K$^+$ and wherein D$^{2+}$ is Mg$^{2+}$ or Ca$^{2+}$.

In another embodiment, the invention features a compound of formula I-B and the attendant definitions, wherein $R^3$ is $CF_3$, $R^5$ is F or $CH_3$ and $R^7$ is F. In one embodiment, $R^3$ is Cl, $R^5$ is $CH_3$ and $R^7$ is F. In another embodiment, $R^3$ is $CF_2CF_3$, $R^5$ is $OCH_3$ and $R^7$ is F.

In another embodiment, the invention features a compound of formula I-B and the attendant definitions, wherein $R^3$ is $CF_3$, $R^5$ is F or $CH_3$, $R^7$ is F and X is $—PO(OH)_2$. In one embodiment, $R^3$ is Cl, $R^5$ is $CH_3$, $R^7$ is F and X is $—PO(OH)_2$. In another embodiment, $R^3$ is $CF_2CF_3$, $R^5$ is $OCH_3$, $R^7$ is F and X is $—PO(OH)_2$.

In another embodiment, the invention features a compound of formula I-B and the attendant definitions, wherein X is $—PO(OH)O^-M^+$, $—PO(O^-)_2.2M^+$; or $—PO(O^-)_2.D^{2+}$; $M^+$ is $Li^+$, $Na^+$, $K^+$ or $N(R^9)_4^+$; wherein each $R^9$ is independently H or a $C_1$-$C_4$ alkyl group and is $Mg^+$, $Ca^{2+}$ or $Ba^{2+}$.

In another embodiment, the invention features a compound of formula I-B and the attendant definitions, wherein X is $—PO(OH)O^-M^+$ and $M^+$ is $Li^+$. In one embodiment, X is $PO(OH)O^-M^+$ and $M^+$ is $Na^+$. In another embodiment, X is $—PO(OH)O^-M^+$ and $M^+$ is $K^+$. In another embodiment, X is $—PO(OH)O^-M^+$ and $M^+$ is $N(R^9)_4^+$; wherein each $R^9$ is independently H or a $C_1$-$C_4$ alkyl group. In another embodiment, X is $—PO(OH)O^-M^+$ and $M^+$ is $N(R^9)_4^+$; wherein each $R^9$ is a $CH_3$ group.

In another embodiment, the invention features a compound of formula I-B and the attendant definitions, wherein X is $—PO(O^-)_2.2M^+$ and $M^+$ is $Li^+$. In one embodiment, X is $—PO(O^-)$ $2.2M^+$ and $M^+$ is $Na^+$. In another embodiment, X is $—PO(O^-)_2.2M^+$ and $M^+$ is $K^+$. In another embodiment, X is $—PO(O^-)_2.2M^+$ and $M^+$ is $N(R^9)_4^+$; wherein each $R^9$ is independently H or a $C_1$-$C_4$ alkyl group. In another embodiment, X is $—PO(O^-)_2.2M^+$ and $M^+$ is $N(R^9)_4^+$; wherein each $R^9$ is a $CH_3$ group.

In another embodiment, the invention features a compound of formula I-B and the attendant definitions, wherein X is $—PO(O^-)_2.D^{2+}$ and $D^{2+}$ is $Mg^{2+}$, $Ca^{2+}$ or $Ba^{2+}$. In one embodiment, X is $—PO(O^-)_2.D^{2+}$ and $D^{2+}$ is $Mg^{2+}$. In another embodiment, X is $—PO(O^-)_2.D^{2+}$ and $D^{2+}$ is $Ca^{2+}$. In another embodiment, X is $—PO(O^-)_2.D^{2+}$ and $D^{2+}$ is $Ba^{2+}$.

In another embodiment, the invention features a compound of formula I-B and the attendant definitions, wherein X is $—PO(OH)_2$.

In another embodiment, the invention features a compound of formula I-B and the attendant definitions, wherein $R^3$ is $CF_2CF_3$, $R^5$ is $OCH_3$, $R^7$ is F and X is $—PO(OH)_2$.

In another embodiment, the invention features a compound of formula I-B and the attendant definitions, wherein $R^3$ is $CF_2CF_3$, $R^5$ is $OCH_3$, $R^7$ is F and X is $—PO(O^-)_2.2M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention features a compound of formula I-B and the attendant definitions, wherein $R^3$ is $CF_2CF_3$, $R^5$ is $OCH_3$, $R^7$ is F and X is $—PO(OH)O^-M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention features a compound of formula I-B and the attendant definitions, wherein $R^3$ is $CF_3$, $R^5$ is $CH_3$, $R^7$ is F and X is $—PO(OH)_2$.

In another embodiment, the invention features a compound of formula I-B and the attendant definitions, wherein $R^3$ is $CF_3$, $R^5$ is $CH_3$, $R^7$ is F, X is $—PO(O^-)_2.2M^+$, $M^+$ is $Li^+$, $Na^+$, $K^+$. In another embodiment, $M^+$ is $Li^+$. In yet another embodiment, $M^+$ is $Na^+$.

In another embodiment, the invention features a compound of formula I-B and the attendant definitions, wherein $R^3$ is $CF_3$, $R^5$ is $CH_3$, $R^7$ is F, X is $—PO(O^-)_2.D^{2+}$ and $D^{2+}$ is $Mg^{2+}$, $Ca^{2+}$ or $Ba^{2+}$. In one embodiment, X is $—PO(O^-)_2.D^{2+}$ and $D^{2+}$ is $Mg^{2+}$. In another embodiment, X is $—PO(O^-)_2.D^{2+}$ and $D^{2+}$ is $Ca^{2+}$.

In another embodiment, the invention features a compound of formula I-B and the attendant definitions, wherein $R^3$ is Cl, $R^5$ is $CH_3$, $R^7$ is F and X is $—PO(OH)_2$.

In another embodiment, the invention features a compound of formula I-B and the attendant definitions, wherein $R^3$ is Cl, $R^5$ is $CH_3$, $R^7$ is F and X is $—PO(O^-)_2.2M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention features a compound of formula I-B and the attendant definitions, wherein $R^3$ is Cl, $R^5$ is $CH_3$, $R^7$ is F and X is $—PO(OH)O^-M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention provides a compound of formula I-C

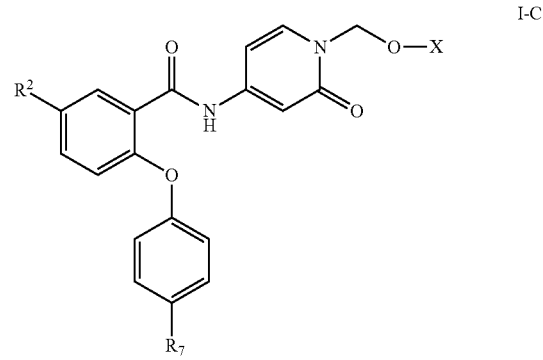

wherein, independently for each occurrence:
$R^2$ is halogen, or $C_1$-$C_6$ alkyl wherein said $C_1$-$C_6$ alkyl is substituted with 0-6 halogen;
$R^7$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
X is $—PO(OH)_2$, $—PO(OH)O^-M^+$, $—PO(O^-)_2.2M^+$, or $—PO(O^-)_2.D^{2+}$; $M^+$ is a pharmaceutically acceptable monovalent cation; and $D^{2+}$ is a pharmaceutically acceptable divalent cation.

In another embodiment, the invention features a compound of formula I-C and the attendant definitions, wherein $R^2$ is $C_1$-$C_6$ alkyl wherein said $C_1$-$C_6$ alkyl is substituted with 0-6 halogen. In another embodiment, $R^2$ is $CF_3$.

In another embodiment, the invention features a compound of formula I-C and the attendant definitions, wherein $R^7$ is halogen. In one embodiment, $R^7$ is F. In another embodiment, $R^7$ is $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—. In one embodiment, $R^7$ is $OCF_3$.

In another embodiment, the invention features a compound of formula I-C and the attendant definitions, wherein X is $—PO(OH)_2$, $—PO(OH)O^-M^+$; $PO(O^-)_2.2M^+$ or $—PO(O^-)_2.D^{2+}$; wherein $M^+$ is $Li^+$, $Na^+$ or $K^+$ and wherein $D^{2+}$ is $Mg^{2+}$ or $Ca^{2+}$.

In another embodiment, the invention features a compound of formula I-C and the attendant definitions, wherein $R^2$ is $CF_3$ and $R^7$ is F or $OCF_3$.

In another embodiment, the invention features a compound of formula I-C and the attendant definitions, wherein $R^2$ is $CF_3$, $R^7$ is F or $OCF_3$ and X is $—PO(OH)_2$.

In another embodiment, the invention features a compound of formula I-C and the attendant definitions, wherein X is —PO(OH)O⁻M⁺, —PO(O⁻)₂.2M⁺; or —PO(O⁻)₂.D²⁺; M⁺ is Li⁺, Na⁺, K⁺ or N(R⁹)₄⁺; wherein each R⁹ is independently H or a C₁-C₄ alkyl group and D²⁺ is Mg²⁺, Ca²⁺ or Ba²⁺.

In another embodiment, the invention features a compound of formula I-C and the attendant definitions, wherein X is —PO(OH)O⁻M⁺ and M⁺ is Li⁺. In one embodiment, X is PO(OH)O⁻M⁺ and M⁺ is Na⁺. In another embodiment, X is —PO(OH)O⁻M⁺ and M⁺ is K⁺. In another embodiment, X is —PO(OH)O⁻M⁺ and M⁺ is N(R⁹)₄⁺; wherein each R⁹ is independently H or a C₁-C₄ alkyl group. In another embodiment, X is —PO(OH)O⁻M⁺ and M⁺ is N(R⁹)₄⁺; wherein each R⁹ is a CH₃ group.

In another embodiment, the invention features a compound of formula I-C and the attendant definitions, wherein X is —PO(O⁻)₂.2M⁺ and M⁺ is Li⁺. In one embodiment, X is —PO(O⁻)₂.2M⁺ and M⁺ is Na⁺. In another embodiment, X is —PO(O⁻)₂.2M⁺ and M⁺ is K⁺. In another embodiment, X is —PO(O⁻)₂.2M⁺ and M⁺ is N(R⁹)₄⁺; wherein each R⁹ is independently H or a C₁-C₄ alkyl group. In another embodiment, X is —PO(O⁻)₂.2M⁺ and M⁺ is N(R⁹)₄⁺; wherein each R⁹ is a CH₃ group.

In another embodiment, the invention features a compound of formula I-C and the attendant definitions, wherein X is —PO(O⁻)₂.D²⁺ and D²⁺ is Mg²⁺, Ca²⁺ or Ba²⁺. In one embodiment, X is —PO(O⁻)₂.D²⁺ and D²⁺ is Mg²⁺. In another embodiment, X is —PO(O⁻)₂.D²⁺ and D²⁺ is Ca²⁺. In another embodiment, X is —PO(O⁻)₂.D²⁺ and is Ba²⁺.

In another embodiment, the invention features a compound of formula I-C and the attendant definitions, wherein X is —PO(OH)₂.

In another embodiment, the invention features a compound of formula I-C and the attendant definitions, wherein R² is CF₃, R⁵ is CH₃, R⁷ is F and X is —PO(OH)₂.

In another embodiment, the invention features a compound of formula I-C and the attendant definitions, wherein R² is CF₃, R⁷ is F, X is —PO(O⁻)₂.2M⁺, M⁺ is Li⁺, Na⁺, K⁺. In another embodiment, M⁺ is Li⁺. In yet another embodiment, M⁺ is Na⁺.

In another embodiment, the invention features a compound of formula I-C and the attendant definitions, wherein R² is CF₃, R⁷ is F, X is —PO(O⁻)₂.D²⁺ and D²⁺ is Mg²⁺, Ca²⁺ or Ba²⁺. In one embodiment, X is —PO(O⁻)₂.D²⁺ and D²⁺ is Mg²⁺. In another embodiment, X is —PO(O⁻)₂.D²⁺ and D²⁺ is Ca²⁺.

In another embodiment, the invention provides a compound of formula I-D

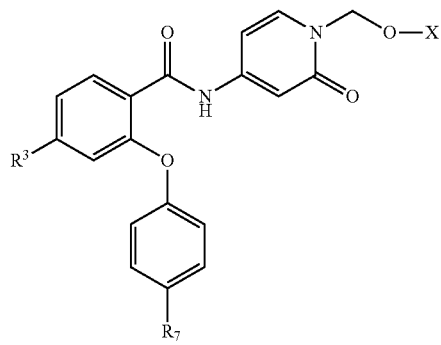

I-D wherein, independently for each occurrence:
R³ is halogen, or C₁-C₆ alkyl wherein said C₁-C₆ alkyl is substituted with 0-6 halogen;

R⁷ is halogen, or C₁-C₆ alkyl wherein said C₁-C₆ alkyl is substituted with 0-6 halogen and wherein up to two non-adjacent CH₂ units of said C₁-C₆ alkyl may be replaced with —O—; and
X is —PO(OH)₂, —PO(OH)O⁻M⁺, —PO(O⁻)₂.2M⁺, or —PO(O⁻)₂.D²⁺; M⁺ is a pharmaceutically acceptable monovalent cation; and D²⁺ is a pharmaceutically acceptable divalent cation.

In another embodiment, the invention features a compound of formula I-D and the attendant definitions, wherein R³ is C₁-C₆ alkyl wherein said C₁-C₆ alkyl is substituted with 0-6 halogen. In another embodiment, R³ is CF₃. In another embodiment, R³ is CF₂CF₃.

In another embodiment, the invention features a compound of formula I-D and the attendant definitions, wherein R⁷ is halogen. In one embodiment, R⁷ is F. In another embodiment, R⁷ is C₁-C₆ alkyl wherein said C₁-C₆ alkyl is substituted with 0-6 halogen and wherein up to two non-adjacent CH₂ units of said C₁-C₆ alkyl may be replaced with —O—. In one embodiment, R⁷ is OCF₃.

In another embodiment, the invention features a compound of formula I-D and the attendant definitions, wherein X is —PO(OH)₂, —PO(OH)O⁻M⁺; PO(O⁻)₂.2M⁺ or —PO(O⁻)₂.D²⁺; wherein M⁺ is Li⁺, Na⁺ or K⁺ and wherein D²⁺ is Mg²⁺ or Ca²⁺.

In another embodiment, the invention features a compound of formula I-D and the attendant definitions, wherein R³ is CF₃ and R⁷ is CF₃. In another embodiment, R³ is CF₂CF₃ and R⁷ is F.

In another embodiment, the invention features a compound of formula I-D and the attendant definitions, wherein R³ is CF₃, R⁷ is CF₃ and X is —PO(OH)₂. In another embodiment, R³ is CF₂CF₃, R⁷ is F and X is —PO(OH)₂.

In another embodiment, the invention features a compound of formula I-D and the attendant definitions, wherein X is —PO(OH)O⁻M⁺, —PO(O⁻)₂.2M⁺; or —PO(O⁻)₂.D²⁺; M⁺ is Li⁺, Na⁺, K⁺ or N(R⁹)₄⁺; wherein each R⁹ is independently H or a C₁-C₄ alkyl group and is Mg⁺, Ca²⁺ or Ba²⁺.

In another embodiment, the invention features a compound of formula I-D and the attendant definitions, wherein X is —PO(OH)O⁻M⁺ and M⁺ is Li⁺. In one embodiment, X is PO(OH)O⁻M⁺ and M⁺ is Na⁺. In another embodiment, X is —PO(OH)O⁻M⁺ and M⁺ is K⁺. In another embodiment, X is —PO(OH)O⁻M⁺ and M⁺ is N(R⁹)₄⁺; wherein each R⁹ is independently H or a C₁-C₄ alkyl group. In another embodiment, X is —PO(OH)O⁻M⁺ and M⁺ is N(R⁹)₄⁺; wherein each R⁹ is a CH₃ group.

In another embodiment, the invention features a compound of formula I-D and the attendant definitions, wherein X is —PO(O⁻)₂.2M⁺ and M⁺ is Li⁺. In one embodiment, X is —PO(O⁻) 2.2M⁺ and M⁺ is Na⁺. In another embodiment, X is —PO(O⁻)₂.2M⁺ and M⁺ is K⁺. In another embodiment, X is —PO(O⁻)₂.2M⁺ and M⁺ is N(R⁹)₄⁺; wherein each R⁹ is independently H or a C₁-C₄ alkyl group. In another embodiment, X is —PO(O⁻)₂.2M⁺ and M⁺ is N(R⁹)₄⁺; wherein each R⁹ is a CH₃ group.

In another embodiment, the invention features a compound of formula I-D and the attendant definitions, wherein X is —PO(O⁻)₂.D²⁺ and D²⁺ is Mg²⁺, Ca²⁺ or Ba²⁺. In one embodiment, X is —PO(O⁻)₂.D²⁺ and D²⁺ is Mg²⁺. In another embodiment, X is —PO(O⁻)₂.D²⁺ and D²⁺ is Ca²⁺. In another embodiment, X is —PO(O⁻)₂.D²⁺ and D²⁺ is Ba²⁺.

In another embodiment, the invention features a compound of formula I-D and the attendant definitions, wherein X is —PO(OH)₂.

In another embodiment, the invention provides a compound of formula I-E

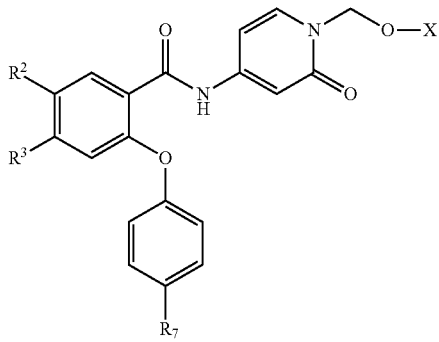

I-E wherein, independently for each occurrence:
$R^2$ and $R^3$ are independently halogen, or $C_1$-$C_6$ alkyl wherein said $C_1$-$C_6$ alkyl is substituted with 0-6 halogen;
$R^7$ is halogen, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

In another embodiment, the invention features a compound of formula I-E and the attendant definitions, wherein $R^2$ is halogen. In another embodiment, $R^2$ is Cl.

In another embodiment, the invention features a compound of formula I-E and the attendant definitions, wherein $R^3$ is halogen. In another embodiment, $R^3$ is Cl.

In another embodiment, the invention features a compound of formula I-E and the attendant definitions, wherein $R^7$ is halogen. In one embodiment, $R^7$ is F.

In another embodiment, the invention features a compound of formula I-E and the attendant definitions, wherein X is —PO(OH)$_2$, —PO(OH)O$^-$M$^+$; PO(O$^-$)$_2$.2M$^+$ or —PO(O$^-$)$_2$.D$^{2+}$; wherein M$^+$ is Li$^+$, Na$^+$ or K$^+$ and wherein D$^{2+}$ is Mg$^{2+}$ or Ca$^{2+}$.

In another embodiment, the invention features a compound of formula I-E and the attendant definitions, wherein $R^2$ and $R^3$ are Cl and $R^7$ is F.

In another embodiment, the invention features a compound of formula I-E and the attendant definitions, wherein $R^2$ and $R^3$ are Cl, $R^7$ is F and X is —PO(OH)$_2$.

In another embodiment, the invention features a compound of formula I-E and the attendant definitions, wherein X is —PO(OH)O$^-$M$^+$, —PO(O$^-$)$_2$.2M$^+$; or —PO(O$^-$)$_2$.D$^{2+}$; M$^+$ is Li$^+$, Na$^+$, K$^+$ or N(R$^9$)$_4^+$; wherein each R$^9$ is independently H or a $C_1$-$C_4$ alkyl group and D$^+$ is Mg$^+$, Ca$^{2+}$ or Ba$^{2+}$.

In another embodiment, the invention features a compound of formula I-E and the attendant definitions, wherein X is —PO(OH)O$^-$M$^+$ and M$^+$ is Li$^+$. In one embodiment, X is PO(OH)O$^-$M$^+$ and M$^+$ is Na$^+$. In another embodiment, X is —PO(OH)O$^-$M$^+$ and M$^+$ is K. In another embodiment, X is —PO(OH)O$^-$M$^+$ and M$^+$ is N(R$^9$)$_4^+$; wherein each R$^9$ is independently H or a $C_1$-$C_4$ alkyl group. In another embodiment, X is —PO(OH)O$^-$M$^+$ and M$^+$ is N(R$^9$)$_4^+$; wherein each R$^9$ is a CH$_3$ group.

In another embodiment, the invention features a compound of formula I-E and the attendant definitions, wherein X is —PO(O$^-$)$_2$.2M$^+$ and M$^+$ is Li$^+$. In one embodiment, X is —PO(O$^-$) 2.2M$^+$ and M$^+$ is Na$^+$. In another embodiment, X is —PO(O$^-$)$_2$.2M$^+$ and M$^+$ is K$^+$. In another embodiment, X is —PO(O$^-$)$_2$.2M$^+$ and M$^+$ is N(R$^9$)$_4^+$; wherein each R$^9$ is independently H or a $C_1$-$C_4$ alkyl group. In another embodiment, X is —PO(O$^-$)$_2$.2M$^+$ and M$^+$ is N(R$^9$)$_4^+$; wherein each R$^9$ is a CH$_3$ group.

In another embodiment, the invention features a compound of formula I-E and the attendant definitions, wherein X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^+$ is Mg$^{2+}$. In another embodiment, X is —PO(O$^-$)$_2$.D$^{2+}$ and D$^{2+}$ is Ca$^{2+}$. In another embodiment, X is —PO(O$^-$)$_2$.D$^{2+}$ and D$^+$ is Ba$^{2+}$.

In another embodiment, the invention features a compound of formula I-E and the attendant definitions, wherein X is —PO(OH)$_2$.

In another embodiment, the invention provides a compound of formula I-F

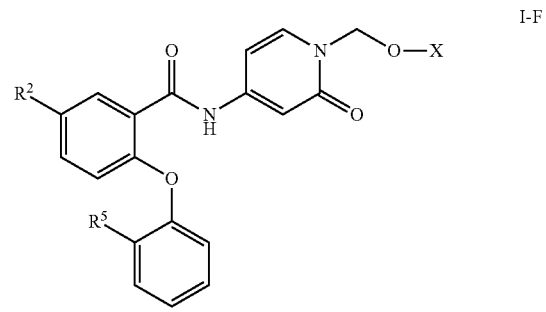

I-F wherein, independently for each occurrence:
$R^2$ is halogen, or $C_1$-$C_6$ alkyl wherein said $C_1$-$C_6$ alkyl is substituted with 0-6 halogen;
$R^5$ is halogen, OH, or $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

In another embodiment, the invention features a compound of formula I-F and the attendant definitions, wherein $R^2$ is $C_1$-$C_6$ alkyl wherein said $C_1$-$C_6$ alkyl is substituted with 0-6 halogen. In another embodiment, $R^2$ is CF$_3$.

In another embodiment, the invention features a compound of formula I-F and the attendant definitions, wherein $R^5$ is $C_1$-$C_6$ alkyl wherein said $C_1$-$C_6$ alkyl is substituted with 0-6 halogen and wherein up to two non-adjacent $CH_2$ units of said $C_1$-$C_6$ alkyl may be replaced with —O—. In one embodiment, $R^5$ is CH$_3$. In another embodiment, $R^5$ is OCF$_3$.

In another embodiment, the invention features a compound of formula I-F and the attendant definitions, wherein X is —PO(OH)$_2$, —PO(OH)O$^-$M$^+$; PO(O$^-$)$_2$.2M$^+$ or —PO(O$^-$)$_2$.D$^{2+}$; wherein M$^+$ is Li$^+$, Na$^+$ or K$^+$ and wherein D$^{2+}$ is Mg$^{2+}$ or Ca$^{2+}$.

In another embodiment, the invention features a compound of formula I-F and the attendant definitions, wherein $R^2$ is CF$_3$, $R^7$ is CH$_3$ or OCF$_3$ and X is —PO(OH)$_2$.

In another embodiment, the invention features a compound of formula I-F and the attendant definitions, wherein X is —PO(OH)O$^-$M$^+$, —PO(O$^-$)$_2$.2M$^+$; or —PO(O$^-$)$_2$.D$^{2+}$;

$M^+$ is $Li^+$, $Na^+$, $K^+$ or $N(R^9)_4^+$; wherein each $R^9$ is independently H or a $C_1$-$C_4$ alkyl group and $D^{2+}$ is $Mg^{2+}$, $Ca^{2+}$ or $Ba^{2+}$.

In another embodiment, the invention features a compound of formula I-F and the attendant definitions, wherein X is —PO(OH)O$^-$M$^+$ and M$^+$ is Li$^+$. In one embodiment, X is PO(OH)O$^-$M$^+$ and M$^+$ is Na$^+$. In another embodiment, X is —PO(OH)O$^-$M$^+$ and M$^+$ is K$^+$. In another embodiment, X is —PO(OH)O$^-$M$^+$ and M$^+$ is N(R$^9$)$_4^+$; wherein each $R^9$ is independently H or a $C_1$-$C_4$ alkyl group. In another embodiment, X is —PO(OH)O$^-$M$^+$ and M$^+$ is N(R$^9$)$_4^+$; wherein each $R^9$ is a CH$_3$ group.

In another embodiment, the invention features a compound of formula I-F and the attendant definitions, wherein X is —PO(O$^-$)$_2$.2M$^+$ and M$^+$ is Li$^+$. In one embodiment, X is —PO(O$^-$)$_2$.2M$^+$ and M$^+$ is Na$^+$. In another embodiment, X is —PO(O$^-$)$_2$.2M$^+$ and M$^+$ is K$^+$. In another embodiment, X is —PO(O$^-$)$_2$.2M$^+$ and M$^+$ is N(R$^9$)$_4^+$; wherein each $R^9$ is independently H or a $C_1$-$C_4$ alkyl group. In another embodiment, X is —PO(O$^-$)$_2$.2M$^+$ and M$^+$ is N(R$^9$)$_4^+$; wherein each $R^9$ is a CH$_3$ group.

In another embodiment, the invention features a compound of formula I-F and the attendant definitions, wherein X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$. In another embodiment, X is —PO(O$^-$)$_2$.D$^{2+}$ and D$^{2+}$ is Ba$^{2+}$.

In another embodiment, the invention features a compound of formula I-F and the attendant definitions, wherein X is —PO(OH)$_2$.

In another embodiment, the invention provides a compound of formula I-G

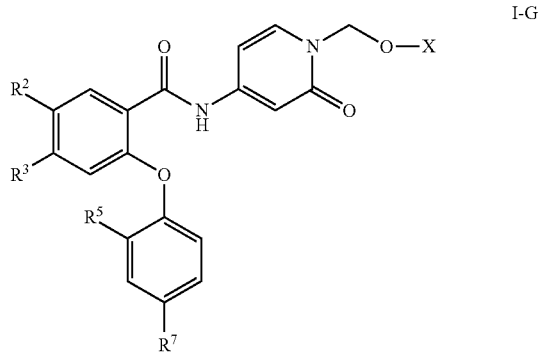

I-G wherein, independently for each occurrence:
$R^2$ and $R^3$ are independently halogen, or $C_1$-$C_6$ alkyl wherein said $C_1$-$C_6$ alkyl is substituted with 0-6 halogen;
$R^5$ is halogen, OH, or $C_1$-$C_6$ alkyl wherein said $C_1$-$C_6$ alkyl is substituted with 0-6 halogen and wherein up to two non-adjacent CH$_2$ units of said $C_1$-$C_6$ alkyl may be replaced with —O—;
$R^7$ is halogen, or $C_1$-$C_6$ alkyl wherein said $C_1$-$C_6$ alkyl is substituted with 0-6 halogen and wherein up to two non-adjacent CH$_2$ units of said $C_1$-$C_6$ alkyl may be replaced with —O—; and
X is —PO(OH)$_2$, —PO(OH)O$^-$M$^+$, —PO(O$^-$)$_2$.2M$^+$, or —PO(O$^-$)$_2$.D$^{2+}$; M$^+$ is a pharmaceutically acceptable monovalent cation; and D$^{2+}$ is a pharmaceutically acceptable divalent cation.

In another embodiment, the invention features a compound of formula I-G and the attendant definitions, wherein $R^2$ is halogen. In another embodiment, $R^2$ is Cl.

In another embodiment, the invention features a compound of formula I-G and the attendant definitions, wherein $R^3$ is halogen. In another embodiment, $R^3$ is Cl.

In another embodiment, the invention features a compound of formula I-G and the attendant definitions, wherein $R^5$ is halogen. In another embodiment, $R^5$ is Cl. In another embodiment, $R^5$ is F. In another embodiment, $R^5$ is $C_1$-$C_6$ alkyl. In another embodiment, $R^5$ is CH$_3$. In another embodiment, $R^5$ is $C_1$-$C_6$ alkyl wherein said $C_1$-$C_6$ alkyl is substituted with 0-6 halogen wherein one CH$_2$ unit of said $C_1$-$C_6$ alkyl is replaced with —O—. In another embodiment, $R^5$ is OCH$_3$. In another embodiment, $R^5$ is OH. In another embodiment, $R^5$ is OCF$_3$.

In another embodiment, the invention features a compound of formula I-G and the attendant definitions, wherein $R^7$ is halogen. In one embodiment, $R^7$ is F.

In another embodiment, the invention features a compound of formula I-G and the attendant definitions, wherein X is —PO(OH)$_2$, —PO(OH)O$^-$M$^+$; PO(O$^-$)$_2$.2M$^+$ or —PO(O$^-$)$_2$.D$^{2+}$; wherein M$^+$ is Li$^+$, Na$^+$ or K$^+$ and wherein D$^{2+}$ is Mg$^{2+}$ or Ca$^{2+}$.

In another embodiment, the invention features a compound of formula I-G and the attendant definitions, wherein $R^2$ and $R^3$ are Cl, $R^5$ is OCH$_3$ and $R^7$ is F.

In another embodiment, the invention features a compound of formula I-G and the attendant definitions, wherein $R^2$ and $R^3$ are Cl, $R^7$ is F, $R^5$ is OCH$_3$ and X is —PO(OH)$_2$.

In another embodiment, the invention features a compound of formula I-G and the attendant definitions, wherein X is —PO(OH)O$^-$M$^+$, —PO(O$^-$)$_2$.2M$^+$; or —PO(O$^-$)$_2$.D$^{2+}$; M$^+$ is Li$^+$, Na$^+$, K$^+$ or N(R$^9$)$_4^+$; wherein each $R^9$ is independently H or a $C_1$-$C_4$ alkyl group and D$^+$ is Mg$^+$, Ca$^{2+}$ or Ba$^{2+}$.

In another embodiment, the invention features a compound of formula I-G and the attendant definitions, wherein X is —PO(OH)O$^-$M$^+$ and M$^+$ is Li$^+$. In one embodiment, X is PO(OH)O$^-$M$^+$ and M$^+$ is Na$^+$. In another embodiment, X is —PO(OH)O$^-$M$^+$ and M$^+$ is K$^+$. In another embodiment, X is —PO(OH)O$^-$M$^+$ and M$^+$ is N(R$^9$)$_4^+$; wherein each $R^9$ is independently H or a $C_1$-$C_4$ alkyl group. In another embodiment, X is —PO(OH)O$^-$M$^+$ and M$^+$ is N(R$^9$)$_4^+$; wherein each $R^9$ is a CH$_3$ group.

In another embodiment, the invention features a compound of formula I-G and the attendant definitions, wherein X is —PO(O$^-$)$_2$.2M$^+$ and M$^+$ is Li$^+$. In one embodiment, X is —PO(O$^-$)$_2$.2M$^+$ and M$^+$ is Na$^+$. In another embodiment, X is —PO(O$^-$)$_2$.2M$^+$ and M$^+$ is K$^+$. In another embodiment, X is —PO(O$^-$)$_2$.2M$^+$ and M$^+$ is N(R$^9$)$_4^+$; wherein each $R^9$ is independently H or a $C_1$-$C_4$ alkyl group. In another embodiment, X is —PO(O$^-$)$_2$.2M$^+$ and M$^+$ is N(R$^9$)$_4^+$; wherein each $R^9$ is a CH$_3$ group.

In another embodiment, the invention features a compound of formula I-G and the attendant definitions, wherein X is —PO(O$^-$)$_2$.D$^{2+}$ and D$^{2+}$ is Mg$^{2+}$, Ca$^{2+}$ or Ba$^{2+}$. In one embodiment, X is —PO(O$^-$)$_2$.D$^{2+}$ and D$^{2+}$ is Mg$^{2+}$. In another embodiment, X is —PO(O$^-$)$_2$.D$^{2+}$ and D$^{2+}$ is Ca$^{2+}$. In another embodiment, X is —PO(O$^-$)$_2$.D$^{2+}$ and is Ba$^{2+}$.

In another embodiment, the invention features a compound of formula I-G and the attendant definitions, wherein X is —PO(OH)$_2$.

In another embodiment, the invention features a compound of formula I-G and the attendant definitions, wherein $R^2$ is Cl, $R^3$ is Cl, $R^5$ is OCH$_3$, $R^7$ is F and X is —PO(OH)$_2$.

In another embodiment, the invention features a compound of formula I-G and the attendant definitions, wherein $R^2$ is Cl, $R^3$ is Cl, $R^5$ is $OCH_3$, $R^7$ is F and X is —$PO(O^-)_2 \cdot 2M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention features a compound of formula I-G and the attendant definitions, wherein $R^2$ is Cl, $R^3$ is Cl, $R^5$ is $OCH_3$, $R^7$ is F and X is —PO(OH)$O^- M^+$, $M^+$ is $Li^+$, $Na^+$, $K^+$ or $N(R^9)_4^+$ wherein each $R^9$ is independently H or a $C_1$-$C_4$ alkyl group.

In another embodiment, the invention features a solid form of (4-(2-(4-fluoro-2-methylphenoxy)-4-(trifluoromethyl)benzamido)-2-oxopyridin-1 (2H)-yl)methyl dihydrogen phosphate.

In one embodiment, the present invention provides a free crystalline Form B of compound 9.

In one embodiment, the present invention provides a crystalline Form B of (4-(2-(4-fluoro-2-methylphenoxy)-4-(trifluoromethyl)benzamido)-2-oxopyridin-1 (2H)-yl) methyl dihydrogen phosphate.

In another embodiment, the present invention provides a crystalline Form B of (4-(2-(4-fluoro-2-methylphenoxy)-4-(trifluoromethyl)benzamido)-2-oxopyridin-1(2H)-yl)methyl dihydrogen phosphate which is characterized by an X-ray powder diffraction pattern (XRPD) comprising at least three approximate peak positions (degrees 2 theta±0.2) when measured using Cu $K_a$ radiation, selected from the group consisting of 4.4, 15.2, 16.4, 18.0, 19.1, 19.3, 19.9, 20.2, 20.5, 21.0, 22.2, 23.5 24.2, 24.8, 26.3, 29.6, 30.1 and 31.3, when the XRPD is collected from about 4 to about 40 degrees 2 theta (2θ).

In another embodiment, the present invention provides a crystalline Form B of (4-(2-(4-fluoro-2-methylphenoxy)-4-(trifluoromethyl)benzamido)-2-oxopyridin-1(2H)-yl)methyl dihydrogen phosphate which is characterized by an X-ray powder diffraction pattern (XRPD) comprising at least three approximate peak positions (degrees 2 theta±0.2) when measured using Cu $K_a$ radiation, selected from the group consisting of 19.3, 22.2, 23.5, 26.3 and 30.1, when the XRPD is collected from about 4 to about 40 degrees 2 theta (2θ).

Figure 2:
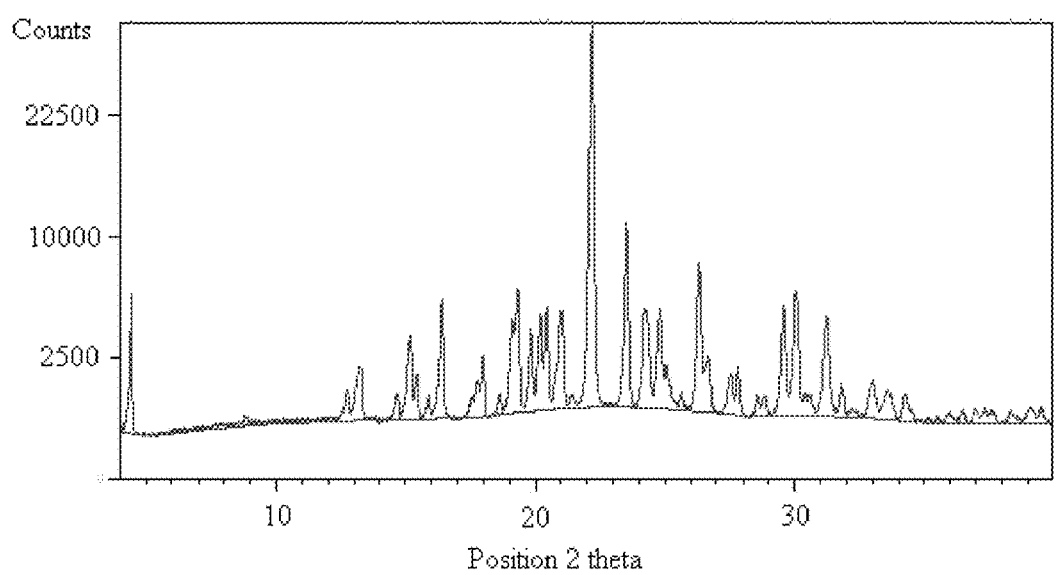
FIG. 2 shows an X-ray powder diffraction pattern of solid Form B of (4-(2-(4-fluoro-2-methylphenoxy)-4-(trifluoromethyl)benzamido)-2-oxopyridin-1(2H)-yl)methyl dihydrogen phosphate.

In another embodiment, the present invention provides a crystalline Form B of (4-(2-(4-fluoro-2-methylphenoxy)-4-(trifluoromethyl)benzamido)-2-oxopyridin-1(2H)-yl)methyl dihydrogen phosphate characterized by an X-ray powder diffraction pattern, as measured by Cu $K_a$ radiation, substantially similar to FIG. 2.

In another embodiment, the present invention provides a crystalline Form B of (4-(2-(4-fluoro-2-methylphenoxy)-4-(trifluoromethyl)benzamido)-2-oxopyridin-1(2H)-yl)methyl dihydrogen phosphate, further characterized by an endothermic peak having an onset temperature at about 210° C. degrees as measured by differential scanning calorimetry in which the temperature is scanned at about 10° C. per minute.

In another embodiment, the present invention provides a process for preparing solid Form B of compound 9.

In another embodiment, the present invention provides a process for preparing crystalline Form B of compound 9.

In one embodiment of the process, a substantially pure solid Form B of compound 9 may be prepared from amorphous or crystalline compound 9 by contacting the compound with an organic solvent, a mixture of organic solvents or a mixture of an organic solvent and water at a suitable temperature, stirring for up to 4 weeks and isolating the solid.

In another embodiment of the process, a substantially pure solid Form B of compound 9 may be prepared from amorphous or crystalline compound 9 by contacting the compound with water at a suitable temperature, stirring for up to 4 weeks and isolating the solid.

In another embodiment of the process, a substantially pure solid Form B of compound 9 may be prepared from amorphous or crystalline compound 9 by contacting the compound with an alcoholic solvent at room temperature, stirring for up to 4 weeks and isolating the solid. In another embodiment, the alcoholic solvent comprises methanol, ethanol or isopropanol.

In another embodiment of the process, a substantially pure solid Form B of compound 9 may be prepared from amorphous or crystalline compound 9 by contacting the compound with an organic ester solvent at room temperature, stirring for up to 4 weeks and isolating the solid. In one embodiment, the organic ester solvent comprises ethyl acetate or isopropyl acetate.

In another embodiment of the process, a substantially pure solid Form B of compound 9 may be prepared from amorphous or crystalline compound 9 by contacting the compound with an organic solvent at room temperature, stirring for up to 4 weeks and isolating the solid. In one embodiment, the organic solvent comprises acetonitrile, acetone, tetrahydrofuran (THF), 2-methyl tetrahydrofuran or methyl ethyl ketone.

In another embodiment, a substantially pure solid Form B of compound 9 may be prepared from amorphous or crystalline compound 9 by contacting the compound with a mixture of an organic solvent and water at room temperature, stirring for up to 4 weeks and isolating the solid. In one embodiment, the organic solvent/water mixture comprises THF/water, acetone/water or alcohol/water. In one embodiment, the alcohol of the alcohol/water mixture comprises, methanol, ethanol or isopropanol.

In another embodiment, a substantially pure solid Form B of compound 9 may be prepared from amorphous or crystalline compound 9 by contacting the compound with a mixture of an organic solvent and water at room temperature, stirring for up to 4 weeks and isolating the solid.

In another embodiment, a substantially pure solid Form B of compound 9 may be prepared from amorphous or crystalline compound 9 by contacting the compound with a mixture of an organic solvent and water at elevated temperature, stirring for up to 4 weeks and isolating the solid. In another embodiment, a substantially pure solid Form B of compound 9 may be prepared from amorphous or crystalline compound 9 by contacting the compound with a mixture of an organic solvent and water at reflux, stirring for up to 24 hours and isolating the solid. In one embodiment, the organic solvent/water mixture comprises THF/water, acetone/water or alcohol/water. In one embodiment, the organic solvent/water mixture comprises acetone/water. In another embodiment, the organic solvent/water mixture comprises THF/water.

In another embodiment, a substantially pure solid Form B of compound 9 may be prepared from amorphous or crystalline compound 9 by exposing the compound to atmospheric conditions for up to 4 weeks and isolating the solid.

In one embodiment of the process, a substantially pure crystalline Form B of compound 9 may be prepared from amorphous or crystalline compound 9 by contacting the compound with an organic solvent, a mixture of organic solvents or a mixture of an organic solvent and water at a suitable temperature, stirring for up to 4 weeks and isolating the crystalline solid.

In another embodiment of the process, a substantially pure crystalline Form B of compound 9 may be prepared from amorphous or crystalline compound 9 by contacting the compound with water at a suitable temperature, stirring for up to 4 weeks and isolating the crystalline solid.

In another embodiment of the process, a substantially pure crystalline Form B of compound 9 may be prepared from amorphous or crystalline compound 9 by contacting the compound with an alcoholic solvent at room temperature, stirring for up to 4 weeks and isolating the crystalline solid. In another embodiment, the alcoholic solvent comprises methanol, ethanol or isopropanol.

In another embodiment of the process, a substantially pure crystalline Form B of compound 9 may be prepared from amorphous or crystalline compound 9 by contacting the compound with an organic ester solvent at room temperature, stirring for up to 4 weeks and isolating the crystalline solid. In one embodiment, the organic ester solvent comprises ethyl acetate or isopropyl acetate.

In another embodiment of the process, a substantially pure crystalline Form B of compound 9 may be prepared from amorphous or crystalline compound 9 by contacting the compound with an organic solvent at room temperature, stirring for up to 4 weeks and isolating the crystalline solid. In one embodiment, the organic solvent comprises acetonitrile, acetone, tetrahydrofuran (THF), 2-methyl tetrahydrofuran or methyl ethyl ketone.

In another embodiment, a substantially pure crystalline Form B of compound 9 may be prepared from amorphous or crystalline compound 9 by contacting the compound with a mixture of an organic solvent and water at room temperature, stirring for up to 4 weeks and isolating the crystalline solid. In one embodiment, the organic solvent/water mixture comprises THF/water, acetone/water or alcohol/water. In one embodiment, the alcohol of the alcohol/water mixture comprises, methanol, ethanol or isopropanol.

In another embodiment, a substantially pure crystalline Form B of compound 9 may be prepared from amorphous or crystalline compound 9 by contacting the compound with a mixture of an organic solvent and water at room temperature, stirring for up to 4 weeks and isolating the crystalline solid.

In another embodiment, a substantially pure crystalline Form B of compound 9 may be prepared from amorphous or crystalline compound 9 by contacting the compound with a mixture of an organic solvent and water at elevated temperature, stirring for up to 4 weeks and isolating the solid. In another embodiment, a substantially pure crystalline Form B of compound 9 may be prepared from amorphous or crystalline compound 9 by contacting the compound with a mixture of an organic solvent and water at reflux, stirring for up to 24 hours and isolating the crystalline solid. In one embodiment, the organic solvent/water mixture comprises THF/water, acetone/water or alcohol/water. In one embodiment, the organic solvent/water mixture comprises acetone/water. In another embodiment, the organic solvent/water mixture comprises THF/water.

In another embodiment, a substantially pure crystalline Form B of compound 9 may be prepared from amorphous or crystalline compound 9 by exposing the compound to atmospheric conditions for up to 4 weeks and isolating the solid.

Crystalline Form B of compound 9 may be identified by a broad endotherm at about 214° C., followed by an exothermic peak at about 217° C. The endothermic peak has an onset temperature of 210° C. A person skilled in the art would recognize that the peak and onset temperatures of the endothermic and the endotherms may vary depending on the experimental conditions. Crystalline Form B of compound 9 may also be identified by an X-ray powder diffraction pattern essentially as shown in Table 1 and FIG. 2 wherein the XRPD patterns were measured using a powder diffractometer equipped with a Cu X-ray tube source. The sample was illuminated with Cu K$\alpha_1$ radiation and XRPD data were collected from about 4 to about 40° 2 theta (2θ). A person skilled in the art would recognize that relative intensities of the XPRD peaks may significantly vary depending on the orientation of the sample under test and on the type and setting of the instrument used, so that the intensities in the XPRD traces included herein are to such extent illustrative and are not intended to be used for absolute comparisons.

FIG. 2 is an X-ray powder diffraction pattern of crystalline Form B of compound 9 collected from about 4 to about 40 degrees 2θ. The peaks corresponding to the X-ray powder diffraction pattern having a relative intensity greater than or equal to 5% are listed in Table 1.

Figure 3:
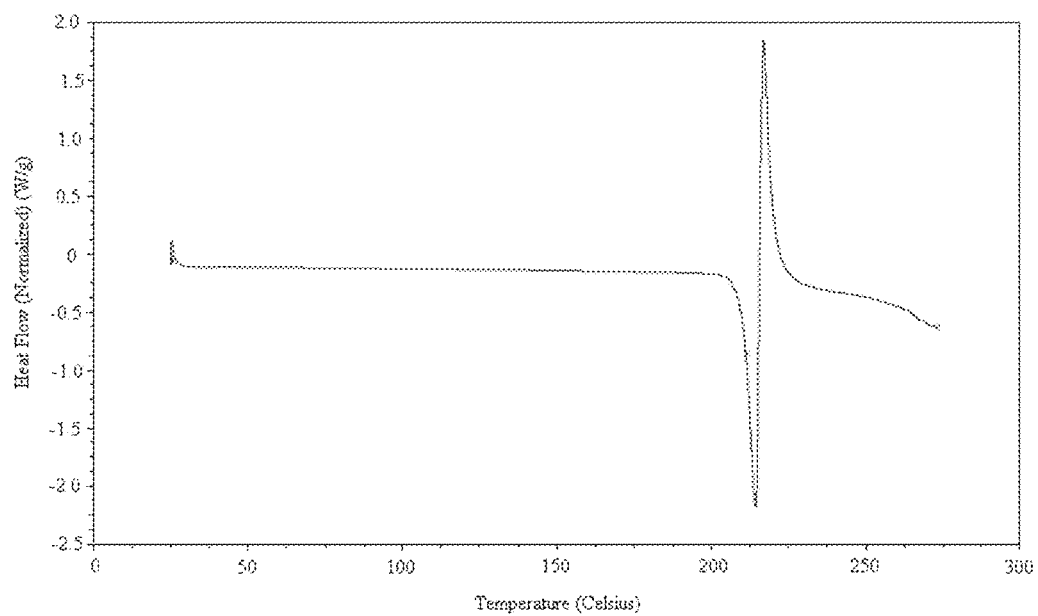
FIG. 3 shows a DSC (DifferentialScanning calorimetry) thermogram of solid Form B of (4-(2-(4-fluoro-2-methylphenoxy)-4-(trifluoromethyl)benzamido)-2-oxopyridin-1(2H)-yl)methyl dihydrogen phosphate.

FIG. 3 shows a DSC thermogram of crystalline Form B of compound 9 exhibiting a broad endothermic peak at about 214° C. followed by exothermic peak at about 217° C. The endothermic peak has an onset temperature of 210° C. A person skilled in the art would recognize that the peak and onset temperatures of the endotherms may vary depending on the experimental conditions. Data in FIG. 3 was collected as follows: a sample of approximately 1-2 mg was weighed into an aluminum pan that was crimped using lids with either one pin-hole lids. The DSC sample was scanned from 25° C. to temperatures indicated in the plots at a heating rate of 10° C./min with 50 mL/min nitrogen flow. The samples run under modulated DSC (MDSC) were modulated + and −1° C. every 60 seconds with ramp rates of 2 or 3° C./min. Data was collected and analyzed by TRIOS (TA Instruments, New Castle, Del.)

Figure 4:
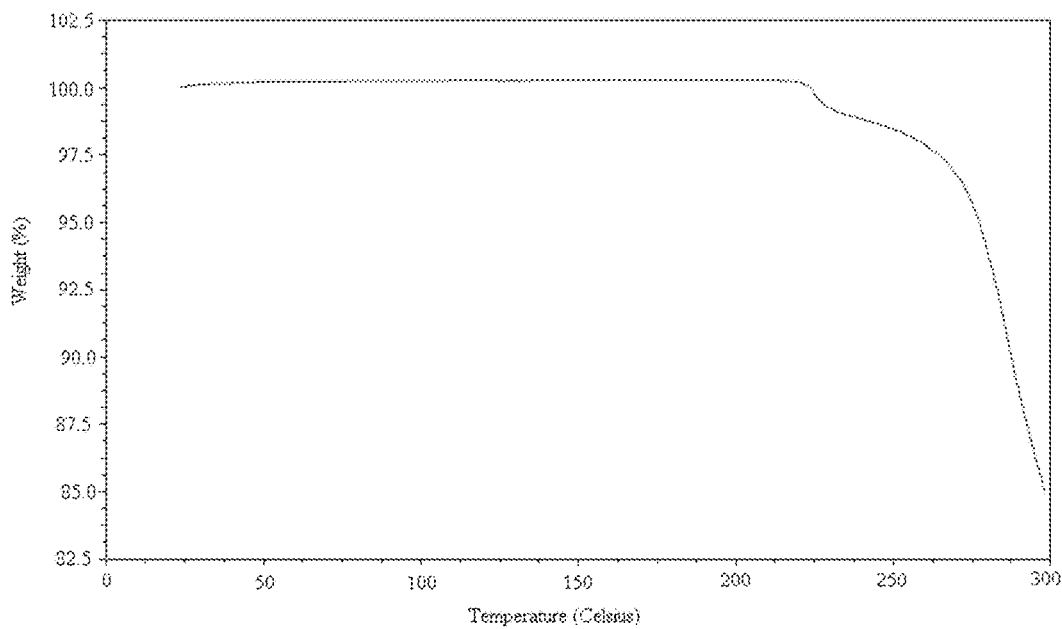
FIG. 4 shows a TGA (thermal gravimetric analysis) thermogram of solid Form B of (4-(2-(4-fluoro-2-methylphenoxy)-4-(trifluoromethyl)benzamido)-2-oxopyridin-1(2H)-yl)methyl dihydrogen phosphate.

FIG. 4 is a TGA (thermal gravimetric analysis) thermogram of crystalline Form B of compound 9 exhibiting an onset weight loss at about 218° C. and scanned from room temperature to about 300° C. at a heating rate of 10° C./min.

In one embodiment, the present invention provides a solid Form B of (4-(2-(4-fluoro-2-methylphenoxy)-4-(trifluoromethyl)benzamido)-2-oxopyridin-1(2H)-yl)methyl dihydrogen phosphate.

In one embodiment, the present invention provides a crystalline Form B of (4-(2-(4-fluoro-2-methylphenoxy)-4-(trifluoromethyl)benzamido)-2-oxopyridin-1(2H)-yl)methyl dihydrogen phosphate.

In another embodiment, the crystalline Form B of (4-(2-(4-fluoro-2-methylphenoxy)-4-(trifluoromethyl)benzamido)-2-oxopyridin-1(2H)-yl)methyl dihydrogen phosphate is characterized by an X-ray powder diffraction pattern (XPRD) comprising at least three approximate peak positions (degrees 2 theta [2θ]±0.2) when measured using Cu K$_\alpha$ radiation, selected from the group consisting of 4.4, 12.7, 13.3, 14.7, 15.2, 16.4, 18.0, 19.1, 19.3, 19.9, 20.2, 20.5, 21.0, 22.2, 23.5 24.2, 24.8, 26.3, 29.6, 30.1 and 31.3, when the XPRD is collected from about 4 to about 40 degrees 2 theta (2θ).

In another embodiment, the crystalline Form B of (4-(2-(4-fluoro-2-methylphenoxy)-4-(trifluoromethyl)benzamido)-2-oxopyridin-1(2H)-yl)methyl dihydrogen phosphate is characterized by an X-ray powder diffraction pattern (XPRD) comprising at least three approximate peak positions (degrees 2 theta±0.2) when measured using Cu $K_a$ radiation, selected from the group consisting of 4.4, 16.4, 19.3, 22.2, 23.5, 26.3, 29.6 and 30.1 when the XPRD is collected from about 4 to about 40 degrees 2θ.

In another embodiment, the crystalline Form B of (4-(2-(4-fluoro-2-methylphenoxy)-4-(trifluoromethyl)benzamido)-2-oxopyridin-1(2H)-yl)methyl dihydrogen phosphate is characterized by an X-ray powder diffraction pattern, as measured using Cu $K_\alpha$ radiation, substantially similar to FIG. 2.

In another embodiment, the crystalline Form B of (4-(2-(4-fluoro-2-methylphenoxy)-4-(trifluoromethyl)benzamido)-2-oxopyridin-1(2H)-yl)methyl dihydrogen phosphate is further characterized by an endothermic peak having an onset temperature at about 210° C. as measured by differential scanning calorimetry in which the temperature is scanned at 2-3° C. per minute.

In another embodiment, the present invention provides a method for preparing crystalline Form B of compound 9 comprising suspending a solid material of the free form in a solvent system comprising one or more organic solvents or a mixture of one or more organic solvents and water and isolating the solid.

In another embodiment, the present invention provides a process for preparing solid Form B of compound 9, comprising contacting compound 9 with water, an organic solvent, a mixture of organic solvents or a mixture of an organic solvent and water at a suitable temperature, stirring for up to 4 weeks and isolating the solid.

In another embodiment, the present invention provides a process for preparing crystalline Form B of compound 9, comprising direct crystallization from a reaction mixture with or without seeding with Form B. In one embodiment, the direct crystallization is from a final deprotection step wherein compound 20 is heated to a suitable temperature in a suitable solvent mixture with a suitable acidic reagent for a suitable period of time. In one embodiment, the suitable organic solvent mixture is water and acetonitrile, the suitable acidic reagent is acetic acid, the suitable temperature is between 50° C. and 100° C. and the suitable time is between 10 and 240 minutes.

In one embodiment, the direct crystallization process comprises treating di-tert-butyl [4-[[2-(4-fluoro-2-methylphenoxy)-4-(trifluoromethyl)benzoyl]amino]-2-oxo-1-pyridyl]methyl phosphate (123.2 g, 196 mmole) in a 3 liter flask with acetonitrile (1.23 L), acetic acid (616 ml) water (616 ml) and heating with stirring at 70° C. for 1.1 hours, then treating the mixture with a few seed crystals of Form B of 4-(2-(4-fluoro-2-methylphenoxy)-4-(trifluoromethyl) benzamido)-2-oxopyridin-1(2H)-yl)methyl dihydrogen phosphate, letting the mixture stir at 70° C. until cloudy, then turning off the heat and allowing the mixture to cool to room temperature. After stirring overnight, crystalline solids were collected by filtration and dried in a vacuum oven to constant weight to give 84.0 grams of crystalline Form B of 4-(2-(4-fluoro-2-methylphenoxy)-4-(trifluoromethyl)benzamido)-2-oxopyridin-1(2H)-yl)methyl dihydrogen phosphate.

In another embodiment, crystalline Form B is chemically and physically stable for at least one month at 5° C./dry, 40° C./dry, 25° C. with relative humidity of up to 60%; and 40° C. with relative humidity of up to 75%. In another embodiment, crystalline Form B is chemically and physically stable for at least three months in all conditions including, but not limited to open dish at 40° C., 40° C. with relative humidity of up to 75%, 25° C. with relative humidity of up to 60% and closed dish at 5° C. with a desiccator. Chemically and physically stable means no changes were observed on the X-ray powder diffraction and HPLC impurity profiles (e.g., less than 0.2% variance) and there were no observed changes in physical appearance of the samples.

TABLE 1

XRPD pattern peaks for crystalline Form B of 4-(2-(4-fluoro-2-methylphenoxy)-4-(trifluoromethyl)benzamido)-2-oxopyridin-1(2H)-yl)methyl dihydrogen phosphate

| Peak No. | Position [°2θ] | Relative Intensity [%] |
|---|---|---|
| 1 | 4.43 | 13.6 |
| 2 | 12.74 | 2.3 |
| 3 | 13.29 | 4.5 |
| 4 | 14.70 | 1.9 |
| 5 | 15.19 | 8.6 |
| 6 | 16.42 | 13.9 |
| 7 | 17.99 | 5.3 |
| 8 | 19.12 | 10.4 |
| 9 | 19.34 | 15.8 |
| 10 | 19.85 | 8.8 |
| 11 | 20.19 | 11.1 |
| 12 | 20.45 | 12.3 |
| 13 | 21.03 | 11.2 |
| 14 | 22.20 | 100.0 |
| 15 | 23.52 | 30.6 |
| 16 | 24.21 | 11.5 |
| 17 | 24.81 | 11.7 |
| 18 | 26.33 | 21.2 |
| 19 | 29.59 | 13.1 |
| 20 | 30.05 | 15.8 |
| 21 | 31.28 | 10.5 |

In one embodiment, the present invention provides an amorphous Form C of (4-(2-(4-fluoro-2-methylphenoxy)-4-(trifluoromethyl)benzamido)-2-oxopyridin-1(2H)-yl)methyl dihydrogen phosphate.

In another embodiment, the amorphous Form C of compound 9 is characterized by an X-ray powder diffraction pattern (XPRD) using Cu $K_a$ radiation, characterized by a broad halo with no discernable diffraction peak.

In yet another embodiment, the present invention provides a method for preparing amorphous Form C of compound 9 comprising spray drying a solution of compound 9 with or without co-polymer.

In one embodiment, the present application provides a process for preparing solid Form C of the compound 9. In some embodiments, the amorphous material is collected after being precipitated from a solvent or from a solution after concentrating the solution by evaporating some of the solvent, for example, using a rotator evaporator. Alternatively, adding a second solvent to the mixture may precipitate Form C.

Figure 5:
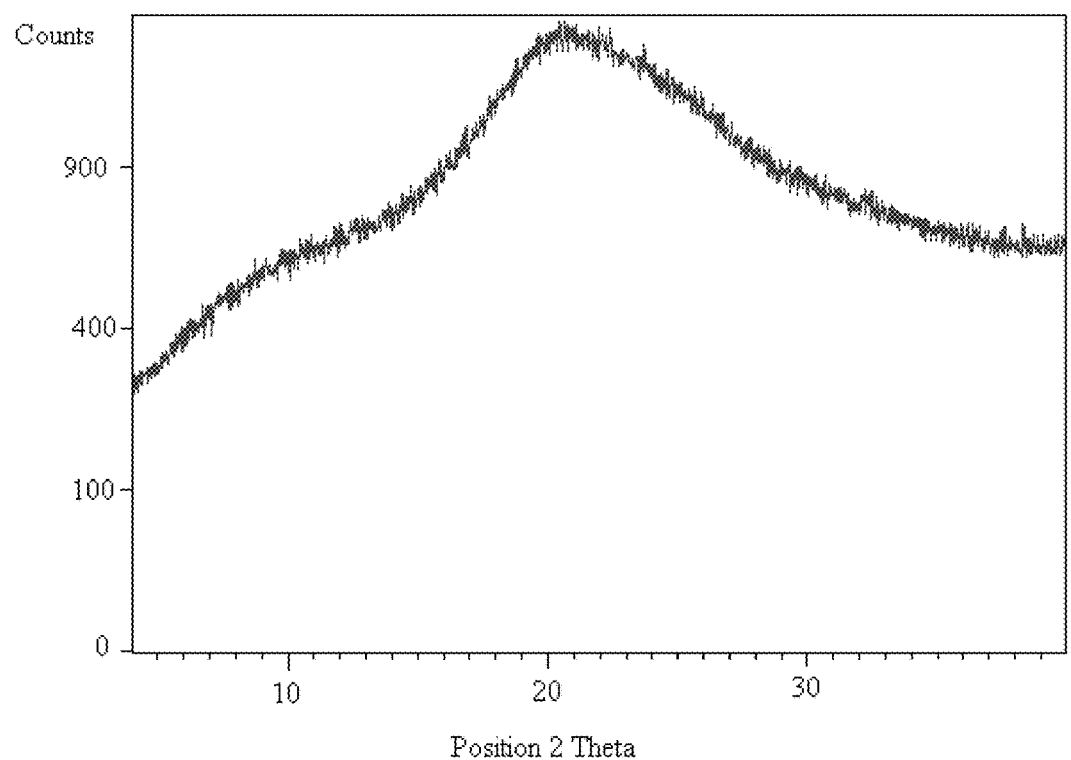
FIG. 5 shows an X-ray powder diffraction pattern of solid neat amorphous Form C of (4-(2-(4-fluoro-2-methylphenoxy)-4-(trifluoromethyl)benzamido)-2-oxopyridin-1(2H)-yl)methyl dihydrogen phosphate.

Compound 9 may be converted to amorphous solid Form C using any method known to those skilled in the art. The amorphous compound 9 may be characterized by the absence of a diffraction pattern characteristic of a crystalline form. The X-ray powder diffraction of a partially amorphous Form C may still lack features characteristic of a crystal form because the diffraction peaks from the crystalline portion of the sample may be too weak to be observable over the noise. FIG. 5 is an X-ray powder diffraction pattern of an amorphous Form X of compound 9.

In one embodiment, the amorphous Form C of compound 9 may be prepared by spray drying a solution of the compound in appropriate solvent. Spray drying is well known in the art and is often used to dry thermally-sensitive materials such as pharmaceutical drugs. Spray drying also provides consistent particle distribution that can be reproduced fairly well. Any gas may be used to dry the powder although air is commonly used. If the material is sensitive to air, an inert gas, such nitrogen or argon, may be used. Any method that converts a solution, slurry, suspension or an emulsion of the compound to produce a solid powder may be suitable for amorphous Form C of compound 9.

In one embodiment, a solution of compound 9 in a polar solvent may be spray dried using a nanospray dryer equipped a condenser. The inlet temperature may be kept between 70-120° C.

It is to be understood that crystalline Form B of compound 9 and amorphous solid Form C of compound 9, in addition to having the XRPD, DSC, TGA and other characteristics described herein, may also possess other characteristics not described, such as but not limited to the presence of water or one or more solvent molecules.

X-Ray Powder Diffraction (XRPD):

The powder x-ray diffraction measurements were performed using PANalytical's X-pert Pro diffractometer at room temperature with copper radiation (1.54060 A). The incident beam optic was comprised of a variable divergence slit to ensure a constant illuminated length on the sample and on the diffracted beam side; a fast linear solid state detector was used with an active length of 2.12 degrees 2 theta measured in a scanning mode. The powder sample was packed on the indented area of a zero background silicon holder and spinning was performed to achieve better statistics. A symmetrical scan was measured from 4-40 degrees 2 theta (2θ) with a step size of 0.017 degrees and a scan step time of 15.5 s.

Differential Scanning Calorimetry (DSC):

DSC was performed on a sample of the material using a Discovery DSC differential scanning calorimeter (TA Instruments, New Castle, Del.). The instrument was calibrated with indium. A sample of approximately 1-2 mg was weighed into an aluminum pan that was crimped using lids with either one pin-hole lids. The DSC samples were scanned from 25° C. to temperatures indicated in the plots at a heating rate of 10° C./min with 50 mL/min nitrogen flow. The samples run under modulated DSC (MDSC) were modulated + and −1° C. every 60 s with ramp rates of 2 or 3° C./min. Data was collected and analyzed by TRIOS (TA Instruments, New Castle, Del.).

Thermogravimetric Analysis (TGA):

A Model Discovery TGA, Thermogravimetric Analyzer (TA Instruments, New Castle, Del.) was used for TGA measurement. A sample with weight of approximately 2-5 mg was scanned from room temperature to temperatures indicated on the plots at a heating rate of 10° C./min. Data was collected and analyzed by TRIOS software (TA Instruments, New Castle, Del.).

Compounds names in the present invention were generated using ChemBioDrawUltra version 12.0 from Cambridge Soft/Chem Office 2010.

TABLE 2

Compound Numbers, Structures and Chemical Names

1

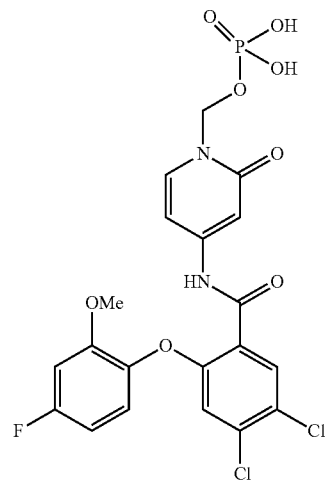

(4-(4,5-dichloro-2-(4-fluoro-2-methoxyphenoxy)benzamido)-2-oxopyridin-1(2H)-yl)methyl dihydrogen phosphate

2

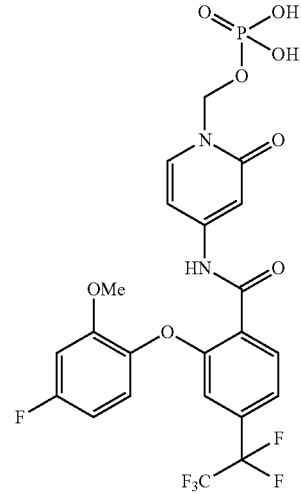

(4-(2-(4-fluoro-2-methoxyphenoxy)-4-(perfluoroethyl)benzamido)-2-oxopyridin-1(2H)-yl)methyl dihydrogen phosphate TABLE 2-continued Compound Numbers, Structures and Chemical Names

3

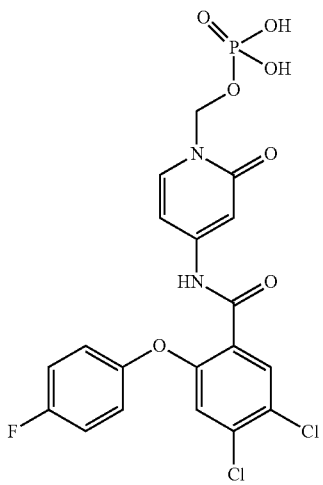

(4-(4,5-dichloro-2-(4-fluorophenoxy)benzamido)-2-oxopyridin-1(2H)-yl)methyl dihydrogen phosphate

4

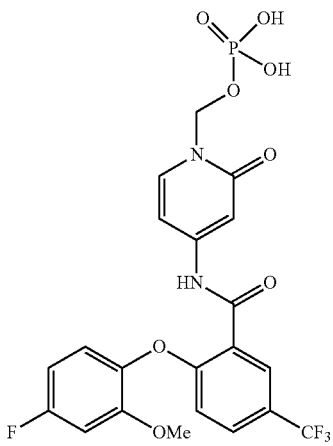

(4-(2-(4-fluoro-2-methoxyphenoxy)-5-(trifluoromethyl)benzamido)-2-oxypyridin-1(2H)-yl)methyl dihydrogen phosphate TABLE 2-continued Compound Numbers, Structures and Chemical Names

5

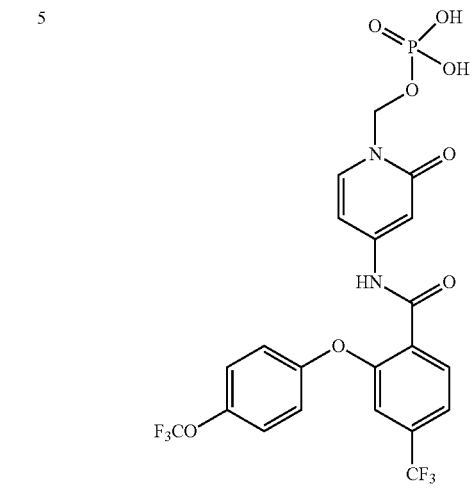

(2-oxo-4-(2-(4-(trifluoromethoxy)phenoxy)-4-(trifluoromethyl)benzamido)-pyridin-1(2H)-yl)methyl dihydrogen phosphate

6

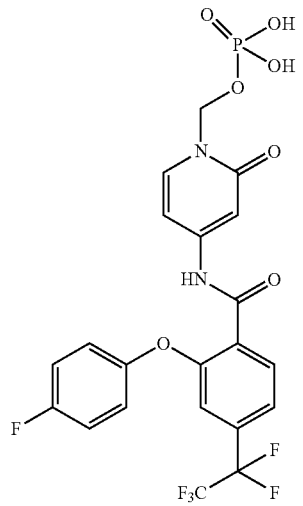

(4-(2-(4-fluorophenoxy)-4-(perfluoroethyl)benzamido)-2-oxopyridin-1(2H)-yl)methyl dihydrogen phosphate TABLE 2-continued Compound Numbers, Structures and Chemical Names

7

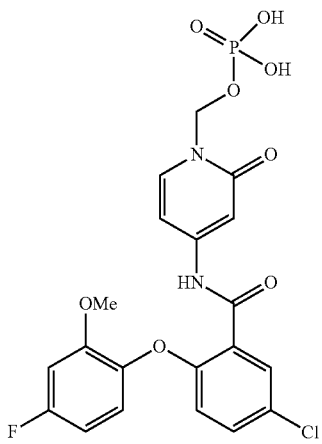

(4-(5-chloro-2-(4-fluoro-2-
methoxyphenoxy)benzamido)-
2-oxopyridin-1(2H)-yl)methyl
dihydrogen phosphate

8

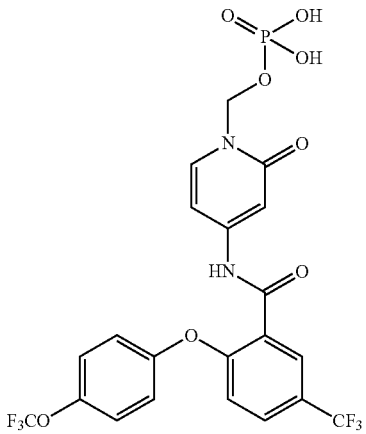

(2-oxo-4-(2-(4-(trifluoromethoxy)-
phenoxy)-5-(trifluoromethyl)-
benzamido)pyridin-1(2H)-yl)methyl
dihydrogen phosphate

9

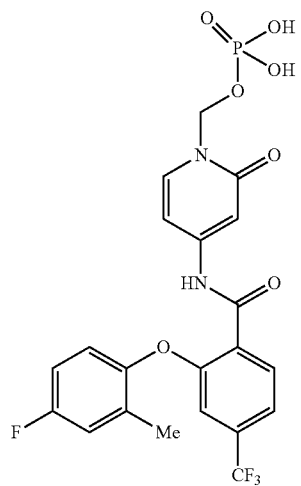

(4-(2-(4-fluoro-2-methylphenoxy)-
4-(trifluoromethyl)benzamido)-2-
oxopyridin-1(2H)-yl)methyl
dihydrogen phosphate

10

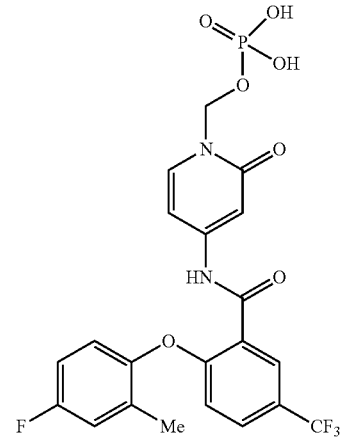

(4-(2-(4-fluoro-2-methylphenoxy)-
5-(trifluoromethyl)benzamido)-2-
oxypyridin-1(2H)-yl)methyl
dihydrogen phosphate TABLE 2-continued Compound Numbers, Structures and Chemical Names 11 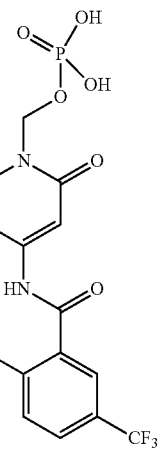

(4-(2-(2-chloro-4-fluorophenoxy)-
5-(trifluoromethyl)benzamido)-2-
oxopyridin-1(2H)-yl)methyl
dihydrogen phosphate 12 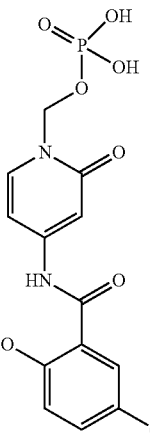

(4-(5-chloro-2-(4-fluoro-2-
methylphenoxy)benzamido)-
2-oxopyridin-1(2H)-yl)methyl
dihydrogen phosphate 13 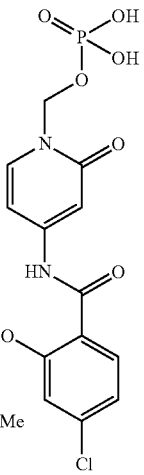

(4-(4-chloro-2-(4-fluoro-2-
methylphenoxy)benzamido)-2-
oxopyridin-1(2H)-yl)methyl
dihydrogen phosphate 14 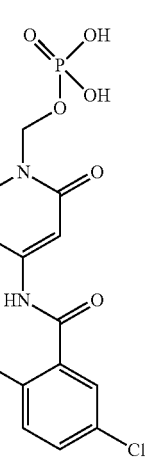

(4-(5-chloro-2-(2-chloro-4-
fluorophenoxy)benzamido)-2-
oxopyridin-1(2H)-yl)methyl
dihydrogen phosphate TABLE 2-continued Compound Numbers, Structures and Chemical Names

15

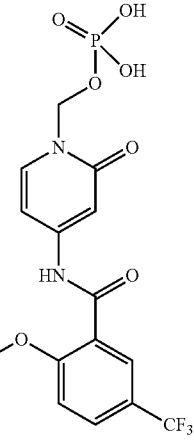

(2-oxo-4-(2-(o-tolyloxy)-5-
(trifluoromethyl)benzamido)-
pyridin-1(2H)-yl)methyl
dihydrogen phosphate

16

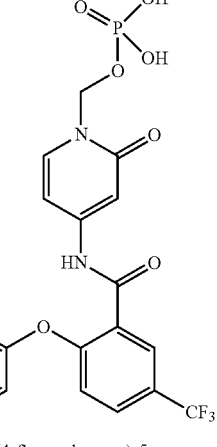

(4-(2-(2,4-difluorophenoxy)-4-
(trifluoromethyl)benzamido)-
2-oxopyridin-1(2H)-yl)methyl
dihydrogen phosphate

17

(2-oxo-4-(2-(2-
(trifluoromethoxy)phenoxy)-5-
(trifluoromethyl)benzamido)-
pyridin-1(2H)-yl)methyl
dihydrogen phosphate

18

(4-(2-(4-fluorophenoxy)-5-
(trifluoromethyl)benzamido)-
2-oxopyridin-1(2H)-yl)methyl
dihydrogen phosphate In one embodiment, the compound is (4-(4,5-dichloro-2-(4-fluoro-2-methoxyphenoxy)benzamido)-2-oxopyridin-1(2H)-yl)methyl dihydrogen phosphate or a pharmaceutically acceptable salt thereof.

In another embodiment, the compound is (4-(2-(4-fluoro-2-methoxyphenoxy)-4-(perfluoroethyl)benzamido)-2-oxopyridin-1(2H)-yl)methyl dihydrogen phosphate or a pharmaceutically acceptable salt thereof.

In another embodiment, the compound is (4-(4,5-dichloro-2-(4-fluorophenoxy)benzamido)-2-oxopyridin-1(2H)-yl)methyl dihydrogen phosphate or a pharmaceutically acceptable salt thereof.

In another embodiment, the compound is (4-(2-(4-fluoro-2-methoxyphenoxy)-5-(trifluoromethyl)benzamido)-2-oxopyridin-1(2H)-yl)methyl dihydrogen phosphate or a pharmaceutically acceptable salt thereof.

In another embodiment, the compound is (2-oxo-4-(2-(4-(trifluoromethoxy)phenoxy)-4-(trifluoromethyl)benzamido)pyridin-1(2H)-yl)methyl dihydrogen phosphate or a pharmaceutically acceptable salt thereof.

In another embodiment, the compound is (4-(2-(4-fluorophenoxy)-4-(perfluoroethyl)benzamido)-2-oxopyridin-1(2H)-yl)methyl dihydrogen phosphate or a pharmaceutically acceptable salt thereof.

In another embodiment, the compound is (4-(5-chloro-2-(4-fluoro-2-methoxyphenoxy)benzamido)-2-oxopyridin-1(2H)-yl)methyl dihydrogen phosphate or a pharmaceutically acceptable salt thereof.

In another embodiment, the compound is (2-oxo-4-(2-(4-(trifluoromethoxy)phenoxy)-5-(trifluoromethyl)benzamido)pyridin-1(2H)-yl)methyl dihydrogen phosphate or a pharmaceutically acceptable salt thereof.

In another embodiment, the compound is (4-(2-(4-fluoro-2-methylphenoxy)-4-(trifluoromethyl)benzamido)-2-oxopyridin-1(2H)-yl)methyl dihydrogen phosphate or a pharmaceutically acceptable salt thereof.

In another embodiment, the compound is (4-(2-(4-fluoro-2-methylphenoxy)-5-(trifluoromethyl)benzamido)-2-oxopyridin-1(2H)-yl)methyl dihydrogen phosphate or a pharmaceutically acceptable salt thereof.

In another embodiment, the compound is (4-(2-(2-chloro-4-fluorophenoxy)-5-(trifluoromethyl)benzamido)-2-oxopyridin-1(2H)-yl)methyl dihydrogen phosphate or a pharmaceutically acceptable salt thereof.

In another embodiment, the compound is (4-(5-chloro-2-(4-fluoro-2-methylphenoxy)benzamido)-2-oxopyridin-1(2H)-yl)methyl dihydrogen phosphate or a pharmaceutically acceptable salt thereof.

In another embodiment, the compound is (4-(4-chloro-2-(4-fluoro-2-methylphenoxy)benzamido)-2-oxopyridin-1(2H)-yl)methyl dihydrogen phosphate or a pharmaceutically acceptable salt thereof.

In another embodiment, the compound is (4-(5-chloro-2-(2-chloro-4-fluorophenoxy)benzamido)-2-oxopyridin-1(2H)-yl)methyl dihydrogen phosphate or a pharmaceutically acceptable salt thereof.

In another embodiment, the compound is (2-oxo-4-(2-(o-tolyloxy)-5-(trifluoromethyl)benzamido)pyridin-1(2H)-yl)methyl dihydrogen phosphate or a pharmaceutically acceptable salt thereof.

In another embodiment, the compound is (4-(2-(2,4-difluorophenoxy)-4-(trifluoromethyl)benzamido)-2-oxopyridin-1(2H)-yl)methyl dihydrogen phosphate or a pharmaceutically acceptable salt thereof.

In another embodiment, the compound is (2-oxo-4-(2-(2-(trifluoromethoxy)phenoxy)-5-(trifluoromethyl)benzamido)pyridin-1(2H)-yl)methyl dihydrogen phosphate or a pharmaceutically acceptable salt thereof.

In another embodiment, the compound is (4-(2-(4-fluorophenoxy)-5-(trifluoromethyl)benzamido)-2-oxopyridin-1(2H)-yl)methyl dihydrogen phosphate or a pharmaceutically acceptable salt thereof.

Compositions, Uses, Formulation, Administration and Additional Agents

Pharmaceutically Acceptable Compositions

As discussed herein, the invention provides compounds that are inhibitors of voltage-gated sodium channels, and thus the present compounds are useful for the treatment of diseases, disorders, and conditions including, but not limited to chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia. Accordingly, in another aspect of the invention, pharmaceutically acceptable compositions are provided, wherein these compositions comprise any of the compounds as described herein, and optionally comprise a pharmaceutically acceptable carrier, adjuvant or vehicle. In certain embodiments, these compositions optionally further comprise one or more additional therapeutic agents.

The term "pharmaceutically acceptable salt" refers to those salts which are, within the scope of sound medical judgement, suitable for use in contact with the tissues of humans and lower animals without undue toxicity, irritation, allergic response and the like, and are commensurate with a reasonable benefit/risk ratio. A "pharmaceutically acceptable salt" means any non-toxic salt of this invention that, upon administration to a recipient, is capable of providing, either directly or indirectly, a compound of this invention or an inhibitorily active metabolite or residue thereof. As used herein, the term "inhibitorily active metabolite or residue thereof" means that a metabolite or residue thereof is also an inhibitor of a voltage-gated sodium channel.

Pharmaceutically acceptable salts are well known in the art. For example, S. M. Berge, et al. describe pharmaceutically acceptable salts in detail in *J. Pharmaceutical Sciences,* 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Salts derived from appropriate bases include alkali metal, alkaline earth metal, ammonium and $N^+(C_{1-4}\ alkyl)_4$ salts. This invention also envisions the quaternization of any basic nitrogen-containing groups of the compounds disclosed herein. Water or oil-soluble or dispersable products may be obtained by such quaternization. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

As described herein, the pharmaceutically acceptable compositions of the invention additionally comprise a pharmaceutically acceptable carrier, adjuvant, or vehicle, which, as used herein, includes any and all solvents, diluents, or other liquid vehicle, dispersion or suspension aids, surface active agents, isotonic agents, thickening or emulsifying agents, preservatives, solid binders, lubricants and the like, as suited to the particular dosage form desired. Remington's Pharmaceutical Sciences, Sixteenth Edition, E. W. Martin (Mack Publishing Co., Easton, Pa., 1980) discloses various carriers used in formulating pharmaceutically acceptable compositions and known techniques for the preparation thereof. Except insofar as any conventional carrier medium is incompatible with the compounds of the invention, such as by producing any undesirable biological effect or otherwise interacting in a deleterious manner with any other component(s) of the pharmaceutically acceptable composition, its use is contemplated to be within the scope of this invention. Some examples of materials which can serve as pharmaceutically acceptable carriers include, but are not limited to, ion exchangers, alumina, aluminum stearate, lecithin, serum proteins, such as human serum albumin, buffer substances such as phosphates, glycine, sorbic acid, or potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol or polyethylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

In another aspect, the invention features a pharmaceutical composition comprising the compound of the invention and a pharmaceutically acceptable carrier.

In another aspect, the invention features a pharmaceutical composition comprising a therapeutically effective amount of the compounds of formula I and one or more pharmaceutically acceptable carriers or vehicles.

Uses of Compounds and Pharmaceutically Acceptable Compositions

In another aspect, the invention features a method of inhibiting a voltage-gated sodium channel in a subject comprising administering to the subject a compound of formula I or a pharmaceutical composition thereof. In another aspect, the voltage-gated sodium channel is NaV1.8.

In yet another aspect, the invention features a method of treating or lessening the severity in a subject of chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia comprising administering an effective amount of a compound to the subject, or a pharmaceutical composition of the compound of formula I.

In yet another aspect, the invention features a method of treating or lessening the severity in a subject of gut pain, wherein gut pain comprises inflammatory bowel disease pain, Crohn's disease pain or interstitial cystitis pain wherein said method comprises administering an effective amount of a compound, or a pharmaceutical composition of the compound of formula I.

In yet another aspect, the invention features a method of treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain; nerve avulsion injury, brachial plexus avulsion injury, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic cephalalgia wherein said method comprises administering an effective amount of a compound, or a pharmaceutical composition of the compound of formula I.

In yet another aspect, the invention features a method of treating or lessening the severity in a subject of musculoskeletal pain, wherein musculoskeletal pain comprises osteoarthritis pain, back pain, cold pain, burn pain or dental pain wherein said method comprises administering an effective amount of a compound, or a pharmaceutical composition of the compound of formula I.

In yet another aspect, the invention features a method of treating or lessening the severity in a subject of inflammatory pain, wherein inflammatory pain comprises rheumatoid arthritis pain or vulvodynia wherein said method comprises administering an effective amount of a compound, or a pharmaceutical composition of the compound of formula I.

In yet another aspect, the invention features a method of treating or lessening the severity in a subject of inflammatory pain, wherein inflammatory pain comprises rheumatoid arthritis pain wherein said method comprises administering an effective amount of a compound, or a pharmaceutical composition of the compound of formula I.

In yet another aspect, the invention features a method of treating or lessening the severity in a subject of idiopathic pain, wherein idiopathic pain comprises fibromyalgia pain wherein said method comprises administering an effective amount of a compound, or a pharmaceutical composition of the compound of formula I.

In yet another aspect, the invention features a method of treating or lessening the severity in a subject of pathological cough wherein said method comprises administering an effective amount of a compound, or a pharmaceutical composition of the compound of formula I.

In yet another aspect, the invention features a method wherein the subject is treated with one or more additional therapeutic agents administered concurrently with, prior to, or subsequent to treatment with an effective amount of a compound, or a pharmaceutical composition of the compound of formula I.

In another aspect, the invention features a method of inhibiting a voltage-gated sodium channel in a subject comprising administering to the subject an effective amount of a compound, or a pharmaceutical composition of the compound of formula I. In another aspect, the voltage-gated sodium channel is $Na_V1.8$.

In another aspect, the invention features a method of inhibiting a voltage-gated sodium channel in a biological sample comprising contacting the biological sample with an effective amount of a compound, or a pharmaceutical composition of the compound of formula I. In another aspect, the voltage-gated sodium channel is $Na_V1.8$.

In another aspect, the invention features a method of treating or lessening the severity in a subject of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain, cancer pain, stroke, cerebral ischemia, traumatic brain injury, amyotrophic lateral sclerosis, stress induced angina, exercise induced angina, palpitations, hypertension, or abnormal gastro-intestinal motility, comprising administering an effective amount of a compound, or a pharmaceutical composition of the compound of formula I.

In another aspect, the invention features a method of treating or lessening the severity in a subject of femur cancer pain, non-malignant chronic bone pain, rheumatoid arthritis, osteoarthritis, spinal stenosis, neuropathic low back pain, myofascial pain syndrome; fibromyalgia, temporomandibular joint pain, chronic visceral pain, abdominal pain, pancreatic pain, IBS pain, chronic and acute headache pain; migraine, tension headache, cluster headaches, chronic and acute neuropathic pain, post-herpetic neuralgia, diabetic neuropathy, HIV-associated neuropathy, trigeminal neuralgia, Charcot-Marie Tooth neuropathy, hereditary sensory neuropathy, peripheral nerve injury, painful neuromas, ectopic proximal and distal discharges; radiculopathy, chemotherapy induced neuropathic pain, radiotherapy-induced neuropathic pain, post-mastectomy pain, central pain, spinal cord injury pain, post-stroke pain, thalamic pain, complex regional pain syndrome, phantom pain, intractable pain, acute pain, acute post-operative pain, acute musculoskeletal pain, joint pain, mechanical low back pain, neck pain, tendonitis, injury pain, exercise pain, acute visceral pain, pyelonephritis, appendicitis, cholecystitis, intestinal obstruction, hernias, chest pain, cardiac pain; pelvic pain, renal colic pain, acute obstetric pain, labor pain; cesarean section pain, acute inflammatory pain, burn pain, trauma pain, acute intermittent pain, endometriosis, acute herpes zoster pain, sickle cell anemia, acute pancreatitis, breakthrough pain, orofacial pain, sinusitis pain, dental pain, multiple sclerosis (MS) pain, pain in depression, leprosy pain, Behcet's disease pain, adiposis dolorosa, phlebitic pain, Guillain-Barre pain, painful legs and moving toes; Haglund syndrome, erythromelalgia pain, Fabry's disease pain, bladder and urogenital disease, urinary incontinence, pathological cough, hyperactivebladder, painful bladder syndrome, interstitial cyctitis (IC), prostatitis, complex regional pain syndrome (CRPS) type I, complex regional pain syndrome (CRPS), type II, widespread pain, paroxysmal extreme pain, pruritis, tinnitus, or angina-induced pain, comprising administering an effective amount of a compound, or a pharmaceutical composition of the compound of formula I.

In another aspect, the invention features a method of treating or lessening the severity in a subject of neuropathic pain comprising administering an effective amount of a compound, or a pharmaceutical composition of the compound of formula I. In one aspect, the neuropathic pain is selected from post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic cephalalgia.

Manufacture of Medicaments

In one aspect, the invention provides the use of a compound or pharmaceutical composition of formula I for the manufacture of a medicament for use in inhibiting a voltage-gated sodium channel. In another aspect, the voltage-gated sodium channel is $Na_v1.8$.

In yet another aspect, the invention provides the use of a compound or pharmaceutical composition of formula I for the manufacture of a medicament for use in treating or lessening the severity in a subject of chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia.

In yet another aspect, the invention provides the use of a compound or pharmaceutical composition of formula I for the manufacture of a medicament for use in treating or lessening the severity in a subject of gut pain, wherein gut pain comprises inflammatory bowel disease pain, Crohn's disease pain or interstitial cystitis pain.

In yet another aspect, the invention provides the use of a compound or pharmaceutical composition of formula I for the manufacture of a medicament for use in a treating or lessening the severity in a subject of neuropathic pain, wherein neuropathic pain comprises post-herpetic neuralgia, diabetic neuralgia, painful HIV-associated sensory neuropathy, trigeminal neuralgia, burning mouth syndrome, post-amputation pain, phantom pain, painful neuroma; traumatic neuroma, Morton's neuroma, nerve entrapment injury, spinal stenosis, carpal tunnel syndrome, radicular pain, sciatica pain, nerve avulsion injury, brachial plexus avulsion injury, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic neuropathy.

In yet another aspect, the invention provides the use of a compound or pharmaceutical composition of formula I for the manufacture of a medicament for use in treating or lessening the severity in a subject of musculoskeletal pain, wherein musculoskeletal pain comprises osteoarthritis pain, back pain, cold pain, burn pain or dental pain.

In yet another aspect, the invention the invention provides the use of a compound or pharmaceutical composition of formula I for the manufacture of a medicament for use in treating or lessening the severity in a subject of inflammatory pain, wherein inflammatory pain comprises rheumatoid arthritis pain or vulvodynia.

In yet another aspect, the invention the invention provides the use of a compound or pharmaceutical composition of formula I for the manufacture of a medicament for use in treating or lessening the severity in a subject of inflammatory pain, wherein inflammatory pain comprises rheumatoid arthritis pain.

In yet another aspect, the invention provides the use of a compound or pharmaceutical composition of formula I for the manufacture of a medicament for use in treating or lessening the severity in a subject of idiopathic pain, wherein idiopathic pain comprises fibromyalgia pain.

In yet another aspect, the invention provides the use of a compound or pharmaceutical composition of formula I for the manufacture of a medicament for use in treating or lessening the severity in a subject of pathological cough.

In yet another aspect, the invention provides the use of a compound or pharmaceutical composition of formula I for the manufacture of a medicament in combination with one or more additional therapeutic agents administered concurrently with, prior to, or subsequent to treatment with the compound or pharmaceutical composition.

In another aspect, the invention provides the use of a compound or pharmaceutical composition of formula I for the manufacture of a medicament for use in treating or lessening the severity of acute pain, chronic pain, neuropathic pain, inflammatory pain, arthritis, migraine, cluster headaches, trigeminal neuralgia, herpetic neuralgia, general neuralgias, epilepsy, epilepsy conditions, neurodegenerative disorders, psychiatric disorders, anxiety, depression, dipolar disorder, myotonia, arrhythmia, movement disorders, neuroendocrine disorders, ataxia, multiple sclerosis, irritable bowel syndrome, incontinence, pathological cough, visceral pain, osteoarthritis pain, postherpetic neuralgia, diabetic neuropathy, radicular pain, sciatica, back pain, head pain, neck pain, severe pain, intractable pain, nociceptive pain, breakthrough pain, postsurgical pain, cancer pain, stroke, cerebral ischemia, traumatic brain injury, amyotrophic lateral sclerosis, stress induced angina, exercise induced angina, palpitations, hypertension, or abnormal gastro-intestinal motility.

In another aspect, the invention provides the use of a compound or pharmaceutical composition of formula I for the manufacture of a medicament for use in treating or lessening the severity of femur cancer pain, non-malignant chronic bone pain, rheumatoid arthritis, osteoarthritis, spinal stenosis, neuropathic low back pain, myofascial pain syndrome, fibromyalgia, temporomandibular joint pain, chronic visceral pain, abdominal pain, pancreatic pain, IBS pain, chronic and acute headache pain, migraine, tension headache, cluster headaches, chronic and acute neuropathic pain, post-herpetic neuralgia, diabetic neuropathy, HIV-associated neuralgia, trigeminal neuralgia, Charcot-Marie Tooth neuropathy, hereditary sensory neuropathy, peripheral nerve injury, painful neuromas, ectopic proximal and distal discharges, radiculopathy, chemotherapy induced neuropathic pain, radiotherapy-induced neuropathic pain, post-mastectomy pain, central pain, spinal cord injury pain, post-stroke pain, thalamic pain, complex regional pain syndrome, phantom pain, intractable pain, acute pain, acute post-operative pain, acute musculoskeletal pain, joint pain, mechanical low back pain, neck pain, tendonitis, injury pain, exercise pain, acute visceral pain, pyelonephritis, appendicitis, cholecystitis, intestinal obstruction, hernias, chest pain, cardiac pain, pelvic pain, renal colic pain, acute obstetric pain, labor pain, cesarean section pain, acute inflammatory pain, burn pain, trauma pain, acute intermittent pain, endometriosis, acute herpes zoster pain, sickle cell anemia, acute pancreatitis, breakthrough pain, orofacial pain, sinusitis pain, dental pain, multiple sclerosis (MS) pain, pain in depression, leprosy pain, Behcet's disease pain, adiposis dolorosa, phlebitic pain, Guillain-Barre pain, painful legs and moving toes, Haglund syndrome, erythromelalgia pain, Fabry's disease pain, bladder and urogenital disease, urinary incontinence, pathological cough, hyperactive bladder, painful bladder syndrome, interstitial cyctitis (IC), prostatitis, complex regional pain syndrome (CRPS) type I complex regional pain syndrome (CRPS) type II, widespread pain, paroxysmal extreme pain, pruritis, tinnitis, or angina-induced pain.

In another aspect, the invention provides the use of a compound or pharmaceutical composition of formula I for the manufacture of a medicament for use in treating or lessening the severity of neuropathic pain. In one aspect, the neuropathic pain is selected from post-herpetic neuralgia, diabetic neuralgia, painful HIV-associated sensory neuropathy, trigeminal neuralgia, burning mouth syndrome, post-amputation pain, phantom pain, painful neuroma, traumatic neuroma, Morton's neuroma, nerve entrapment injury, spinal stenosis, carpal tunnel syndrome, radicular pain, sciatica pain, nerve avulsion injury, brachial plexus avulsion, complex regional pain syndrome, drug therapy induced neuralgia, cancer chemotherapy induced neuralgia, anti-retroviral therapy induced neuralgia, post spinal cord injury pain, idiopathic small-fiber neuropathy, idiopathic sensory neuropathy or trigeminal autonomic cephalalgia.

Administration of Pharmaceutically Acceptable Compositions.

In certain embodiments of the invention an "effective amount" of the compound, or pharmaceutically acceptable composition is that amount effective for treating or lessening the severity of one or more of chronic pain, gut pain, neuropathic pain, musculoskeletal pain, acute pain, inflammatory pain, cancer pain, idiopathic pain, multiple sclerosis, Charcot-Marie-Tooth syndrome, incontinence, pathological cough, or cardiac arrhythmia.

The compounds and compositions, according to the methods of the present invention, may be administered using any amount and any route of administration effective for treating or lessening the severity of one or more of the pain or non-pain diseases recited herein. The exact amount required will vary from subject to subject, depending on the species, age, and general condition of the subject, the severity of the infection, the particular agent, its mode of administration, and the like. The compounds of the invention are preferably formulated in dosage unit form for ease of administration and uniformity of dosage. The expression "dosage unit form" as used herein refers to a physically discrete unit of agent appropriate for the subject to be treated. It will be understood, however, that the total daily usage of the compounds and compositions of the invention will be decided by the attending physician within the scope of sound medical judgment. The specific effective dose level for any particular subject or organism will depend upon a variety of factors including the disorder being treated and the severity of the disorder; the activity of the specific compound employed; the specific composition employed; the age, body weight, general health, sex and diet of the subject; the time of administration, route of administration, and rate of excretion of the specific compound employed; the duration of the treatment; drugs used in combination or coincidental with the specific compound employed, and like factors well known in the medical arts. The term "subject" or "patient," as used herein, means an animal, preferably a mammal, and most preferably a human.

The pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in microencapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, eardrops, and eye drops are also contemplated as being within the scope of this invention. Additionally, the invention contemplates the use of transdermal patches, which have the added advantage of providing controlled delivery of a compound to the body. Such dosage forms are prepared by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

As described generally above, the compounds of the invention are useful as inhibitors of voltage-gated sodium channels. In one embodiment, the compounds and compositions of the invention are inhibitors of $Na_V1.8$ and thus, without wishing to be bound by any particular theory, the compounds and compositions are particularly useful for treating or lessening the severity of a disease, condition, or disorder where activation or hyperactivity of $Na_V1.8$ is implicated in the disease, condition, or disorder. When activation or hyperactivity of $Na_V1.8$ is implicated in a particular disease, condition, or disorder, the disease, condition, or disorder may also be referred to as a "$Na_V1.8$-mediated disease, condition or disorder." Accordingly, in another aspect, the invention provides a method for treating or lessening the severity of a disease, condition, or disorder where activation or hyperactivity of $Na_V1.8$ is implicated in the disease state.

The activity of a compound utilized in this invention as an inhibitor of $Na_V1.8$ may be assayed according to methods described generally in the Examples herein, or according to methods available to one of ordinary skill in the art.

Additional Therapeutic Agents

It will also be appreciated that the compounds and pharmaceutically acceptable compositions of the invention can be employed in combination therapies, that is, the compounds and pharmaceutically acceptable compositions can be administered concurrently with, prior to, or subsequent to, one or more other desired therapeutics or medical procedures. The particular combination of therapies (therapeutics or procedures) to employ in a combination regimen will take into account compatibility of the desired therapeutics and/or procedures and the desired therapeutic effect to be achieved. It will also be appreciated that the therapies employed may achieve a desired effect for the same disorder (for example, an inventive compound may be administered concurrently with another agent used to treat the same disorder), or they may achieve different effects (e.g., control of any adverse effects). As used herein, additional therapeutic agents that are normally administered to treat or prevent a particular disease, or condition, are known as "appropriate for the disease, or condition, being treated." For example, exemplary additional therapeutic agents include, but are not limited to: nonopioid analgesics (indoles such as Etodolac, Indomethacin, Sulindac, Tolmetin; naphthylalkanones such sa Nabumetone; oxicams such as Piroxicam; para-aminophenol derivatives, such as Acetaminophen; propionic acids such as Fenoprofen, Flurbiprofen, Ibuprofen, Ketoprofen, Naproxen, Naproxen sodium, Oxaprozin; salicylates such as Asprin, Choline magnesium trisalicylate, Diflunisal; fenamates such as meclofenamic acid, Mefenamic acid; and pyrazoles such as Phenylbutazone); or opioid (narcotic) agonists (such as Codeine, Fentanyl, Hydromorphone, Levorphanol, Meperidine, Methadone, Morphine, Oxycodone, Oxymorphone, Propoxyphene, Buprenorphine, Butorphanol, Dezocine, Nalbuphine, and Pentazocine). Additionally, nondrug analgesic approaches may be utilized in conjunction with administration of one or more compounds of the invention. For example, anesthesiologic (intraspinal infusion, neural blocade), neurosurgical (neurolysis of CNS pathways), neurostimulatory (transcutaneous electrical nerve stimulation, dorsal column stimulation), physiatric (physical therapy, orthotic devices, diathermy), or psychologic (cognitive methods-hypnosis, biofeedback, or behavioral methods) approaches may also be utilized. Additional appropriate therapeutic agents or approaches are described generally in The Merck Manual, Nineteenth Edition, Ed. Robert S. Porter and Justin L. Kaplan, Merck Sharp & Dohme Corp., a subsidiary of Merck & Co., Inc., 2011, and the Food and Drug Administration website, www.fda.gov, the entire contents of which are hereby incorporated by reference.

In another embodiment, additional appropriate therapeutic agents are selected from the following:

(1) an opioid analgesic, e.g. morphine, heroin, hydromorphone, oxymorphone, levorphanol, levallorphan, methadone, meperidine, fentanyl, cocaine, codeine, dihydrocodeine, oxycodone, hydrocodone, propoxyphene, nalmefene, nalorphine, naloxone, naltrexone, buprenorphine, butorphanol, nalbuphine or pentazocine;

(2) a nonsteroidal antiinflammatory drug (NSAID), e.g. aspirin, diclofenac, diflusinal, etodolac, fenbufen, fenoprofen, flufenisal, flurbiprofen, ibuprofen, indomethacin, ketoprofen, ketorolac, meclofenamic acid, mefenamic acid, meloxicam, nabumetone, naproxen, nimesulide, nitroflurbiprofen, olsalazine, oxaprozin, phenylbutazone, piroxicam, sulfasalazine, sulindac, tolmetin or zomepirac;

(3) a barbiturate sedative, e.g. amobarbital, aprobarbital, butabarbital, butabital, mephobarbital, metharbital, methohexital, pentobarbital, phenobartital, secobarbital, talbutal, theamylal or thiopental;

(4) a benzodiazepine having a sedative action, e.g. chlordiazepoxide, clorazepate, diazepam, flurazepam, lorazepam, oxazepam, temazepam or triazolam;

(5) a histamine ($H_1$) antagonist having a sedative action, e.g. diphenhydramine, pyrilamine, promethazine, chlorpheniramine or chlorcyclizine;

(6) a sedative such as glutethimide, meprobamate, methaqualone or dichloralphenazone;

(7) a skeletal muscle relaxant, e.g. baclofen, carisoprodol, chlorzoxazone, cyclobenzaprine, methocarbamol or orphrenadine;

(8) an NMDA receptor antagonist, e.g. dextromethorphan ((+)-3-hydroxy-N-methylmorphinan) or its metabolite dextrorphan ((+)-3-hydroxy-N-methylmorphinan), ketamine, memantine, pyrroloquinoline quinine, cis-4-(phosphonomethyl)-2-piperidinecarboxylic acid, budipine, EN-3231 (MorphiDex®), a combination formulation of morphine and dextromethorphan), topiramate, neramexane or perzinfotel including an NR2B antagonist, e.g. ifenprodil, traxoprodil or (−)—(R)-6-{2-[4-(3-fluorophenyl)-4-hydroxy-1-piperidinyl]-1-hydroxyethyl-3,4-dihydro-2(1H)-quinolinone;

(9) an alpha-adrenergic, e.g. doxazosin, tamsulosin, clonidine, guanfacine, dexmetatomidine, modafinil, or 4-amino-6,7-dimethoxy-2-(5-methane-sulfonamido-1,2,3,4-tetrahydroisoquinol-2-yl)-5-(2-pyridyl) quinazoline;

(10) a tricyclic antidepressant, e.g. desipramine, imipramine, amitriptyline or nortriptyline;

(11) an anticonvulsant, e.g. carbamazepine (Tegretol®), lamotrigine, topiramate, lacosamide (Vimpat®) or valproate;

(12) a tachykinin (NK) antagonist, particularly an NK-3, NK-2 or NK-1 antagonist, e.g. (alphaR,9R)-7-[3,5-bis(trifluoromethyl)benzyl]-8,9,10,11-tetrahydro-9-methyl-5-(4-methylphenyl)-7H-[1,4]diazocino[2,1-g][1,7]-naphthyridine-6-13-dione (TAK-637), 5-[[(2R,3S)-2-[(1R)-1-[3,5-bis(trifluoromethyl)phenyl]ethoxy-3-(4-fluorophenyl)-4-morpholinyl]-methyl]-1,2-dihydro-3H-1,2,4-triazol-3-one (MK-869), aprepitant, lanepitant, dapitant or 3-[[2-methoxy-5-(trifluoromethoxy)phenyl]-methylamino]-2-phenylpiperidine (2S,3S);

(13) a muscarinic antagonist, e.g oxybutynin, tolterodine, propiverine, tropsium chloride, darifenacin, solifenacin, temiverine and ipratropium;

(14) a COX-2 selective inhibitor, e.g. celecoxib, rofecoxib, parecoxib, valdecoxib, deracoxib, etoricoxib, or lumiracoxib;

(15) a coal-tar analgesic, in particular paracetamol;

(16) a neuroleptic such as droperidol, chlorpromazine, haloperidol, perphenazine, thioridazine, mesoridazine, trifluoperazine, fluphenazine, clozapine, olanzapine, risperidone, ziprasidone, quetiapine, sertindole, aripiprazole, sonepiprazole, blonanserin, iloperidone, perospirone, raclopride, zotepine, bifeprunox, asenapine, lurasidone, amisulpride, balaperidone, palindore, eplivanserin, osanetant, rimonabant, meclinertant, Miraxion® or sarizotan;

(17) a vanilloid receptor agonist (e.g. resinferatoxin or civamide) or antagonist (e.g. capsazepine, GRC-15300);

(18) a beta-adrenergic such as propranolol;

(19) a local anaesthetic such as mexiletine;

(20) a corticosteroid such as dexamethasone;

(21) a 5-HT receptor agonist or antagonist, particularly a 5-$HT_{1B/1D}$ agonist such as eletriptan, sumatriptan, naratriptan, zolmitriptan or rizatriptan;

(22) a 5-$HT_{2A}$ receptor antagonist such as R(+)-alpha-(2,3-dimethoxy-phenyl)-1-[2-(4-fluorophenylethyl)]-4-piperidinemethanol (MDL-100907);

(23) a cholinergic (nicotinic) analgesic, such as ispronicline (TC-1734), (E)-N-methyl-4-(3-pyridinyl)-3-buten-1-amine (RJR-2403), (R)-5-(2-azetidinylmethoxy)-2-chloropyridine (ABT-594) or nicotine;

(24) Tramadol®, Tramadol ER (Ultram ER®), Tapentadol ER (Nucynta®);

(25) a PDE5 inhibitor, such as 5-[2-ethoxy-5-(4-methyl-1-piperazinyl-sulphonyl)phenyl]-1-methyl-3-n-propyl-1,6-dihydro-7H-pyrazolo[4,3-d]pyrimidin-7-one (sildenafil), (6R,12aR)-2,3,6,7,12,12a-hexahydro-2-methyl-6-(3,4-methylenedioxyphenyl)-pyrazino[2',1':6,1]-pyrido[3,4-b]indole-1,4-dione (IC-351 or tadalafil), 2-[2-ethoxy-5-(4-ethylpiperazin-1-yl-1-sulphonyl)-phenyl]-5-methyl-7-propyl-3H-imidazo[5,1-f][1,2,4]triazin-4-one (vardenafil), 5-(5-acetyl-2-butoxy-3-pyridinyl)-3-ethyl-2-(1-ethyl-3-azetidinyl)-2,6-dihydro-7H-pyrazolo[4,3-d]pyrimidin-7-one, 5-(5-acetyl-2-propoxy-3-pyridinyl)-3-ethyl-2-(1-isopropyl-3-azetidinyl)-2,6-dihydro-7H-pyrazolo[4,3-d]pyrimidin-7-one, 5-[2-ethoxy-5-(4-ethylpiperazin-1-ylsulphonyl)pyridin-3-yl]-3-ethyl-2-[2-methoxyethyl]-2,6-dihydro-7H-pyrazolo[4,3-d]pyrimidin-7-one, 4-[(3-chloro-4-methoxybenzyl)amino]-2-[(2S)-2-(hydroxymethyl)pyrrolidin-1-yl]-N-(pyrimidin-2-ylmethyl)pyrimidine-5-carboxamide, 3-(1-methyl-7-oxo-3-propyl-6,7-dihydro-1H-pyrazolo[4,3-d]pyrimidin-5-yl)-N-[2-(1-methylpyrrolidin-2-yl)ethyl]-4-propoxybenzenesulfonamide;

(26) an alpha-2-delta ligand such as gabapentin (Neurontin®), gabapentin GR (Gralise®), gabapentin, enacarbil (Horizant®), pregabalin (Lyrica®), 3-methyl gabapentin, (1[alpha],3[alpha],5[alpha])(3-amino-methyl-bicyclo[3.2.0]hept-3-yl)-acetic acid, (3S,5R)-3-aminomethyl-5-methylheptanoic acid, (3S,5R)-3-amino-5-methyl-heptanoic acid, (3S,5R)-3-amino-5-methyl-octanoic acid, (2S,4S)-4-(3-chlorophenoxy)proline, (2S,4S)-4-(3-fluorobenzyl)-proline, [(1R,5R,6S)-6-(aminomethyl)bicyclo[3.2.0]hept-6-yl]acetic acid, 3-(1-aminomethyl-cyclohexylmethyl)-4H-[1,2,4]oxadiazol-5-one, C-[1-(1H-tetrazol-5-ylmethyl)-cycloheptyl]-methylamine, (3S,4S)-(1-aminomethyl-3,4-dimethyl-cyclopentyl)-acetic acid, (3S,5R)-3-aminomethyl-5-methyl-octanoic acid, (3S,5R)-3-amino-5-methyl-nonanoic acid, (3S,5R)-3-amino-5-methyl-octanoic acid, (3R,4R,5R)-3-amino-4,5-dimethyl-heptanoic acid and (3R,4R,5R)-3-amino-4,5-dimethyl-octanoic acid;

(27) a cannabinoid such as KHK-6188;

(28) metabotropic glutamate subtype 1 receptor (mGluR1) antagonist;

(29) a serotonin reuptake inhibitor such as sertraline, sertraline metabolite demethylsertraline, fluoxetine, norfluoxetine (fluoxetine desmethyl metabolite), fluvoxamine, paroxetine, citalopram, citalopram metabolite desmethylcitalopram, escitalopram, d,l-fenfluramine, femoxetine, ifoxetine, cyanodothiepin, litoxetine, dapoxetine, nefazodone, cericlamine and trazodone;

(30) a noradrenaline (norepinephrine) reuptake inhibitor, such as maprotiline, lofepramine, mirtazepine, oxaprotiline, fezolamine, tomoxetine, mianserin, buprorion, buprorion metabolite hydroxybuproprion, nomifensine and viloxazine (Vivalan®), especially a selective noradrenaline reuptake inhibitor such as reboxetine, in particular (S,S)-reboxetine;

(31) a dual serotonin-noradrenaline reuptake inhibitor, such as venlafaxine, venlafaxine metabolite O-desmethyl-venlafaxine, clomipramine, clomipramine metabolite desmethylclomipramine, duloxetine (Cymbalta®), milnacipran and imipramine;

(32) an inducible nitric oxide synthase (iNOS) inhibitor such as S-[2-[(1-iminoethyl)amino]ethyl]-L-homocysteine, S-[2-[(1-iminoethyl)-amino]ethyl]-4,4-dioxo-L-cysteine, S-[2-[(1-iminoethyl)amino]ethyl]-2-methyl-L-cysteine, (2S,5Z)-2-amino-2-methyl-7-[(1-iminoethyl)amino]-5-heptenoic acid, 2-[[(1R,3S)-3-amino-4-hydroxy-1-(5-thiazolyl)-butyl]thio]-S-chloro-S-pyridinecarbonitrile; 2-[[(1R,3S)-3-amino-4-hydroxy-1-(5-thiazolyl)butyl]thio]-4-chlorobenzonitrile, (2S,4R)-2-amino-4-[[2-chloro-5-(trifluoromethyl)phenyl]thio]-5-thiazolebutanol, 2-[[(1R,3S)-3-amino-4-hydroxy-1-(5-thiazolyl)butyl]thio]-6-(trifluoromethyl)-3-pyridinecarbonitrile, 2-[[(1R,3S)-3-amino-4-hydroxy-1-(5-thiazolyl)butyl]thio]-5-chlorobenzonitrile, N-[4-[2-(3-chlorobenzylamino)ethyl]phenyl]thiophene-2-carboxamidine, NXN-462, or guanidinoethyldisulfide;

(33) an acetylcholinesterase inhibitor such as donepezil;

(34) a prostaglandin E2 subtype 4 (EP4) antagonist such as N-[({2-[4-(2-ethyl-4,6-dimethyl-1H-imidazo[4,5-c]pyridin-1-yl)phenyl]ethyl}amino)-carbonyl]-4-methylbenzenesulfonamide or 4-[(15)-1-({[5-chloro-2-(3-fluorophenoxy)pyridin-3-yl]carbonyl}amino)ethyl]benzoic acid;

(35) a leukotriene B4 antagonist; such as 1-(3-biphenyl-4-ylmethyl-4-hydroxy-chroman-7-yl)-cyclopentanecarboxylic acid (CP-105696), 5-[2-(2-Carboxyethyl)-3-[6-(4-methoxyphenyl)-5E-hexenyl]oxyphenoxy]-valeric acid (ONO-4057) or DPC-11870;

(36) a 5-lipoxygenase inhibitor, such as zileuton, 6-[(3-fluoro-5-[4-methoxy-3,4,5,6-tetrahydro-2H-pyran-4-yl])phenoxy-methyl]-1-methyl-2-quinolone (ZD-2138), or 2,3,5-trimethyl-6-(3-pyridylmethyl)-1,4-benzoquinone (CV-6504);

(37) a sodium channel blocker, such as lidocaine, lidocaine plus tetracaine cream (ZRS-201) or eslicarbazepine acetate;

(38) an $Na_V1.7$ blocker, such as XEN-402, XEN403, TV-45070, PF-05089771, CNV1014802, GDC-0276, RG7893 and such as those disclosed in WO2011/140425; WO2012/106499; WO2012/112743; WO2012/125613, WO2012/116440, WO2011026240, U.S. Pat. Nos. 8,883,840, 8,466,188, or PCT/US2013/21535 the entire contents of each application hereby incorporated by reference.

(38a) an $Na_V1.7$ blocker such as (2-benzylspiro[3,4-dihydropyrrolo[1,2-a]pyrazine-1,4'-piperidine]-1'-yl)-(4-isopropoxy-3-methyl-phenyl)methanone, 2,2,2-trifluoro-1-[1'-[3-methoxy-4-[2-(trifluoromethoxy)ethoxy]benzoyl]-2,4-dimethyl-spiro[3,4-dihydropyrrolo[1,2-a]pyrazine-1,4'-piperidine]-6-yl]ethanone, [8-fluoro-2-methyl-6-(trifluoromethyl)spiro[3,4-dihydropyrrolo[1,2-a]pyrazine-1,4'-piperidine]-1'-yl]-(4-isobutoxy-3-methoxy-phenyl)methanone, 1-(4-benzhydrylpiperazin-1-yl)-3-[2-(3,4-dimethylphenoxy)ethoxy]propan-2-ol, (4-butoxy-3-methoxy-phenyl)-[2-methyl-6-(trifluoromethyl)spiro[3,4-dihydropyrrolo[1,2-a]pyrazine-1,4'-piperidine]-1'-yl]methanone, [8-fluoro-2-methyl-6-(trifluoromethyl)spiro[3,4-dihydropyrrolo[1,2-a]pyrazine-1,4'-piperidine]-1'-yl]-(5-isopropoxy-6-methyl-2-pyridyl)methanone, (4-isopropoxy-3-methyl-phenyl)-[2-methyl-6-(1,1,2,2,2-pentafluoroethyl)spiro[3,4-dihydropyrrolo[1,2-a]pyrazine-1,4'-piperidine]-1'-yl]methanone, 5-[2-methyl-4-[2-methyl-6-(2,2,2-trifluoroacetyl)spiro[3,4-dihydropyrrolo[1,2-a]pyrazine-1,4'-piperidine]-1'-carbonyl]phenyl]pyridine-2-carbonitrile, (4-isopropoxy-3-methyl-phenyl)-[6-(trifluoromethyl)spiro[3,4-dihydro-2H-pyrrolo[1,2-a]pyrazine-1,4'-piperidine]-1'-yl]methanone, 2,2,2-trifluoro-1-[1'-[3-methoxy-4-[2-(trifluoromethoxy)ethoxy]benzoyl]-2-methyl-spiro[3,4-dihydropyrrolo[1,2-a]pyrazine-1,4'-piperidine]-6-yl]ethanone, 2,2,2-trifluoro-1-[1'-(5-isopropoxy-6-methyl-pyridine-2-carbonyl)-3,3-dimethyl-spiro[2,4-dihydropyrrolo[1,2-a]pyrazine-1,4'-piperidine]-6-yl]ethanone, 2,2,2-trifluoro-1-[1'-(5-isopentyloxypyridine-2-carbonyl)-2-methyl-spiro[3,4-dihydropyrrolo[1,2-a]pyrazine-1,4'-piperidine]-6-yl]ethanone, (4-isopropoxy-3-methoxy-phenyl)-[2-methyl-6-(trifluoromethyl)spiro[3,4-dihydropyrrolo[1,2-a]pyrazine-1,4'-piperidine]-1'-yl]methanone, 2,2,2-trifluoro-1-[1'-(5-isopentyloxypyridine-2-carbonyl)-2,4-dimethyl-spiro[3,4-dihydropyrrolo[1,2-a]pyrazine-1,4'-piperidine]-6-yl]ethanone, 1-[(3S)-2,3-dimethyl-1'-[4-(3,3,3-trifluoropropoxymethyl)benzoyl]spiro[3,4-dihydropyrrolo[1,2-a]pyrazine-1,4'-piperidine]-6-yl]-2,2,2-trifluoro-ethanone, [8-fluoro-2-methyl-6-(trifluoromethyl)spiro[3,4-dihydropyrrolo[1,2-a]pyrazine-1,4'-piperidine]-1'-yl]-[3-methoxy-4-[(1R)-1-methylpropoxy]phenyl]methanone, 2,2,2-trifluoro-1-[1'-(5-isopropoxy-6-methyl-pyridine-2-carbonyl)-2,4-dimethyl-spiro[3,4-dihydropyrrolo[1,2-a]pyrazine-1,4'-piperidine]-6-yl]ethanone, 1-[1'-[4-methoxy-3-(trifluoromethyl)benzoyl]-2-methyl-spiro[3,4-dihydropyrrolo[1,2-a]pyrazine-1,4'-piperidine]-6-yl]-2,2-dimethyl-propan-1-one, (4-isopropoxy-3-methyl-phenyl)-[2-methyl-6-(trifluoromethyl)spiro[3,4-dihydropyrrolo[1,2-a]pyrazine-1,4'-piperidine]-1'-yl]methanone, [2-methyl-6-(1-methylcyclopropanecarbonyl)spiro[3,4-dihydropyrrolo[1,2-a]pyrazine-1,4'-piperidine]-1'-yl]-[4-(3,3,3-trifluoropropoxymethyl)phenyl]methanone, 4-bromo-N-(4-bromophenyl)-3-[(1-methyl-2-oxo-4-piperidyl)sulfamoyl]benzamide or (3-chloro-4-isopropoxy-phenyl)-[2-methyl-6-(1,1,2,2,2-pentafluoroethyl)spiro[3,4-dihydropyrrolo[1,2-a]pyrazine-1,4'-piperidine]-1'-yl]methanone.

(39) an $Na_V1.8$ blocker, such as PF-04531083, PF-06372865 and such as those disclosed in WO2008/135826, WO2006/011050, WO2013/061205, US20130303535, WO2013131018, U.S. Pat. No. 8,466,188, WO2013114250, WO2014/1280808, WO2014/120815 and WO2014/120820, the entire contents of each application hereby incorporated by reference.

(39a) an $Na_V1.8$ blocker such as 4,5-dichloro-2-(4-fluoro-2-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-4-(perfluoroethyl)benzamide, 4,5-dichloro-2-(4-fluorophenoxy)-N-(2-oxo-1,2-dihydropyridin-4-yl)benzamide, 4,5-dichloro-2-(3-fluoro-4-methoxyphenoxy)-N-(2-oxo-1,2-dihydropyridin-4-yl)benzamide, 2-(4-fluoro-2-methoxyphenoxy)-N-(2-oxo-1,2-dihydropyridin-4-yl)-5-(trifluoromethyl)benzamide, N-(2-oxo-1,2-dihydropyridin-4-yl)-2-(4-(trifluoromethoxy)phenoxy)-4-(trifluoromethyl)benzamide, 2-(4-fluorophenoxy)-N-(2-oxo-1,2-dihydropyridin-4-yl)-4-(perfluoroethyl)benzamide, 5-chloro-2-(4-fluoro-2-methoxyphenoxy)-N-(2-oxo-1,2-dihydropyridin-4-yl)benzamide, N-(2-oxo-1,2-dihydropyridin-4-yl)-2-(4-(trifluoromethoxy)phenoxy)-5-(trifluoromethyl)benzamide, 2-(4-fluoro-2-methylphenoxy)-N-(2-oxo-1,2-dihydropyridin-4-yl)-5-(trifluoromethyl)benzamide, 2-(2-chloro-4-fluorophenoxy)-N-(2-oxo-1,2-dihydropyridin-4-yl)-5-(trifluoromethyl)benzamide, 5-chloro-2-(4-fluoro-2-methylphenoxy)-N-(2-oxo-1,2-dihydropyridin-4-yl)benzamide, 4-chloro-2-(4-fluoro-2-methylphenoxy)-N-(2-oxo-1,2-dihydropyridin-4-yl)benzamide, 5-chloro-2-(2-chloro-4-fluorophenoxy)-N-(2-oxo-1,2-dihydropyridin-4-yl)benzamide, 2-((5-fluoro-2-hydroxybenzyl)oxy)-N-(2-oxo-1,2-dihydropyridin-4-yl)-4-(trifluoromethyl)benzamide, N-(2-oxo-1,2-dihydropyridin-4-yl)-2-(o-tolyloxy)-5-(trifluoromethyl)benzamide, 2-(2,4-difluorophenoxy)-N-(2-oxo-1,2-dihydropyridin-4-yl)-4-(trifluoromethyl)benzamide, N-(2-oxo-1,2-dihydropyridin-4-yl)-2-(2-(trifluoromethoxy)phenoxy)-5-(trifluoromethyl)benzamide, 2-(4-fluorophenoxy)-N-(2-oxo-1,2-dihydropyridin-4-yl)-5-(trifluoromethyl)benzamide, In one embodiment, the compound is 3-(4-fluoro-2-methoxyphenoxy)-N-(3-(methylsulfonyl)phenyl)quinoxaline-2-carboxamide, 3-(2-chloro-4-fluorophenoxy)-N-(3-sulfamoylphenyl)quinoxaline-2-carboxamide, 3-(2-chloro-4-methoxyphenoxy)-N-(3-sulfamoylphenyl)quinoxaline-2-carboxamide, 3-(4-chloro-2-methoxyphenoxy)-N-(3-sulfamoylphenyl)quinoxaline-2-carboxamide, 4-(3-(4-(trifluoromethoxy)phenoxy)quinoxaline-2-carboxamido)picolinic acid, 2-(2,4-difluorophenoxy)-N-(3-sulfamoylphenyl)quinoline-3-carboxamide, 2-(4-fluoro-2-methoxyphenoxy)-N-(3-sulfamoylphenyl)quinoline-3-carboxamide, 3-(2,4-difluorophenoxy)-N-(3-sulfamoylphenyl)quinoxaline-2-carboxamide, N-(3-sulfamoylphenyl)-2-(4-(trifluoromethoxy)phenoxy)quinoline-3-carboxamide, N-(3-sulfamoylphenyl)-3-(4-(trifluoromethoxy)phenoxy)quinoxaline-2-carboxamide, 3-(4-chloro-2-methylphenoxy)-N-(3-sulfamoylphenyl)quinoxaline-2-carboxamide, 5-(3-(4-(trifluoromethoxy)phenoxy)quinoxaline-2-carboxamido)picolinic acid, 3-(4-fluoro-2-methoxyphenoxy)-N-(2-oxo-2,3-dihydro-1H-benzo[d]imidazol-5-yl)quinoxaline-2-carboxamide, 3-(4-fluoro-2-methoxyphenoxy)-N-(pyridin-4-yl)quinoxaline-2-carboxamide, 3-(4-fluorophenoxy)-N-(3-sulfamoylphenyl)quinoxaline-2-carboxamide, N-(3-cyanophenyl)-3-(4-fluoro-2-methoxyphenoxy)quinoxaline-2-carboxamide, N-(4-carbamoylphenyl)-3-(4-fluoro-2-methoxyphenoxy)quinoxaline-2-carboxamide, 4-(3-(4-(trifluoromethoxy)phenoxy)quinoxaline-2-carboxamido)benzoic acid, N-(4-cyanophenyl)-3-(4-fluoro-2-methoxyphenoxy)quinoxaline-2-carboxamide, 5-(4,5-dichloro-2-(4-fluoro-2-methoxyphenoxy)benzamido)picolinic acid, 5-(2-(2,4-dimethoxyphenoxy)-4,6-bis(trifluoromethyl)benzamido)picolinic acid, 4-(4,5-dichloro-2-(4-fluoro-2-methoxyphenoxy)benzamido)benzoic acid, 5-(2-(4-fluoro-2-methoxyphenoxy)-4,6-bis(trifluoromethyl)benzamido)picolinic acid, 4-(2-(4-fluoro-2-methoxyphenoxy)-4-(perfluoroethyl)benzamido)benzoic acid, 5-(2-(4-fluoro-2-methoxyphenoxy)-4-(perfluoroethyl)benzamido)picolinic acid, 4-(2-(4-fluoro-2-methylphenoxy)-4-(trifluoromethyl)

benzamido)benzoic acid, 5-(4,5-dichloro-2-(4-fluoro-2-methoxyphenoxy)benzamido)picolinic acid, 4-(2-(2-chloro-4-fluorophenoxy)-4-(perfluoroethyl)benzamido)benzoic acid, 4-(2-(4-fluoro-2-methylphenoxy)-4-(perfluoroethyl)benzamido)benzoic acid, 4-(4,5-dichloro-2-(4-(trifluoromethoxy)phenoxy)benzamido)benzoic acid, 4-(4,5-dichloro-2-(4-chloro-2-methylphenoxy)benzamido)benzoic acid, 5-(4-(tert-butyl)-2-(4-fluoro-2-methoxyphenoxy)benzamido)picolinic acid, 5-(4,5-dichloro-2-(4-(trifluoromethoxy)phenoxy)benzamido)picolinic acid, 4-(4,5-dichloro-2-(4-fluoro-2-methylphenoxy)benzamido)benzoic acid, 5-(4,5-dichloro-2-(2,4-dimethoxyphenoxy)benzamido)picolinic acid, 5-(4,5-dichloro-2-(2-chloro-4-fluorophenoxy)benzamido)picolinic acid, 5-(4,5-dichloro-2-(4-fluoro-2-methylphenoxy)benzamido)picolinic acid, 4-(4,5-dichloro-2-(4-chloro-2-methoxyphenoxy)benzamido) benzoic acid, 5-(4,5-dichloro-2-(2,4-difluorophenoxy) benzamido)picolinic acid, 2-(4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-5-(trifluoromethyl)benzamide, 2-(4-fluorophenoxy)-N-(3-sulfamoylphenyl)-4-(trifluoromethyl) benzamide, 2-(2-chloro-4-fluorophenoxy)-N-(3-sulfamoylphenyl)-6-(trifluoromethyl)benzamide, 2-(2-chloro-4-fluorophenoxy)-5-(difluoromethyl)-N-(3-sulfamoylphenyl)benzamide, 2-(4-fluorophenoxy)-4-(perfluoroethyl)-N-(3-sulfamoylphenyl)benzamide, 2-(4-chloro-2-methoxyphenoxy)-4-(perfluoroethyl)-N-(3-sulfamoylphenyl)benzamide, 2-(4-fluoro-2-methoxyphenoxy)-N-(3-sulfamoylphenyl)-5-(trifluoromethyl)benzamide, 5-chloro-2-(4-fluoro-2-methylphenoxy)-N-(3-sulfamoylphenyl)benzamide, 4,5-dichloro-2-(4-fluoro-2-methoxyphenoxy)-N-(3-sulfamoylphenyl)benzamide, 2,4-dichloro-6-(4-chloro-2-methoxyphenoxy)-N-(3-sulfamoylphenyl)benzamide, 2,4-dichloro-6-(4-fluoro-2-methylphenoxy)-N-(3-sulfamoylphenyl)benzamide, 2-(4-fluoro-2-methoxyphenoxy)-N-(3-sulfamoylphenyl)-4,6-bis (trifluoromethyl)benzamide, 2-(4-fluoro-2-methylphenoxy)-N-(3-sulfamoylphenyl)-4,6-bis(trifluoromethyl)benzamide, 5-chloro-2-(2-chloro-4-fluorophenoxy)-N-(3-sulfamoylphenyl)benzamide, 2-(4-fluoro-2-methoxyphenoxy)-N-(3-sulfamoylphenyl)-4-(trifluoromethoxy)benzamide, 2-(4-fluoro-2-methoxyphenoxy)-N-(3-sulfamoylphenyl)-4-(trifluoromethyl)benzamide, 4,5-dichloro-2-(4-fluorophenoxy)-N-(3-sulfamoylphenyl)benzamide, 2-(4-fluoro-2-methoxyphenoxy)-4-(perfluoroethyl)-N-(3-sulfamoylphenyl)benzamide, 5-fluoro-2-(4-fluoro-2-methylphenoxy)-N-(3-sulfamoylphenyl)benzamide, 2-(2-chloro-4-fluorophenoxy)-4-cyano-N-(3-sulfamoylphenyl) benzamide or N-(3-sulfamoylphenyl)-2-(4-(trifluoromethoxy)phenoxy)-4-(trifluoromethyl)benzamide.

(40) a combined $Na_v1.7$ and $Na_v1.8$ blocker, such as DSP-2230 or BL-1021;

(41) a 5-HT3 antagonist, such as ondansetron;

(42) a TPRV 1 receptor agonist, such as capsaicin (NeurogesX®, Qutenza®); and the pharmaceutically acceptable salts and solvates thereof;

(43) a nicotinic receptor antagonist, such as varenicline;

(44) an N-type calcium channel antagonist, such as Z-160;

(45) a nerve growth factor antagonist, such as tanezumab;

(46) an endopeptidase stimulant, such as senrebotase;

(47) an angiotensin II antagonist, such as EMA-401;

In one embodiment, the additional appropriate therapeutic agents are selected from V-116517, Pregbalin, controlled release Pregbalin, Ezogabine (Potiga®), Ketamine/amitriptyline topical cream (Amiket®), AVP-923, Perampanel (E-2007), Ralfinamide, transdermal bupivacaine (Eladur®), CNV1014802, JNJ-10234094 (Carisbamate), BMS-954561 or ARC-4558.

In another embodiment, the additional appropriate therapeutic agents are selected from N-(6-amino-5-(2,3,5-trichlorophenyl)pyridin-2-yl)acetamide; N-(6-amino-5-(2-chloro-5-methoxyphenyl)pyridin-2-yl)-1-methyl-1H-pyrazole-5-carboxamide; or 3-((4-(4-(trifluoromethoxy)phenyl)-1H-imidazol-2-yl)methyl)oxetan-3-amine.

The amount of additional therapeutic agent present in the compositions of this invention will be no more than the amount that would normally be administered in a composition comprising that therapeutic agent as the only active agent. The amount of additional therapeutic agent in the presently disclosed compositions will range from about 10% to 100% of the amount normally present in a composition comprising that agent as the only therapeutically active agent.

The compounds of this invention or pharmaceutically acceptable compositions thereof may also be incorporated into compositions for coating an implantable medical device, such as prostheses, artificial valves, vascular grafts, stents and catheters. Accordingly, the invention, in another aspect, includes a composition for coating an implantable device comprising a compound of the invention as described generally above, and in classes and subclasses herein, and a carrier suitable for coating said implantable device. In still another aspect, the invention includes an implantable device coated with a composition comprising a compound of the invention as described generally above, and in classes and subclasses herein, and a carrier suitable for coating said implantable device. Suitable coatings and the general preparation of coated implantable devices are described in U.S. Pat. Nos. 6,099,562; 5,886,026; and 5,304,121. The coatings are typically biocompatible polymeric materials such as a hydrogel polymer, polymethyldisiloxane, polycaprolactone, polyethylene glycol, polylactic acid, ethylene vinyl acetate, and mixtures thereof. The coatings may optionally be further covered by a suitable topcoat of fluorosilicone, polysaccarides, polyethylene glycol, phospholipids or combinations thereof to impart controlled release characteristics in the composition.

Another aspect of the invention relates to inhibiting $Na_v1.8$ activity in a subject, which method comprises administering to the subject a compound of formula I or a composition comprising said compound. Yet another aspect of the invention relates to inhibiting $Na_v1.8$ activity in a biological sample, which method comprises contacting said biological sample with a compound of formula I or a composition comprising said compound. The term "biological sample," as used herein, includes, without limitation, cell cultures or extracts thereof; biopsied material obtained from a mammal or extracts thereof; and blood, saliva, urine, feces, semen, tears, or other body fluids or extracts thereof.

Inhibition of $Na_v1.8$ activity in a biological sample is useful for a variety of purposes that are known to one of skill in the art. Examples of such purposes include, but are not limited to, the study of sodium channels in biological and pathological phenomena; and the comparative evaluation of new sodium channel inhibitors.

SCHEMES AND EXAMPLES

The compounds of the invention may be prepared readily using the following methods. Illustrated below in Scheme 1 is a general method for preparing the compounds of the present invention.

Scheme 1: Preparation of Compounds of Formula I, where X is P(O)(OH)$_2$:

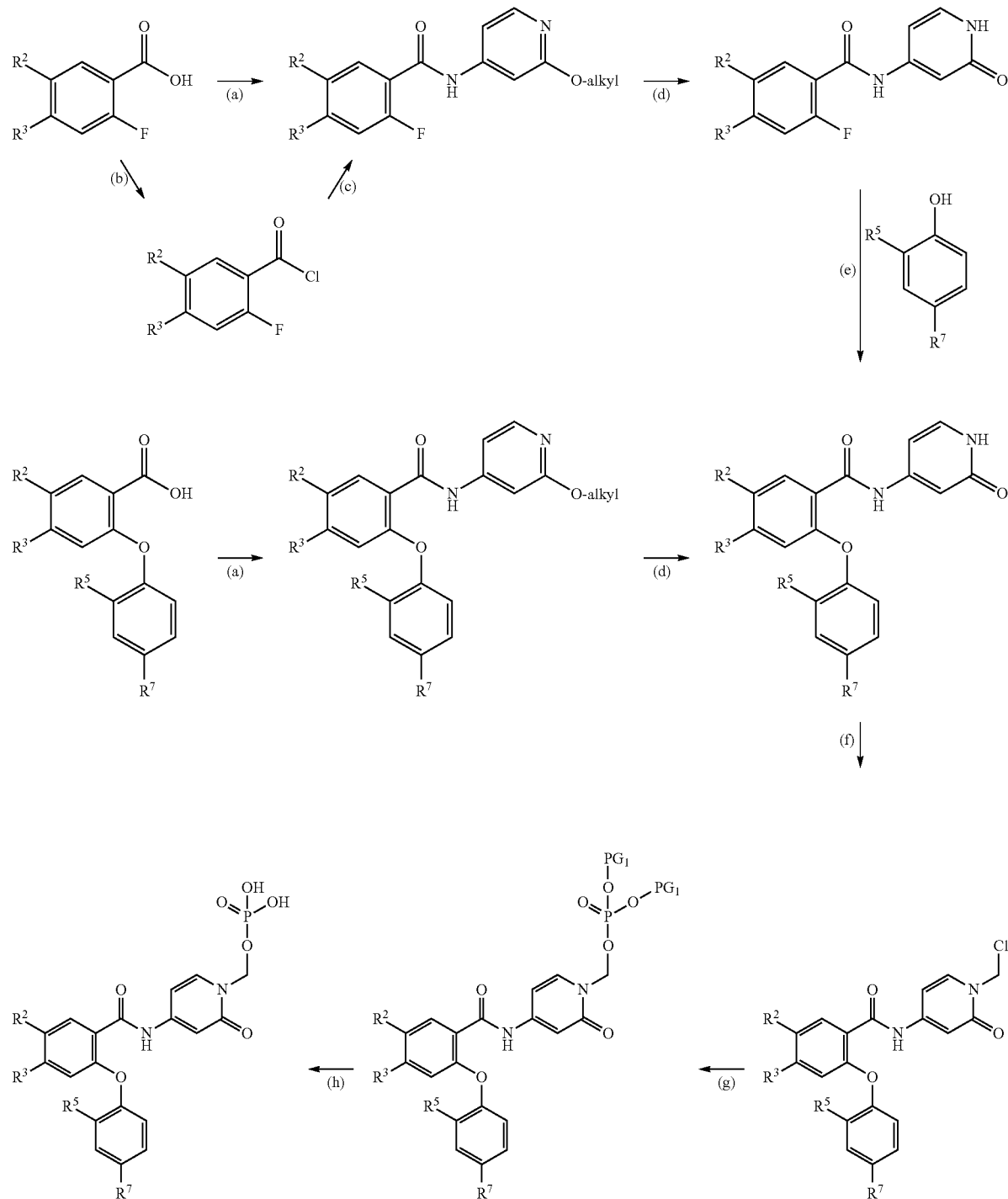

a) Alkoxy pyridine-4-amine (i.e. 2-methoxypyridin-4-amine), coupling agent (i.e. HATU, EDCI, HOBT), base (i.e. N-methylmorpholine, Et$_3$N), solvent (i.e., DMF, dichloromethane); (b) SO$_2$Cl$_2$, DMF in a solvent (i.e., dichloromethane); (c) 2-Methoxypyridin-4-amine, base (i.e., pyridine), solvent (i.e., dichloromethane, DMF); (d) TMSI or HBr, solvent (i.e., acetonitrile or acetic acid); (e) base (i.e., Cs$_2$CO$_3$, Na$_2$CO$_3$, K$_2$CO$_3$, NaHCO$_3$), solvent (i.e., DMF, NMP, dioxane), heat; (f) ClCO$_2$CH$_2$Cl, solvent (i.e., CH$_2$Cl$_2$, DMF); (g) Phosphorylating reagent (i.e. K(PG$_1$)$_2$PO$_4$ including K(t-Bu)$_2$PO$_4$ and the like), (n-Bu)$_4$NI, solvent (i.e., DMF), base (e.g., DIPEA), heat (i.e., 70° C.); (h) HOAc, H$_2$O, solvent (i.e., CH$_3$CN), heat (i.e, 70° C.).

One of skill in the art would recognize that steps (f) and (g) in Scheme 1 above may be combined into a single step without isolation of the intermediate chloride.

Scheme 1A: Preparation of Compounds of Formula I, where X is P(O)(O⁻)₂2M⁺, X is P(O)(O⁻)₂D²⁺ or X is P(O)(OH)O⁻M⁺:

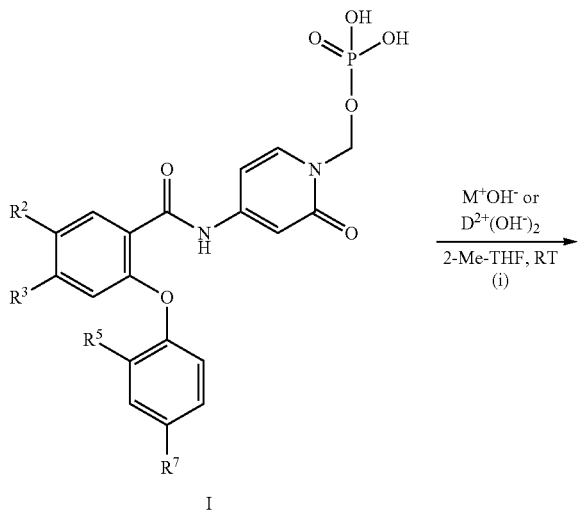

(i) M⁺OH⁻ or D²⁺(OH⁻)₂, 2-MeTHF; (j) aq H⁺; (k) aq M⁺OH⁻

Salts of compounds of formula I may be prepared as shown in Scheme 1A. In step (i), a solution of compound I treated with M⁺OH⁻ or D²⁺(OH⁻)₂ provides the dianionic form of the compound (X=—PO(O⁻)₂.2M⁺ or —PO(O⁻)₂.D²⁺). The free acid form of the compound (X=PO(OH)₂) may be obtained by treating the dianionic form with aqueous acid. The monoanionic form of the compound X=PO(OH)O⁻M⁺) may be prepared by treating the free acid form with one equivalent of M⁺OH⁻.

EXAMPLES

General Methods.

$^1$H NMR (400 MHz) and $^{31}$P NMR (162 MHz) spectra were obtained as solutions in an appropriate deuterated solvent such as dimethyl sulfoxide-d₆ (DMSO-d₆). Mass spectra (MS) were obtained using an Applied Biosystems API EX LC/MS system. Compound purity and retention times were determined by reverse phase HPLC using a Kinetix C18 column (50×2.1 mm, 1.7 μm particle) from Phenomenex (pn: 00B-4475-AN)), and a dual gradient run from 1-99% mobile phase B over 3 minutes. Mobile phase A=H₂O (0.05% CF₃CO₂H). Mobile phase B=CH₃CN (0.05% CF₃CO₂H). Flow rate=2 mL/min, injection volume=3 μL, and column temperature=50° C. Silica gel chromatography was performed using silica gel-60 with a particle size of 230-400 mesh. Pyridine, dichloromethane (CH₂Cl₂), tetrahydrofuran (THF), dimethylformamide (DMF), acetonitrile (ACN), methanol (MeOH), and 1,4-dioxane were from Baker or Aldrich and in some cases the reagents were Aldrich Sure-Seal bottles kept under dry nitrogen. All reactions were stirred magnetically unless otherwise noted. HATU stands for (1-[bis(dimethylamino)methylene]-1H-1,2,3-triazolo[4,5-b]pyridinium-3-oxide hexafluorophosphate).

Example 1

Preparation of 4-chloro-2-fluoro-N-(2-oxo-1,2-dihydropyridin-4-yl)benzamide

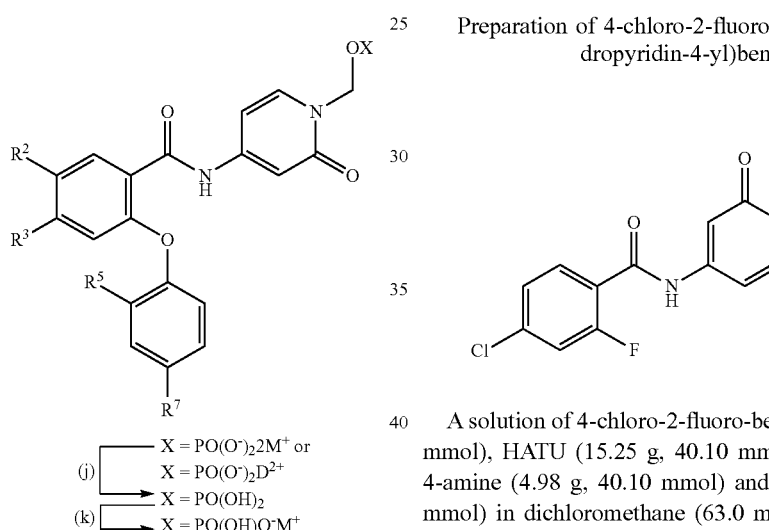

A solution of 4-chloro-2-fluoro-benzoic acid (7.0 g, 40.10 mmol), HATU (15.25 g, 40.10 mmol), 2-methoxypyridin-4-amine (4.98 g, 40.10 mmol) and Et₃N (22.4 mL, 160.4 mmol) in dichloromethane (63.0 mL) was stirred at room temperature overnight. The crude mixture was purified by column chromatography eluting with a gradient of ethyl acetate in hexanes (0-50%) to yield 4-chloro-2-fluoro-N-(2-methoxy-4-pyridyl)benzamide (4.35 g, 39%), as a white solid. ESI-MS m/z calc. 280.04, found 281.3 (M+1)⁺; Retention time: 1.31 minutes (3 minutes run). $^1$H NMR (400 MHz, DMSO-d6) δ 10.80 (s, 1H), 8.09 (m, 1H), 7.73 (t, J=8.0 Hz, 1H), 7.66 (dd, J=10.1, 1.9 Hz, 1H), 7.46 (dd, J=8.3, 1.9 Hz, 1H), 7.21 (m, 2H), 3.84 (s, 3H) ppm.

To 4-chloro-2-fluoro-N-(2-methoxy-4-pyridyl)benzamide (4.35 g, 15.50 mmol) in acetonitrile (145.0 mL) was added TMSI (8.8 mL, 62.0 mmol). The reaction was stirred at 50° C. overnight. The acetonitrile was evaporated and the crude solid was triturated with ethyl acetate. The solid was isolated by filtration and washed with ethyl acetate to give 4-chloro-2-fluoro-N-(2-oxo-1H-pyridin-4-yl)benzamide (3.8 g, 92%). ESI-MS m/z calc. 266.02, found 267.1 (M+1)+; Retention time: 1.23 minutes (3 minutes run). $^1$H NMR (400 MHz, DMSO-d₆) δ 10.86 (s, 1H), 7.73 (t, J=8.0 Hz, 1H), 7.68 (dd, J=10.1, 1.9 Hz, 1H), 7.60 (d, J=7.1 Hz, 1H), 7.47 (dd, J=8.3, 2.0 Hz, 1H), 7.11 (d, J=2.0 Hz, 1H), 6.71 (dd, J=7.1, 2.1 Hz, 1H) ppm.

Example 2

Preparation of 2-fluoro-N-(2-oxo-1,2-dihydropyridin-4-yl)-4-(perfluoroethyl)benzamide

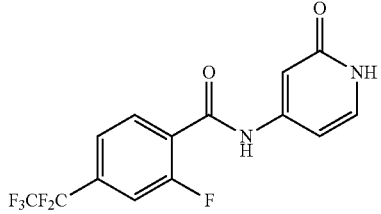

A solution of 4-bromo-2-fluoro-benzoyl chloride (2 g, 8.42 mmol) in dichloromethane (10.0 mL) was added drop-wise to a mixture of 2-methoxypyridin-4-amine (1.0 g, 8.42 mmol), pyridine (2.0 mL, 25.27 mmol) and dichloromethane (40.0 mL) at 0° C. The mixture was allowed to warm to room temperature and was stirred at that temperature overnight. The mixture was poured into 1N HCl (200 mL) and dichloromethane (200 mL). The layers were separated and the organic layer was dried over sodium sulfate, filtered and concentrated under reduced pressure to give 4-bromo-2-fluoro-N-(2-methoxy-4-pyridyl)benzamide (1.2 g, 44%) as an off-white solid. ESI-MS m/z calc. 323.99, found 325.1 (M+1)$^+$; Retention time: 1.37 minutes (3 minutes run). $^1$H NMR (400 MHz, DMSO-$d_6$) δ 10.80 (s, 1H), 8.11-8.06 (m, 1H), 7.79 (dd, J=9.8, 1.7 Hz, 1H), 7.68-7.62 (m, 1H), 7.59 (dd, J=8.3, 1.7 Hz, 1H), 7.23-7.18 (m, 2H), 3.84 (s, 3H) ppm.

To a stirred solution of 4-bromo-2-fluoro-N-(2-methoxy-4-pyridyl)benzamide (800 mg, 2.46 mmol) and copper (1.6 g, 24.61 mmol) in DMSO (15 mL), in a pressure vessel was bubbled in 1,1,1,2,2-pentafluoro-2-iodo-ethane (4.1 g, 16.47 mmol) The vessel was sealed and heated at 120° C. for 16 hours. The reaction mixture was diluted with water and filtered through a plug of silica and then extracted with ethyl acetate (4×). The organics combined, washed with brine, dried over Na$_2$SO$_4$, filtered and evaporated to dryness to yield a crude mixture that was purified by column chromatography using a gradient of ethyl acetate in hexanes (0-40%) to give 2-fluoro-N-(2-methoxy-4-pyridyl)-4-(1,1,2,2,2-pentafluoroethyl)benzamide (200 mg, 22%) as an off white solid. ESI-MS m/z calc. 364.06, found 365.3 (M+1)+; Retention time: 1.39 minutes (3 minutes run). $^1$H NMR (400 MHz, DMSO-$d_6$) δ 10.98 (s, 1H), 8.11 (d, J=6.3 Hz, 1H), 7.95 (dd, J=7.4 Hz, 1H), 7.89 (d, J=9.9 Hz, 1H), 7.72 (d, J=9.1 Hz, 1H), 7.23-7.19 (m, 2H), 3.85 (s, 3H) ppm.

2-fluoro-N-(2-methoxy-4-pyridyl)-4-(1,1,2,2,2-pentafluoroethyl)benzamide (200 mg, 0.55 mmol) in HBr in acetic acid (1.3 mL of 33% w/v, 5.49 mmol) was stirred at 100° C. for 2 hours, at this time 1 ml of HBr in acetic acid (33% w/v) was added and the mixture was stirred at 100° C. for 4 hours, then cooled to room temperature. The reaction mixture was diluted with water and a precipitate formed. The precipitate was filtered off, washed with water (2×), cold methyl-tert-butyl ether and dried under vacuum to give 2-fluoro-N-(2-oxo-1H-pyridin-4-yl)-4-(1,1,2,2,2-pentafluoroethyl)benzamide (138 mg, 72%) as a light grey solid. ESI-MS m/z calc. 350.05, found 351.3 (M+1)+; Retention time: 1.3 minutes (3 minutes run).

Example 3

Preparation of 4,5-dichloro-2-fluoro-N-(2-oxo-1,2-dihydropyridin-4-yl)benzamide

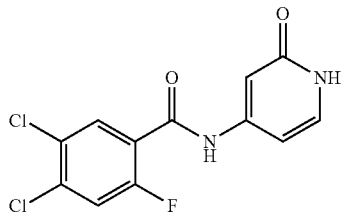 [SMILES: O=C(Nc1cc[nH]c(=O)c1)c1cc(Cl)c(Cl)cc1F]

A solution of 2-methoxypyridin-4-amine (186.2 mg, 1.5 mmol), 4,5-dichloro-2-fluoro-benzoic acid (285.1 mg, 1.36 mmol), HATU (622.4 mg, 1.64 mmol) and N-methylmorpholine (299.9 μL, 2.73 mmol) in DMF (3 mL) was stirred at room temperature for 16 hours. The reaction mixture was poured into water and extracted with ethyl acetate (3×). The organics were combined, washed with water (3×), brine and dried over Na$_2$SO$_4$, filtered through a short plug of silica and evaporated to dryness. The material was taken up in HBr (in acetic acid) (6.689 mL of 33% w/v, 27.28 mmol) and stirred at 95° C. for 16 h. The solution was cooled to room temperature, filtered and solid product washed with water (2×) and then ether (2×) and dried under vacuum to give 4,5-dichloro-2-fluoro-N-(2-oxo-1H-pyridin-4-yl)benzamide (250 mg, 61%) as an off white solid. ESI-MS m/z calc. 299.99, found 301.3 (M+1)$^+$; Retention time: 1.16 minutes (3 minutes run).

Example 4

Preparation of 2-fluoro-N-(2-oxo-1,2-dihydropyridin-4-yl)-4-(trifluoromethyl)benzamide (19)

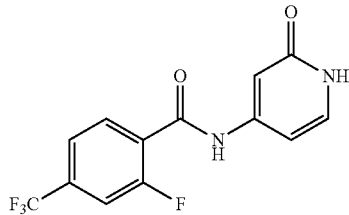 [SMILES: O=C(Nc1cc[nH]c(=O)c1)c1ccc(C(F)(F)F)cc1F]

A solution of 2-fluoro-4-(trifluoromethyl)benzoyl chloride (25.0 g, 110.3 mmol) in dichloromethane (125.0 mL) was added drop-wise to a mixture of 2-methoxypyridin-4-amine (13.7 g, 110.3 mmol), pyridine (26.8 mL, 330.9 mmol) and dichloromethane (500.0 mL) at 0° C. The mixture was allowed to warm to room temperature and was stirred at that temperature overnight. The mixture was poured into 1N HCl (200 mL) and dichloromethane (200 mL). The layers were separated and the organic layer was dried over sodium sulfate, filtered and concentrated under reduced pressure. The product was slurried in hexane, the hexane was decanted and the product was dried under reduced pressure to yield 2-fluoro-N-(2-methoxy-4-pyridyl)-4-(trifluoromethyl)benzamide (25.7 g, 74%) as a cream solid. ESI-MS m/z calc. 314.07, found 315.3 (M+1)$^+$; Retention time: 1.49 minutes (3 minutes run). $^1$H NMR (400

MHz, DMSO-d$_6$) δ 10.96 (s, 1H), 8.15-8.04 (m, 1H), 8.00-7.85 (m, 2H), 7.76 (d, J=8.1 Hz, 1H), 7.26-7.15 (m, 2H), 3.85 (s, 3H) ppm.

To 2-fluoro-N-(2-methoxy-4-pyridyl)-4-(trifluoromethyl) benzamide (1.00 g, 3.18 mmol) in acetic acid (6.0 mL) was added HBr (33% in acetic acid) (3.9 mL of 33% w/v, 15.91 mmol) and the mixture stirred at 100° C. for 6 hours. Additional HBr (2 mL, 33% in acetic acid) was added and the mixture was stirred at room temperature overnight. The mixture was then heated at 100° C. for 2 hours before it was cooled to room temperature. The mixture was partitioned between ethyl acetate and water. The layers were separated and the aqueous layer was extracted with ethyl acetate (3×). The combined organics were washed with water and brine (2×), dried over sodium sulfate, filtered and concentrated under reduced pressure. The solid was slurried in methyl-tert-butyl ether and filtered to give 2-fluoro-N-(2-oxo-1H-pyridin-4-yl)-4-(trifluoromethyl)benzamide (19) (731 mg, 76%). ESI-MS m/z calc. 301.05, found 301.3 (M+1)$^+$; Retention time: 1.35 minutes (3 minute run). $^1$H NMR (400 MHz, DMSO-d$_6$) δ 11.33 (s, 1H), 10.70 (s, 1H), 7.96-7.85 (m, 2H), 7.75 (d, J=8.2 Hz, 1H), 7.35 (d, J=7.2 Hz, 1H), 6.81 (d, J=1.9 Hz, 1H), 6.41 (dd, J=7.2, 2.1 Hz, 1H) ppm.

Example 5

Preparation of N-(2-oxo-1,2-dihydropyridin-4-yl)-2-(4-(trifluoromethoxy)phenoxy)-4-(trifluoromethyl)benzamide (5a)

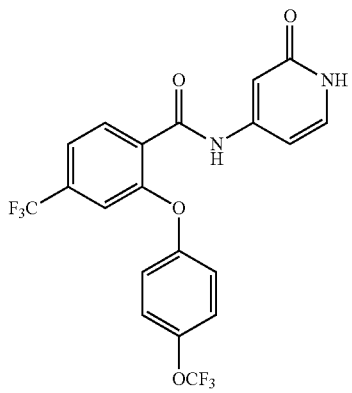 [SMILES: O=C(Nc1cc[nH]c(=O)c1)c1ccc(C(F)(F)F)cc1Oc1ccc(OC(F)(F)F)cc1]

Cs$_2$CO$_3$ (651.6 mg, 2 mmol) was added to a solution of 2-fluoro-N-(2-oxo-1,2-dihydropyridin-4-yl)-4-(trifluoromethyl)benzamide (60.0 mg, 0.2 mmol) and 4-(trifluoromethoxy)phenol (259.1 μL, 2 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield N-(2-oxo-1,2-dihydropyridin-4-yl)-2-(4-(trifluoromethoxy)phenoxy)-4-(trifluoromethyl)benzamide (5a) (25.7 mg, 28%). ESI-MS m/z calc. 458.07, found 459.5 (M+1)$^+$; Retention time: 1.80 minutes (3 minutes run).

Example 6

Preparation of 2-(4-fluoro-2-methylphenoxy)-N-(2-oxo-1,2-dihydropyridin-4-yl)-4-(trifluoromethyl)benzamide (9a)

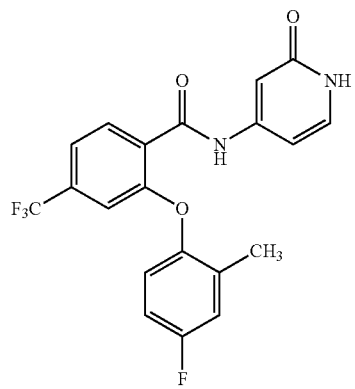 [SMILES: Cc1cc(F)ccc1Oc1cc(C(F)(F)F)ccc1C(=O)Nc1cc[nH]c(=O)c1]

A mixture of 2-fluoro-N-(2-oxo-1H-pyridin-4-yl)-4-(trifluoromethyl)-benzamide (13.6 g, 45.30 mmol), 4-fluoro-2-methyl-phenol (17.1 g, 135.9 mmol), Cs$_2$CO$_3$ (44.28 g, 135.9 mmol) and DMF (340.0 mL) was heated at 100° C. for 1.5 hours. The mixture was cooled to room temperature and was poured into water (500 mL). The mixture was stirred vigorously for 30 min before it was filtered. The solid was washed with water (250 mL) and was slurried with methyl tert-buthyl ether (200 mL). The mixture was filtered and the solid was slurried with hexanes (2×400 mL) and the filtrate was dried under vacuum to give 2-(4-fluoro-2-methyl-phenoxy)-N-(2-oxo-1H-pyridin-4-yl)-4-(trifluoromethyl)benzamide (9a) (13.1 g, 70%) as a solid. ESI-MS m/z calc. 406.09, found 407.5 (M+1)$^+$; Retention time: 1.73 minutes (3 minutes run). $^1$H NMR (400 MHz, DMSO-d$_6$) δ 11.28 (s, 1H), 10.63 (s, 1H), 7.84 (d, J=7.8 Hz, 1H), 7.60 (d, J=7.1 Hz, 1H), 7.31 (d, J=7.2 Hz, 1H), 7.26-7.20 (m, 1H), 7.14-7.06 (m, 2H), 7.00-6.95 (m, 1H), 6.75 (d, J=1.8 Hz, 1H), 6.38 (dd, J=7.2, 2.1 Hz, 1H), 2.16 (s, 3H) ppm.

Example 7

Preparation of 2-(4-fluoro-2-methoxyphenoxy)-N-(2-oxo-1,2-dihydropyridin-4-yl)-5-(trifluoromethyl)benzamide (4a)

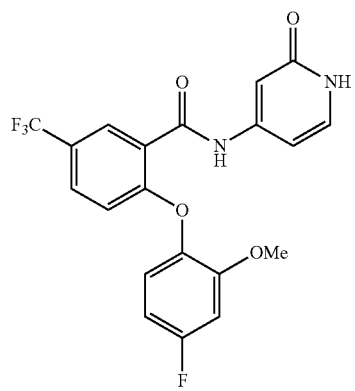 [SMILES: COc1cc(F)ccc1Oc1ccc(C(F)(F)F)cc1C(=O)Nc1cc[nH]c(=O)c1]

Cs$_2$CO$_3$ (651.6 mg, 2.0 mmol) was added to a solution of 2-fluoro-N-(2-oxo-1,2-dihydropyridin-4-yl)-5-(trifluoromethyl)benzamide (60.0 mg, 0.2 mmol) and 4-fluoro-3-methoxyphenol (228 µl, 2.0 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 2-(4-fluoro-2-methoxyphenoxy)-N-(2-oxo-1,2-dihydropyridin-4-yl)-5-(trifluoromethyl)benzamide (4a) (67.9 mg, 80%). ESI-MS m/z calc. 422.09, found 423.2 (M+1)$^+$; Retention time: 1.56 minutes (3 minutes run).

Following a similar procedure as described above for parent compound 4a, the following compounds were prepared from 2-fluoro-N-(2-oxo-1,2-dihydropyridin-4-yl)-5-(trifluoromethyl)benzamide and the following alcohols.

| Cmpd No. | Product | Alcohol |
|---|---|---|
| 18a | 2-(4-fluorophenoxy)-N-(2-oxo-1,2-dihydropyridin-4-yl)-5-(trifluoromethyl)benzamide | 4-fluorophenol |
| 15a | N-(2-oxo-1,2-dihydropyridin-4-yl)-2-(o-tolyloxy)-5-(trifluoromethyl)benzamide | 2-methylphenol |
| 11a | 2-(2-chloro-4-fluorophenoxy)-N-(2-oxo-1,2-dihydropyridin-4-yl)-5-(trifluoromethyl)benzamide | 2-chloro-4-fluoro-phenol |
| 10a | 2-(4-fluoro-2-methylphenoxy)-N-(2-oxo-1,2-dihydropyridin-4-yl)-5-(trifluoromethyl)benzamide | 4-fluoro-2-methyl-phenol |
| 8a | N-(2-oxo-1,2-dihydropyridin-4-yl)-2-(4-(trifluoromethoxy)phenoxy)-5-(trifluoromethyl)benzamide | 4-(trifluoromethoxy)phenol |
| 17a | N-(2-oxo-1,2-dihydropyridin-4-yl)-2-(2-(trifluoromethoxy)phenoxy)-5-(trifluoromethyl)benzamide | 2-(trifluoromethoxy)phenol |

Example 8

Preparation of 5-chloro-2-(4-fluoro-2-methoxyphenoxy)-N-(2-oxo-1,2-dihydropyridin-4-yl)benzamide (7a)

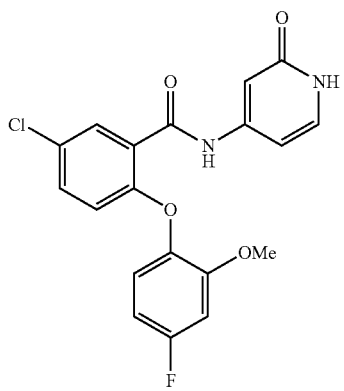 [SMILES: COc1cc(F)ccc1Oc1ccc(Cl)cc1C(=O)Nc1cc[nH]c(=O)c1]

Cs$_2$CO$_3$ (879.9 mg, 2.7 mmol) was added to a solution of 2-fluoro-N-(2-oxo-1,2-dihydropyridin-4-yl)-5-chlorobenzamide (72.0 mg, 0.27 mmol) and 4-fluoro-3-methoxyphenol (307.7 µl, 2.7 mmol) in DMF (1 mL) and the reaction was stirred at 100° C. for 1 hour. The reaction was filtered and purified by reverse phase HPLC using a gradient of acetonitrile in water (10-99%) and HCl as a modifier to yield 5-chloro-2-(4-fluoro-2-methoxyphenoxy)-N-(2-oxo-1,2-dihydropyridin-4-yl)benzamide (7a) (31.8 mg, 30%). ESI-MS m/z calc. 388.06, found 389.10 (M+1)$^+$; Retention time: 1.52 minutes (3 minutes run).

Following a similar procedure as described above for parent compound 7a, the following compounds were prepared from 5-chloro-2-(4-fluoro-2-methoxyphenoxy)-N-(2-oxo-1,2-dihydropyridin-4-yl)benzamide and the following alcohols.

| Cmpd No. | Product | Alcohol |
|---|---|---|
| 12a | 5-chloro-2-(4-fluoro-2-methylphenoxy)-N-(2-oxo-1,2-dihydropyridin-4-yl)benzamide | 4-fluoro-2-methyl-phenol |
| 14a | 5-chloro-2-(2-chloro-4-fluorophenoxy)-N-(2-oxo-1,2-dihydropyridin-4-yl)benzamide | 2-chloro-4-fluoro-phenol |

Example 9

Preparation of 4,5-dichloro-2-(4-fluoro-2-methoxyphenoxy)-N-(2-oxo-1,2-dihydropyridin-4-yl)benzamide (1a)

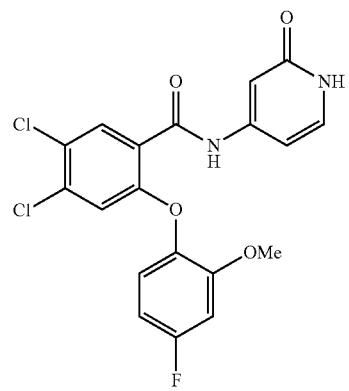 [SMILES: COc1cc(F)ccc1Oc1cc(Cl)c(Cl)cc1C(=O)Nc1cc[nH]c(=O)c1]

Cs$_2$CO$_3$ (97.7 mg, 0.3 mmol) was added to a solution of 4,5-dichloro-2-fluoro-N-(2-oxo-1,2-dihydropyridin-4-yl)benzamide (30.1 mg, 0.1 mmol) and 4-fluoro-3-methoxyphenol (42.6 mg, 0.3 mmol) in NMP (0.5 mL) and the reaction was stirred at 90° C. for 2 hours. The reaction was filtered and purified by reverse phase HPLC using a gradient of acetonitrile in water (1-99%) and HCl as a modifier to yield 4,5-dichloro-2-(4-fluoro-2-methoxyphenoxy)-N-(2-oxo-1,2-dihydropyridin-4-yl)benzamide (1a) (13.2 mg, 30%). ESI-MS m/z calc. 422.02, found 423.3 (M+1)$^+$; Retention time: 1.57 minutes (3 minutes run).

Following a similar procedure as described above for parent compound 1a, the following compounds were prepared from 4,5-dichloro-2-fluoro-N-(2-oxo-1,2-dihydropyridin-4-yl)benzamide and the following alcohols.

| Cmpd No. | Product | Alcohol |
|---|---|---|
| 3a | 4,5-dichloro-2-(4-fluorophenoxy)-N-(2-oxo-1,2-dihydropyridin-4-yl)benzamide | 4-fluorophenol |

Example 10

Preparation of 2-(4-fluoro-2-methoxyphenoxy)-N-(2-oxo-1,2-dihydropyridin-4-yl)-4-(perfluoroethyl)benzamide (2a)

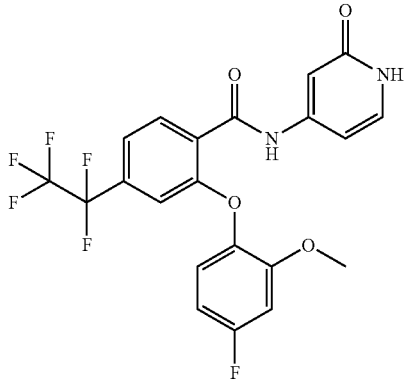 [SMILES: COc1cc(F)ccc1Oc1cc(C(F)(F)C(F)(F)F)ccc1C(=O)Nc1cc[nH]c(=O)c1]

Cs₂CO₃ (69.8 mg, 0.21 mmol) was added to a solution of 2-fluoro-N-(2-oxo-1,2-dihydropyridin-4-yl)-4-(perfluoroethyl)benzamide (25 mg, 0.07 mmol) and 4-fluoro-2-methoxyphenol (24.4 µL, 0.2 mmol) in NMP (0.3 mL) and the reaction was stirred at 100° C. for 45 minutes. The reaction mixture was poured into water:ethyl acetate (9:1). The mixture was shaken, and the solid was filtered off, washed with ether, then triturated with ethyl acetate and dried to give the desired product. The mother liquors were filtered and washed with ethyl acetate to give a second crop of material. Both solids were combined and dried under vacuum to give 2-(4-fluoro-2-methoxy-phenoxy)-N-(2-oxo-1H-pyridin-4-yl)-4-(1,1,2,2,2-pentafluoroethyl)benzamide (2a) (15.4 mg, 45%) as a white solid. ESI-MS m/z calc. 472.08, found 473.3 (M+1)+; Retention time: 1.62 minutes. ¹H NMR (400 MHz, DMSO-d₆) δ 11.32 (s, 1H), 10.62 (s, 1H), 7.83 (d, J=7.9 Hz, 1H), 7.51 (d, J=7.9 Hz, 1H), 7.39-7.27 (m, 2H), 7.17 (dd, J=10.7, 2.8 Hz, 1H), 6.88 (dd, J=11.3, 5.7 Hz, 1H), 6.81 (s, 1H), 6.75 (s, 1H), 6.43 (d, J=7.1 Hz, 1H), 3.73 (s, 3H) ppm.

Example 11

Preparation of 4-chloro-2-(4-fluoro-2-methylphenoxy)-N-(2-oxo-1,2-dihydropyridin-4-yl)benzamide (13a)

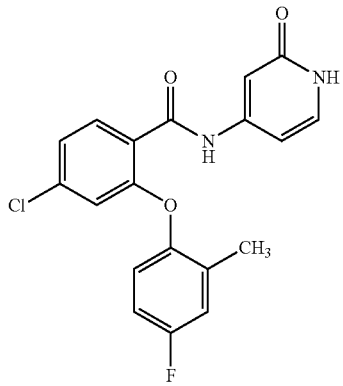 [SMILES: Cc1cc(F)ccc1Oc1cc(Cl)ccc1C(=O)Nc1cc[nH]c(=O)c1]

To a solution of 4-chloro-2-fluoro-N-(2-oxo-1H-pyridin-4-yl)benzamide (500 mg, 1.87 mmol) in NMP (5 mL) was added 4-fluoro-2-methyl-phenol (709.5 mg, 5.62 mmol) and Cs₂CO₃ (1.83 g, 5.62 mmol) and the reaction mixture was stirred at 90° C. for 2 hours. The reaction mixture was poured into water and extracted with ethyl acetate (3×). The organics were combined, washed with 3N NaOH (3×), water, brine, dried (Na₂SO₄) and evaporated to dryness. Purification by silica gel column chromatography gave 4-chloro-2-(4-fluoro-2-methyl-phenoxy)-N-(2-oxo-1H-pyridin-4-yl)benzamide (13a) (300 mg, 43%) as a tan solid. ESI-MS m/z calc. 372.07, found 373.1 (M+1)+; Retention time: 1.5 minutes (3 minutes run). ¹H NMR (400 MHz, DMSO-d₆) δ 11.25 (s, 1H), 10.48 (s, 1H), 7.65 (d, J=8.2 Hz, 1H), 7.30 (dd, J=7.9, 1.6 Hz, 2H), 7.21 (d, J=8.7 Hz, 1H), 7.09 (d, J=5.5 Hz, 2H), 6.75 (dd, J=5.1, 1.8 Hz, 2H), 6.38 (dd, J=7.2, 2.0 Hz, 1H), 2.16 (s, 3H) ppm.

Example 12

Preparation of 2-(2,4-difluorophenoxy)-N-(2-oxo-1,2-dihydropyridin-4-yl)-4-(trifluoromethyl)benzamide (16a)

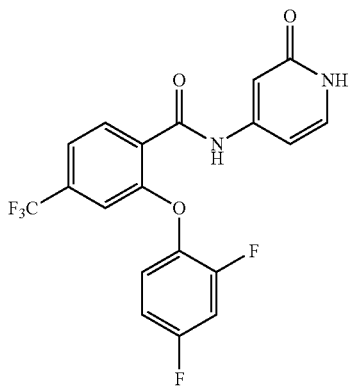 [SMILES: O=C(Nc1cc[nH]c(=O)c1)c1ccc(C(F)(F)F)cc1Oc1ccc(F)cc1F]

To a solution of 2-fluoro-N-(2-oxo-1,2-dihydropyridin-4-yl)-4-(trifluoromethyl)benzamide (30 mg, 0.1 mmol) in DMF (1 mL) was added 2,4-difluorophenol (130 mg, 1.0 mmol) and Cs₂CO₃ (325.8 m g, 1.0 mmol) and the reaction mixture was stirred at 100° C. for 1 hour. The reaction was cooled to 25° C., filtered and purified by reverse phase chromatography using a gradient of acetonitrile in water (10-99%) and HCl as a modifier to yield 2-(2,4-difluorophenoxy)-N-(2-oxo-1,2-dihydropyridin-4-yl)-4-(trifluoromethyl)benzamide (16). ESI-MS m/z calc. 410.07, found 411.2 (M+1)+; Retention time: 1.55 minutes (3 minutes run).

Example 13

Preparation of N-[1-(chloromethyl)-2-oxo-4-pyridyl]-2-(4-fluoro-2-methyl-phenoxy)-4-(trifluoromethyl)benzamide (20)

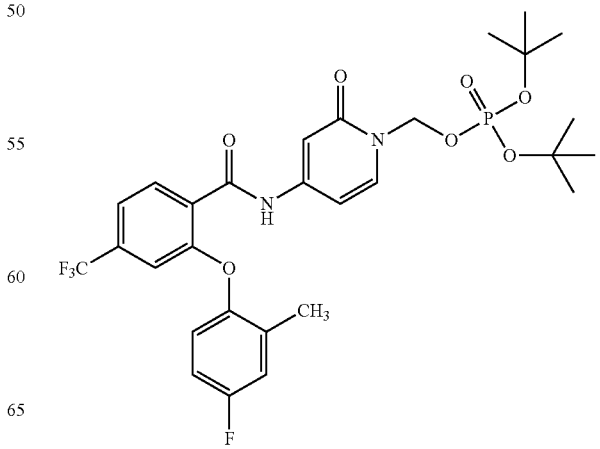

A solution of 2-(4-fluoro-2-methylphenoxy)-N-(2-oxo-1,2-dihydropyridin-4-yl)-4-(trifluoromethyl)benzamide (9a) (406.3 mg, 1.0 mmol) and chloromethyl chloroformate (106.7 μL, 1.2 mmol) in dichloromethane (3.5 mL) and N,N-dimethylformamide (0.3 mL) was stirred at room temperature for 4 hours. The reaction mixture was diluted with ethyl acetate, washed with saturated aqueous sodium bicarbonate, brine, dried with $Na_2SO_4$, filtered and evaporated to dryness to give N-[1-(chloromethyl)-2-oxo-4-pyridyl]-2-(4-fluoro-2-methyl-phenoxy)-4-(trifluoromethyl)benzamide that was used in the next step without further purification. ESI-MS m/z calc. 454.07, found 455 $(M+1)^+$; Retention time: 0.73 minutes (1 minute run).

The crude N-[1-(chloromethyl)-2-oxo-4-pyridyl]-2-(4-fluoro-2-methyl-phenoxy)-4-(trifluoromethyl)benzamide from the previous step was taken up in N,N-dimethylformamide (5 mL). Di-tert-butoxyphosphoryloxypotassium (496.6 mg, 2.0 mmol) and tetrabutylammonium iodide (36.94 mg, 0.10 mmol) were added and the reaction mixture was stirred at 70° C. for 4 hours. The reaction mixture was then diluted with ethyl acetate and washed with water then brine, dried with $Na_2SO_4$, filtered and evaporated to dryness. The material was purified by column chromatography (40 g silica, 50-100% EtOAc in Hexanes), fractions with the product were pooled and evaporated to give di-tert-butyl [4-[[2-(4-fluoro-2-methyl-phenoxy)-4-(trifluoromethyl)benzoyl]amino]-2-oxo-1-pyridyl]methyl phosphate (20) (280 mg, 45%) as a yellow oil that was used in the next step without further purification. ESI-MS m/z calc. 628.20, found 629 $(M+1)^+$; Retention time: 0.76 minutes (1 minute run).

Example 14

Preparation of [4-[[2-(4-fluoro-2-methyl-phenoxy)-4-(trifluoromethyl)benzoyl]amino]-2-oxo-1-pyridyl]methyl dihydrogen phosphate (9)

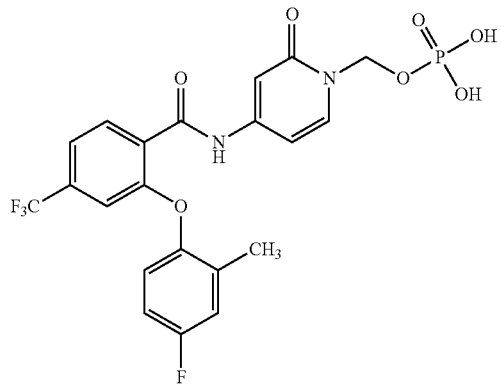 [SMILES: Cc1cc(F)ccc1Oc1cc(C(F)(F)F)ccc1C(=O)Nc1ccn(COP(=O)(O)O)c(=O)c1]

A solution of di-tert-butyl [4-[[2-(4-fluoro-2-methyl-phenoxy)-4-(trifluoromethyl)benzoyl]amino]-2-oxo-1-pyridyl]methyl phosphate (20) (50 mg, 0.080 mmol) in acetonitrile (1 mL), $H_2O$ (1 mL), and acetic acid (1 mL) was stirred at 70° C. for 3 hours then evaporated to dryness. The material was then co-evaporated with acetonitrile (3×), triturated with acetonitrile, filtered, washed with acetonitrile and desiccated to give [4-[[2-(4-fluoro-2-methyl-phenoxy)-4-(trifluoromethyl)benzoyl]amino]-2-oxo-1-pyridyl]methyl dihydrogen phosphate (9) (20 mg, 49%) as a white solid. $^1$H NMR (400 MHz, DMSO-$d_6$) δ 11.49 (s, 2H), 10.77 (s, 1H), 7.86 (d, J=8.0 Hz, 1H), 7.61 (d, J=7.6 Hz, 2H), 7.27-7.19 (m, 1H), 7.11 (dd, J=10.9, 7.6 Hz, 2H), 6.98 (s, 1H), 6.90 (d, J=2.0 Hz, 1H), 6.43 (dd, J=7.5, 2.1 Hz, 1H), 5.53 (d, J=9.7 Hz, 2H), 2.16 (s, 3H) ppm. $^{31}$P NMR (162 MHz, DMSO-$d_6$–85% $H_3PO_4$ aq. as internal standard–0 ppm) 6-1.76 (t, J=9.6 Hz, 1H).

The material was further purified according to the following procedure. To a stirred suspension of [4-[[2-(4-fluoro-2-methyl-phenoxy)-4-(trifluoromethyl)benzoyl]amino]-2-oxo-1-pyridyl]methyl dihydrogen phosphate (9) (30.00 mg, 0.05810 mmol) in isopropanol (600.0 μL) was added methanol (300.0 μL) which caused the material to go into solution. NaOH (14.52 μL of 4 M, 0.058 mmol) was added which caused a white precipitate and the mixture was stirred at room temperature for 30 minutes. The reaction mixture was then cooled to 0° C., filtered, washed with cooled isopropanol and dried under vacuum to give [4-[[2-(4-fluoro-2-methyl-phenoxy)-4-(trifluoromethyl)benzoyl]amino]-2-oxo-1-pyridyl]methyl dihydrogen phosphate (9) as a white solid. ESI-MS m/z calc. 516.07, found 517.0 (M+1)+; Retention time: 0.57 minutes (1 min UPLC run).

Example 15

Alternate preparation of [4-[[2-(4-fluoro-2-methyl-phenoxy)-4-(trifluoromethyl)benzoyl]amino]-2-oxo-1-pyridyl]methyl dihydrogen phosphate (9)

A sample of 2-(4-fluoro-2-methylphenoxy)-N-(2-oxo-1,2-dihydropyridin-4-yl)-4-(trifluoromethyl)benzamide monohydrate (9a) (6.0 g, 14.7 mmol) was dehydrated under vacuum at 65° C. A solution of anhydrous 2-(4-fluoro-2-methylphenoxy)-N-(2-oxo-1,2-dihydropyridin-4-yl)-4-(trifluoromethyl)benzamide (9a) (5.0 g, 12.31 mmol) and N,N-dimethylformamide (10.0 mL) in dichloromethane (50.0 mL) was stirred at room temp., chloromethyl chloroformate (1.64 ml, 18.46 mmol) was added and the solution was stirred at room temperature for one hour. The reaction mixture was diluted with ethyl acetate, washed with saturated aqueous sodium bicarbonate, brine, dried with anhydrous sodium sulfate, filtered and evaporated to dryness. The resulting oil was purified by column chromatography (40 g silica, 20-100% EtOAc in Hexanes), product fractions were pooled and evaporated to give N-[1-(chloromethyl)-2-oxo-4-pyridyl]-2-(4-fluoro-2-methyl-phenoxy)-4-(trifluoromethyl)benzamide (3.26 g, 7.168 mmol) that was used in the next step without further purification. $^1$H NMR (400 MHz, DMSO-$d_6$) δ 10.83 (s, 1H), 7.86 (d, J=7.8 Hz, 1H), 7.76 (d, J=7.6 Hz, 1H), 7.66-7.58 (m, 1H), 7.28-7.19 (m, 1H), 7.10 (dd, J=7.7, 2.0 Hz, 2H), 6.98 (s, 1H), 6.92 (d, J=2.1 Hz, 1H), 6.50 (dd, J=7.6, 2.3 Hz, 1H), 5.79 (s, 2H), 2.16 (s, 3H) ppm.

A mixture of N-[1-(chloromethyl)-2-oxo-4-pyridyl]-2-(4-fluoro-2-methyl-phenoxy)-4-(trifluoromethyl)benzamide (500 mg, 1.1 mmol), di-tert-butoxyphosphoryloxy potassium (409.2 mg, 1.65 mmol), tetrabutylammonium iodide (20.3 mg, 0.05 mmol) and diisopropylethyl amine (191.4 ul, 1.1 mmol) in acetonitrile (10.0 ml) were stirred at 70° C. for one hour. The reaction mixture was then diluted with ethyl acetate and washed with water and brine and the organic layer was evaporated to dryness. The crude material was purified by column chromatography (4 g silica, 25-100% EtOAc in Hexanes), product fractions were pooled and evaporated to give di-tert-butyl [4-[[2-(4-fluoro-2-methyl-phenoxy)-4-(trifluoromethyl)benzoyl]amino]-2-oxo-1-pyridyl]methyl phosphate (20) (390 mg, 56%) as a light amber solid. $^1$H NMR (400 MHz, DMSO-$d_6$) δ 10.83 (s, 1H), 7.86 (d, J=7.8 Hz, 1H), 7.76 (d, J=7.6 Hz, 1H), 7.66-7.58 (m, 1H), 7.28-7.19 (m, 1H), 7.10 (dd, J=7.7, 2.0 Hz, 2H), 6.98 (s, 1H), 6.92 (d, J=2.1 Hz, 1H), 6.50 (dd, J=7.6, 2.3 Hz, 1H), 5.79 (s, 2H), 2.16 (s, 3H) ppm.

A solution of di-tert-butyl [4-[[2-(4-fluoro-2-methyl-phenoxy)-4-(trifluoromethyl)benzoyl]amino]-2-oxo-1-pyridyl]methyl phosphate (20) (350 mg, 0.557 mmol) in acetonitrile (7 mL), acetic acid (7 mL), and $H_2O$ (7 mL) was stirred at 70° C. and the deprotection reaction followed by HPLC. Deprotection was complete after 1.5 hours. The reaction mixture was partially concentrated to remove the bulk of the acetonitrile then toluene (100 ml) was added and the mixture evaporated to azeotropically remove water and acetic acid. To the resulting suspension was added heptane (10 ml) and the suspension distilled down to 2-3 volumes (1 ml). Heptane (2 ml) was added and the suspension further stirred at room temp and filtered. The collected solid was dried in vacuo to afford [4-[[2-(4-fluoro-2-methyl-phenoxy)-4-(trifluoromethyl)benzoyl]amino]-2-oxo-1-pyridyl]methyl dihydrogen phosphate (9) (254 mg, 88.4%) as off-white crystalline solid. $^1$H NMR (400 MHz, DMSO-$d_6$) δ 11.52 (s, 2H), 10.77 (s, 1H), 7.86 (d, J=8.0 Hz, 1H), 7.60 (d, J=7.6 Hz, 2H), 7.26-7.19 (m, 1H), 7.09 (dd, J=10.9, 7.6 Hz, 2H), 6.98 (s, 1H), 6.90 (d, J=2.0 Hz, 1H), 6.43 (dd, J=7.5, 2.1 Hz, 1H), 5.53 (d, J=9.7 Hz, 2H), 2.16 (s, 3H) ppm. $^{31}$P NMR (162 MHz, DMSO-$d_6$) δ −2.35 (t, J=9.6 Hz, 1H) ppm.

Example 15A

Preparation of 2-fluoro-N-(2-methoxypyridin-4-yl)-4-(trifluoromethyl)benzamide

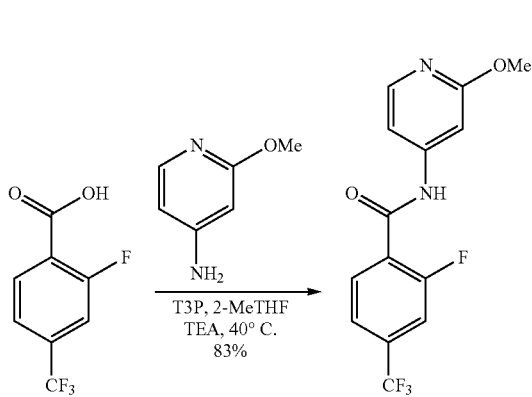

A 50 liter jacketed glass reactor was fitted with an $N_2$ inlet, a mechanical stirrer, and a condenser. With the stirrer set to 150 rpm and the jacket temperature set at 40° C., 2-Me-THF (6.000 L, 3.0 vol), 2-fluoro-4-(trifluoromethyl)benzoic acid (2000 g, 9.610 mol), 2-methoxypyridin-4-amine (1.278 kg, 10.09 mol), and TEA (2.917 kg, 4.018 L, 28.83 mol) were added to the reactor, which resulted in a slightly hazy, light amber solution. The reactor was switched to reaction control and heated to 35° C. To the solution was added T3P in 2-Me-THF (9.176 kg, 9.176 L of 50% w/w, 14.42 mol) over 30-45 min, which resulted in a light amber solution. After 2 hours, the reaction was judged to be complete by HPLC analysis (<2% of 1 remaining). The reaction was quenched with water (1.000 L, 0.5 vol), which was added via addition funnel over a period of 10 minutes in order to control the exothermic quenching reaction. The mixture was then diluted with 2-Me-THF (8.000 L, 4.0 vol) and water (8.000 L, 4.0 vol) and stirred for 30 minutes at 30-40° C. After stirring was stopped, the layers were allowed to separate, and the aqueous layer was removed. The organic layer was washed with 10% aqueous NaOH (6.000 L, 3.0 vol), stirring resulted in an emulsion. Brine (500.0 mL, 0.25 vol) was added, and the mixture was stirred for about 5 minutes. The layers were separated, and the aqueous layer removed. The organic layer was washed again with brine (10.00 L, 5.0 vol), and the aqueous layer was drained. The organic layer was dried over $Na_2SO_4$, and filtered through diatomaceous earth (Celite). The filter cake was washed with 2-Me-THF (4.000 L, 2.0 vol) and pulled dry. The filtrate was transferred to a rotovap, and partial distillation of solvent was begun at a bath temperature of 40° C. and a pressure of 150 mbar, resulting in the formation of solids in the mixture. Cyclohexane (10.00 L, 5.0 vol) was added portionwise during the partial distillation. Distillation was stopped, the reaction mixture (~8 liter) was slurried on the rotovap, and the bath temperature was reduced to room temperature. The mixture was filtered, and the filter cake was washed with cyclohexane (2.000 L, 1.0 vol) and pulled dry under a nitrogen blanket to afford a light yellow solid. The solid was scooped out of the funnel and dried in vacuo (40° C., <30 mbar, rotovap) to afford 2-fluoro-N-(2-methoxypyridin-4-yl)-4-(trifluoromethyl)benzamide (2,501 g, 7.959 mol, 83%) as a fine, off-white solid.

Example 15B

Preparation of 2-fluoro-N-(2-oxo-1,2-dihydropyridin-4-yl)-4-(trifluoromethyl)benzamide hydrobromide

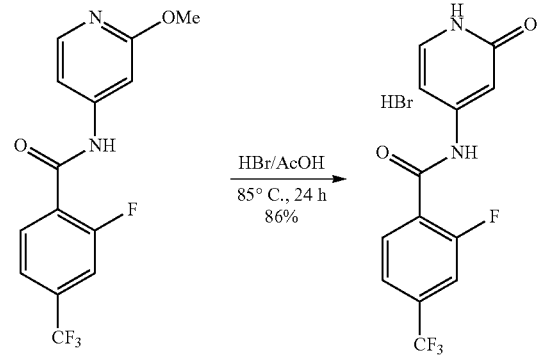 [SMILES: COc1cc(NC(=O)c2ccc(C(F)(F)F)cc2F)ccn1 ; O=C(Nc1cc[nH]c(=O)c1)c1ccc(C(F)(F)F)cc1F ; Br]

To a 50 liter jacketed glass reactor fitted with an $N_2$ inlet and a mechanical stirrer set was added AcOH (17.50 L, 7.0 vol) and 2-fluoro-N-(2-methoxypyridin-4-yl)-4-(trifluoromethyl)benzamide (2500 g, 7.956 mol), and the resulting mixture was stirred. A solution of HBr in HOAc (5.853 kg, 3.928 L of 33% w/w, 23.87 mol) was added, resulting in a mild exotherm and a light amber solution. The solution became a darker amber color as more HBr was added. The temperature of the reaction mixture was increased to a mild reflux (70° C. internal), over 30 min, resulting in the generation of a substantial amount of gas (MeBr, HBr). The internal temperature of the reaction mixture was then increased to 85° C. over 1.5 hrs, and stirring was continued overnight at a temperature of 85° C. The progress of the reaction was monitored by HPLC analysis until completion, which was achieved after about 16 hours (<1% of 2-fluoro-N-(2-methoxypyridin-4-yl)-4-(trifluoromethyl)benzamide remaining relative to the product 2-fluoro-N-(2-oxo-1,2-dihydropyridin-4-yl)-4-(trifluoromethyl)benzamide hydrobromide). The internal temperature of the reaction mixture was reduced from 85 to 50° C. over 30 min, and then toluene (7.500 L, 3.0 vol) was added. Stirring was continued for 10-15 min. The internal temperature of the reaction mixture was then reduced to 20° C., and the mixture was stirred at this temperature for 1-2 hrs. The reaction mixture was then filtered, and the wet filter cake was washed with toluene (7.500 L, 3.0 vol) and pulled dry. The solid material was scooped out of the filter and dried in vacuo (40° C., 10-25 mbar, rotovap) to afford 2-fluoro-N-(2-oxo-1,2-dihydropyridin-4-yl)-4-(trifluoromethyl)benzamide hydrobromide (2609 g, 6.846 mol, 86%) as white, crystalline solid.

Example 15C

Preparation of 2-(4-fluoro-2-methylphenoxy)-N-(2-oxo-1,2-dihydropyridin-4-yl)-4-(trifluoromethyl)benzamide (9a)

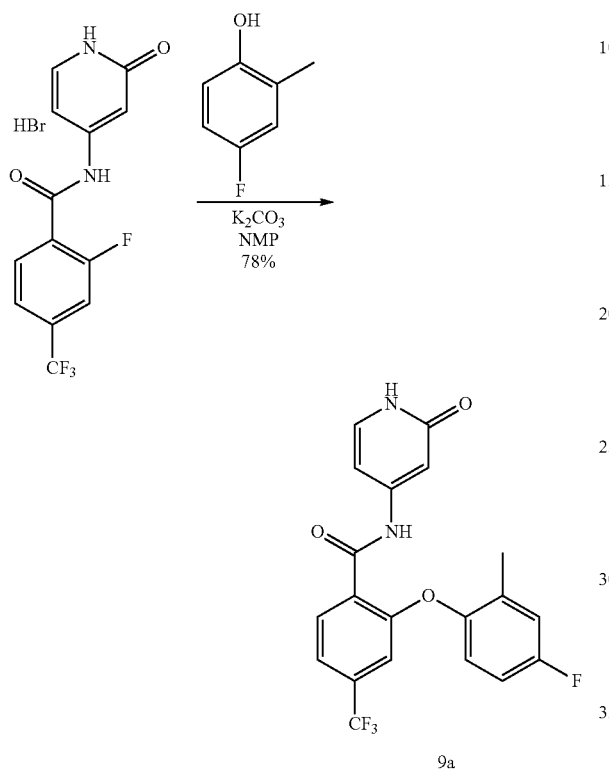

9a

To a 50 liter jacketed glass reactor fitted with an $N_2$ inlet and a mechanical stirrer was added 1-methyl-2-pyrrolidinone (NMP) (3.75 liters). The solution was stirred, 2-fluoro-N-(2-oxo-1,2-dihydropyridin-4-yl)-4-(trifluoromethyl)benzamide hydrobromide salt (1500.2 g, 3.94 moles, 1.0 eq) was added and chased with NMP (1 liter), and the jacket temperature was adjusted to 35° C. Potassium carbonate (1631.9 g, 11.8 moles, 3.0 eq, 325 mesh) was then added portionwise over 10 minutes, during which time the reaction temperature increased to 40° C. The resulting suspension was treated with a solution of 4-fluoro-2-methylphenol (5, 546.1 g, 4.33 moles, 1.1 eq, AK Scientific) in NMP (2.25 liters) with stirring, and the addition funnel was then rinsed with NMP (0.75 liters) to give an orange suspension. The jacket temperature was raised to 61° C. over 30 minutes and the suspension was stirred overnight under nitrogen, at which time the reaction was judged to be complete by HPLC analysis. To the reaction mixture was added 2-methyltetrahydrofuran (15 liters) and water (15 liters) and the mixture stirred until all solids dissolved. Stirring was stopped, the orange aqueous layer drained off, and the organic layer washed with water (7.5 liters) while stirring and a jacket temperature of 52° C.). The aqueous wash procedure was repeated 4 times (3×7.5 liter water washes, then 1×4.5 liter water wash). The resulting organic slurry was stirred at a jacket temperature of 50.8° C., and isopropyl acetate (6 liters, Sigma Aldrich) was added. The jacket temperature was ramped down to 20° C. over 30 minutes, and the slurry was stirred overnight before collecting the precipitated solid by filtration. The collected solid was returned to the reactor, slurried in isopropyl acetate with stirring for about 2 hours, then filtered, rinsed with isopropyl acetate (1.5 liters) and dried in vacuo at 65° C. to give 1253.1 g (78%) of 2-(4-fluoro-2-methylphenoxy)-N-(2-oxo-1,2-dihydropyridin-4-yl)-4-(trifluoromethyl)benzamide (9a) as an off-white solid.

Example 15D

Preparation of N-(1-(chloromethyl)-2-oxo-1,2-dihydropyridin-4-yl)-2-(4-fluoro-2-methylphenoxy)-4-(trifluoromethyl)benzamide

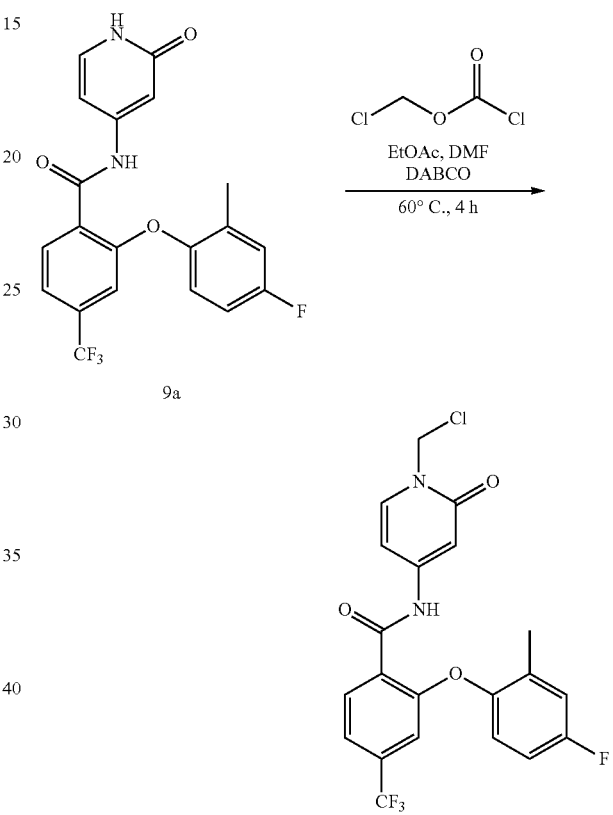

To a 50 liter jacketed glass reactor fitted with an $N_2$ inlet and a mechanical stirrer, and with a jacket temperature set at 20° C., was added 2-(4-fluoro-2-methylphenoxy)-N-(2-oxo-1,2-dihydropyridin-4-yl)-4-(trifluoromethyl)benzamide (9a, 2482.0 g, 6.11 moles, 1.0 eq) under nitrogen. Ethyl acetate (25 liters) was added with stirring at 100 rpm followed by 1,4-diazabicyclo [2.2.2] octane (DABCO) (342.6 g, 3.05 moles, 0.5 eq) and DMF (1.25 liters, Sigma-Aldrich). Chloromethyl chloroformate (815 ml, 9.16 moles, 1.5 eq) was then added over 30 minutes. When the addition of chloromethyl chloroformate was complete, the jacket temperature was ramped up to 60° C. over 30 minutes. The resulting yellow-slurry was stirred for 3 hours at about 60° C., at which time the reaction was judged to be complete by HPLC analysis. The jacket temperature was ramped down to 15° C. over 20 minutes before quenching the reaction by slow addition of water (500 ml) over 10 minutes. Additional water was added, and the mixture stirred at 115 rpm for 15 minutes. Stirring was stopped, the aqueous layer was discarded, and the organic layer washed with water (5 liters), followed by a saturated solution of $NaHCO_3$ (137 g) in water (620 ml). The organic layer was seeded with 5 g of N-(1-

(chloromethyl)-2-oxo-1,2-dihydropyridin-4-yl)-2-(4-fluoro-2-methylphenoxy)-4-(trifluoromethyl)benzamide (7), and the resulting slurry was partially concentrated (removed 18.5 liters of organics) in the rotovap (40° C., vacuum). The resulting suspension was stored at room temperature under nitrogen atmosphere overnight, during which time additional material crystallized out of solution. The remaining solvent was chased with heptanes adding more heptanes as needed to maintain the volume at 10 liters. The thick suspension was stirred on the rotovap at room temperature for 45 minutes, and then the solids were collected by filtration. The off-white solid was washed with heptanes (2.5 liters), then dried in vacuo (40° C., full house vacuum) to give 2409 g (87%) of N-(1-(chloromethyl)-2-oxo-1,2-dihydropyridin-4-yl)-2-(4-fluoro-2-methylphenoxy)-4-(trifluoromethyl)benzamide as an off-white crystalline solid.

Example 15E

Preparation of di-tert-butyl ((4-(2-(4-fluoro-2-methylphenoxy)-4-(trifluoromethyl)benzamido)-2-oxopyridin-1(2H)-yl)methyl) phosphate (20)

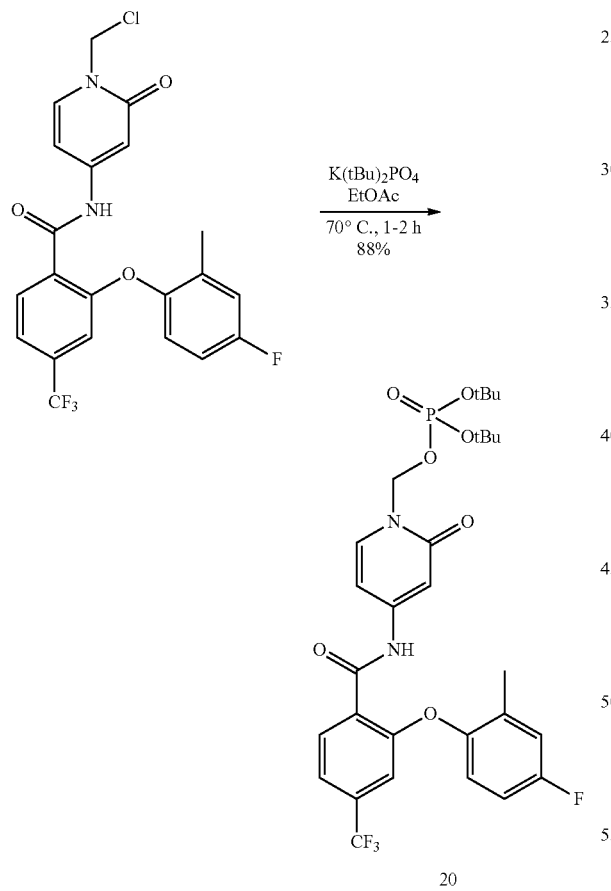

To a 50 liter jacketed glass reactor fitted with an N₂ inlet and a mechanical stirrer, and with a jacket temperature set at 41° C., was added N-(1-(chloromethyl)-2-oxo-1,2-dihydropyridin-4-yl)-2-(4-fluoro-2-methylphenoxy)-4-(trifluoromethyl)benzamide (1199.5 g, 2.64 moles, 1.0 eq) under nitrogen. Ethyl acetate (12 liters) was added with stirring to produce a suspension. To the mixture was added potassium di-tert-butylphosphate (792.7 g @ 95% purity, 3.03 moles, 1.15 eq), then TBAI (9.7 g, 0.026 moles, 0.01 eq), and the jacket temperature was ramped to 71° C. over 20 minutes. The resulting gelatinous suspension was stirred for 4.5 hours at which point HPLC analysis indicated that the reaction was complete. The jacket temperature was ramped to 30° C. over 15 minutes, and then water (6 liters) was added with stirring. The aqueous layer was drained off, and then the organic layer was washed twice with water (1×3.6 liters, then 1×2.4 liters). The organic layer was concentrated down to 3.0-3.5 volumes at 40° C. using a rotovap. Heptane (1.8 liters) was added as an antisolvent, and then the bath heater of the rotovap was turned off, and the mixture was allowed to cool to room temp and was stirred at 40 rpm overnight. The solids were collected by filtration, rinsed with heptanes (1.2 liters), and then dried in vacuo at 45° C. to give 1417.7 g (88%) of di-tert-butyl ((4-(2-(4-fluoro-2-methylphenoxy)-4-(trifluoromethyl)benzamido)-2-oxopyridin-1(2H)-yl)methyl) phosphate (20) as a crystalline, light amber solid.

Example 15F

Preparation of (4-(2-(4-fluoro-2-methylphenoxy)-4-(trifluoromethyl)benzamido)-2-oxopyridin-1(2H)-yl) methyl dihydrogen phosphate (9)

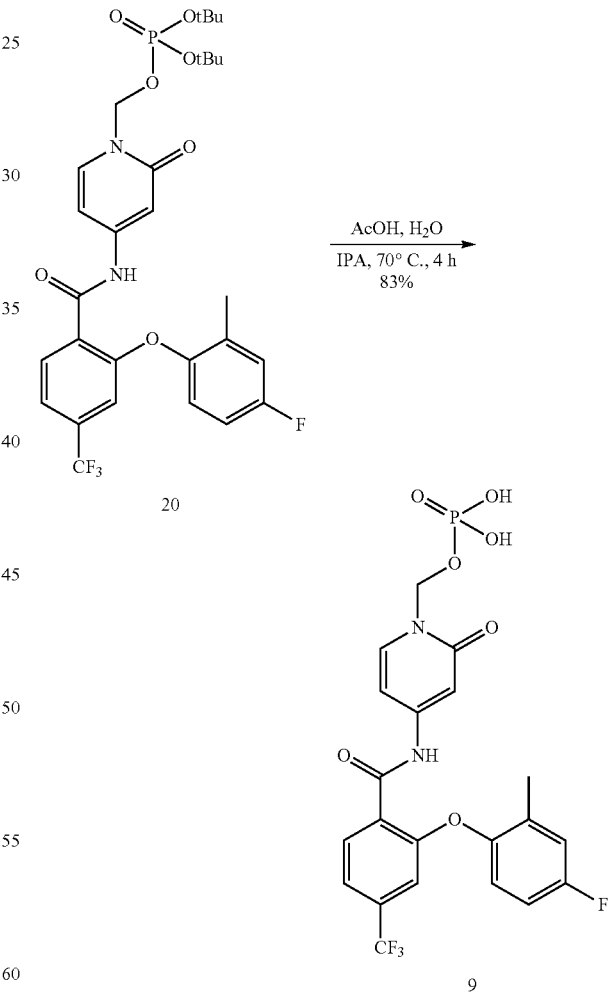

To a 72 liter jacketed glass reactor fitted with an N₂ inlet and a mechanical stirrer, and with a jacket temperature set at 40° C., was added di-tert-butyl ((4-(2-(4-fluoro-2-methylphenoxy)-4-(trifluoromethyl)benzamido)-2-oxopyridin-1 (2H)-yl)methyl) phosphate (20, 2820.9 g, 4.49 moles, 1.0 eq) and isopropyl alcohol (25.4 liters, 9.0 volumes). The mixture was stirred at 200 rpm, and acetic acid (14.1 liters, 5.0 volumes) was added, resulting in a clear solution. The clear solution was polish filtered and transferred to a 50 liter jacketed glass reactor system with stirring at 100 rpm. Water (5.6 liters) was added, and the jacket temperature was ramped to 71° C. over 20 minutes. After 4.5 hours of stirring and heating, HPLC analysis indicated that the reaction was complete. The jacket temperature was ramped down to 19° C. over 3 hours, and the product began crystallizing out of solution. The solid was collected by filtration, rinsed with acetone (5 liters). The solid was added back into the reactor vessel, acetone was added (8.5 liters), the jacket temperature was ramped to 45° C. over 10 minutes, and the suspension was stirred. After 40 minutes, the jacket temperature was ramped to 20° C. over 30 minutes, and the crystalline solid was collected by filtration, rinsed with acetone (5 liters) and dried in vacuo at 50° C. to give 1917.7 g (83%) of (4-(2-(4-fluoro-2-methylphenoxy)-4-(trifluoromethyl)benzamido)-2-oxopyridin-1(2H)-yl)methyl dihydrogen phosphate (9) as a crystalline white solid.

Example 15G

Preparation of N-[1-(chloromethyl)-2-oxo-4-pyridyl]-2-(4-fluoro-2-methyl-phenoxy)-4-(trifluoromethyl)benzamide (21)

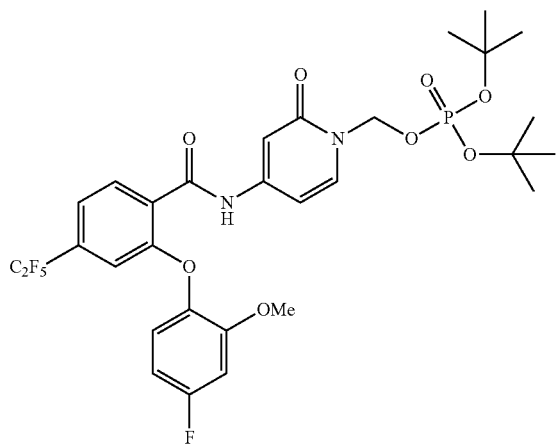

A solution of 2-(4-fluoro-2-methoxy-phenoxy)-N-(2-oxo-1H-pyridin-4-yl)-4-(1,1,2,2,2-pentafluoroethyl)benzamide (2a) (99.9 mg, 0.2115 mmol) and chloromethyl chloroformate (32.73 mg, 22.04 µL, 0.2538 mmol) in DCM (900 µL) and DMF (100 µL) was stirred at room temperature for 4 hours (gas evolved). The reaction mixture was diluted with EtOAc, the organic phase washed with sat. aq. NaHCO₃, brine, dried with Na₂SO₄ and evaporated to dryness. The residue was taken up in DMF (999 µL), di-tert-butoxyphosphoryloxypotassium (105.0 mg, 0.4230 mmol) and tetrabutylammonium iodide (7.81 mg, 0.021 mmol) were added and the reaction mixture was stirred at 70° C. for 4 hours. The reaction mixture was cooled, diluted with water and extracted with EtOAc (3×). The organics were combined, washed with water then brine, dried with Na₂SO₄ and evaporated to dryness. Purification by column chromatography (4 g silica; 0-100% EtOAc in hexanes) gave di-tert-butyl [4-[[2-(4-fluoro-2-methoxy-phenoxy)-4-(1,1,2,2,2-pentafluoroethyl)benzoyl]amino]-2-oxo-1-pyridyl]methyl phosphate (21) (35 mg, 0.05039 mmol, 23.8%) as a clear oil. ESI-MS m/z calc. 694.18787, found 695.4 (M+1)+; Retention time: 0.78.

Example 15H

Preparation of N-[1-(chloromethyl)-2-oxo-4-pyridyl]-2-(4-fluoro-2-methyl-phenoxy)-4-(trifluoromethyl)benzamide (2)

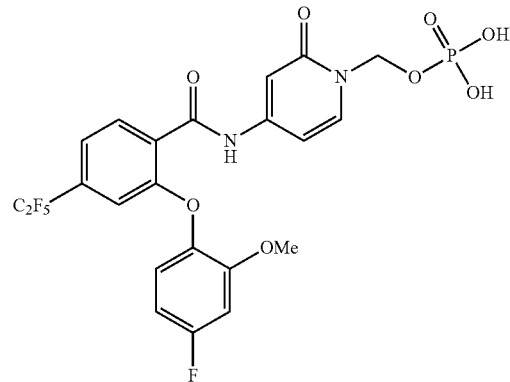

A solution of ditert-butyl [4-[[2-(4-fluoro-2-methoxy-phenoxy)-4-(1,1,2,2,2-pentafluoroethyl)benzoyl]amino]-2-oxo-1-pyridyl]methyl phosphate (21) (35 mg, 0.05039 mmol) in CH₃CN (700.0 µL), water (700.0 µL) and AcOH (700.0 µL) was refluxed for 1 hour then evaporated to dryness. The material was then co-evaporated with CH₃CN (3×), triturated with CH₃CN, filtered, washed with CH₃CN and desiccated to give [4-[[2-(4-fluoro-2-methoxy-phenoxy)-4-(1,1,2,2,2-pentafluoroethyl)benzoyl]amino]-2-oxo-1-pyridyl]methyl dihydrogen phosphate (2) (13 mg, 0.02210 mmol, 43.9%) as a white solid. $^1$H NMR (400 MHz, DMSO-d₆) δ 10.72 (s, 1H), 7.85 (d, J=8.0 Hz, 1H), 7.63 (d, J=7.6 Hz, 1H), 7.51 (d, J=8.2 Hz, 1H), 7.31 (dd, J=8.9, 5.9 Hz, 1H), 7.16 (dd, J=10.7, 2.9 Hz, 1H), 6.94 (d, J=1.9 Hz, 1H), 6.91-6.84 (m, 1H), 6.77 (s, 1H), 6.47 (dd, J=7.6, 2.2 Hz, 1H), 5.54 (d, J=9.7 Hz, 2H), 3.74 (s, 3H) ppm. $^{31}$P NMR (162 MHz, DMSO-d₆–85% H₃PO₄ aq. as internal standard–0 ppm) δ -1.93 (t, J=9.7 Hz, 1H) ppm.

Example 15I

Di-tert-butyl [4-[[2-(4-fluorophenoxy)-5-(trifluoromethyl)benzoyl]amino]-2-oxo-1-pyridyl]methyl phosphate (22)

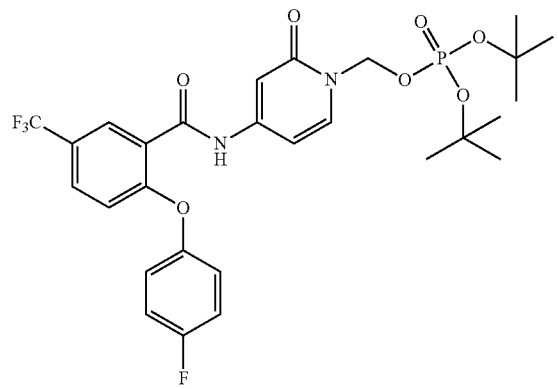 [SMILES: CC(C)(C)OP(=O)(OCn1ccc(NC(=O)c2cc(C(F)(F)F)ccc2Oc2ccc(F)cc2)cc1=O)OC(C)(C)C]

A solution of 2-(4-fluorophenoxy)-N-(2-oxo-1H-pyridin-4-yl)-5-(trifluoromethyl)benzamide (18a) (98 mg, 0.2498 mmol) and chloromethyl chloroformate (38.66 mg, 26.39 µL, 0.2998 mmol) in CH$_2$Cl$_2$ (1 mL) and DMF (100 µL) was stirred at room temperature for 4 hours (gas evolved). The reaction mixture was diluted with EtOAc and the organic phase washed with sat. aq. NaHCO$_3$, brine, dried with Na$_2$SO$_4$ and evaporated to dryness. The residue was taken up in DMF (1 mL), di-tert-butoxyphosphoryloxypotassium (124.0 mg, 0.4996 mmol) and tetrabutylammonium iodide (9.227 mg, 0.02498 mmol) were added and the reaction mixture was stirred at 70° C. for 4 hours. The reaction mixture was cooled, diluted with water and extracted with EtOAc (3×). The organic layers were combined, washed with water then brine, dried with Na$_2$SO$_4$ and evaporated to dryness. Purification by column chromatography (4 g silica; 0-100% EtOAc in Hx) gave di-tert-butyl [4-[[2-(4-fluorophenoxy)-5-(trifluoromethyl)benzoyl]amino]-2-oxo-1-pyridyl]methyl phosphate (22) (67 mg, 0.1090 mmol, 43.7%) as a clear oil. ESI-MS m/z calc. 614.1805, found 615.5 (M+1)+; Retention time: 0.73 minutes.

Example 15J

[4-[[2-(4-Fluorophenoxy)-5-(trifluoromethyl)benzoyl]amino]-2-oxo-1-pyridyl]methyl dihydrogen phosphate (18)

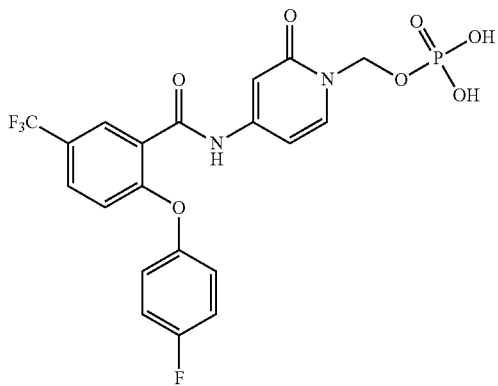 [SMILES: O=C(Nc1ccn(COP(=O)(O)O)c(=O)c1)c1cc(C(F)(F)F)ccc1Oc1ccc(F)cc1]

A solution of di-tert-butyl [4-[[2-(4-fluorophenoxy)-5-(trifluoromethyl)benzoyl]amino]-2-oxo-1-pyridyl]methyl phosphate (22) (67 mg, 0.1090 mmol) in CH$_3$CN (1.340 mL), water (1.340 mL) and AcOH (1.340 mL) was refluxed for 1 hour then evaporated to dryness. The material was then co-evaporated with CH$_3$CN (3×), triturated with CH$_3$CN, filtered, washed with CH$_3$CN and desiccated to give [4-[[2-(4-fluorophenoxy)-5-(trifluoromethyl)benzoyl]amino]-2-oxo-1-pyridyl]methyl dihydrogen phosphate (18) (32 mg, 0.06052 mmol, 55.5%) as a white solid. ESI-MS m/z calc. 502.0553, found 503.4 (M+1)+; Retention time: 1.39 minutes. $^1$H NMR (400 MHz, DMSO-d$_6$) δ 10.70 (s, 1H), 8.00 (d, J=2.4 Hz, 1H), 7.83 (dd, J=8.8, 2.4 Hz, 1H), 7.61 (d, J=7.6 Hz, 1H), 7.35-7.23 (m, 4H), 7.00 (d, J=8.7 Hz, 1H), 6.91 (d, J=2.2 Hz, 1H), 6.45 (dd, J=7.6, 2.3 Hz, 1H), 5.53 (d, J=9.7 Hz, 2H) ppm. $^{31}$P NMR (162 MHz, DMSO-d$_6$–85% H$_3$PO$_4$ aq. as internal standard–0 ppm) δ–2.11 (t, J=9.6 Hz) ppm.

Example 15K

Di-tert-butyl [4-[[4-chloro-2-(4-fluoro-2-methyl-phenoxy)benzoyl]amino]-2-oxo-1-pyridyl]methyl phosphate (23)

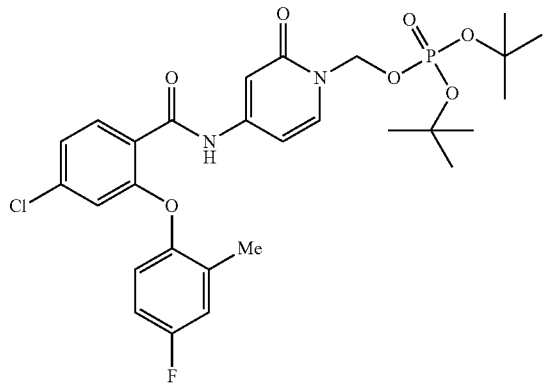 [SMILES: Cc1cc(F)ccc1Oc1cc(Cl)ccc1C(=O)Nc1ccn(COP(=O)(OC(C)(C)C)OC(C)(C)C)c(=O)c1]

A solution of 4-chloro-2-(4-fluoro-2-methyl-phenoxy)-N-(2-oxo-1H-pyridin-4-yl)benzamide (13a) (99 mg, 0.2656 mmol) and chloromethyl chloroformate (82.19 mg, 55.35 µL, 0.6374 mmol) in THF (2 mL) was added DMF (0.2 mL) and CH$_2$Cl$_2$ (0.5 mL) and was stirred at room temperature for 2 hours. The reaction mixture was diluted with EtOAc and the organic phase washed with sat. aq. NaHCO$_3$, brine, dried with Na$_2$SO$_4$ and evaporated to dryness. The residue was taken up in DMF (1 mL), di-tert-butoxyphosphoryloxypotassium (263.7 mg, 1.062 mmol) and tetrabutylammonium iodide (9.810 mg, 0.02656 mmol) were added and the reaction mixture was stirred at 70° C. for 4 hours. The reaction mixture was cooled, diluted with water and extracted with EtOAc (3×). The organic phases were combined, washed with water then brine, dried with Na$_2$SO$_4$ and evaporated to dryness. Purification by column chromatography (12 g silica; 0-100% EtOAc in Hx) gave di-tert-butyl [4-[[4-chloro-2-(4-fluoro-2-methyl-phenoxy)benzoyl]amino]-2-oxo-1-pyridyl]methyl phosphate (23) (35 mg, 0.05882 mmol, 22.2%) as a clear foam. ESI-MS m/z calc. 594.1698, found 595.5 (M+1)+; Retention time: 0.77 minutes.

Example 15L

[4-[[4-Chloro-2-(4-fluoro-2-methyl-phenoxy)benzoyl]amino]-2-oxo-1-pyridyl]methyl dihydrogen phosphate (13)

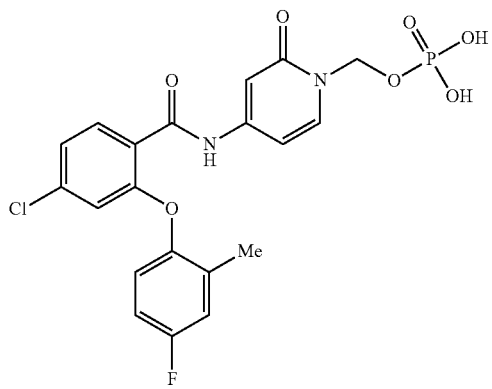 [SMILES: Cc1cc(F)ccc1Oc1cc(Cl)ccc1C(=O)Nc1ccn(COP(=O)(O)O)c(=O)c1]

A solution of di-tert-butyl [4-[[4-chloro-2-(4-fluoro-2-methyl-phenoxy)benzoyl]amino]-2-oxo-1-pyridyl]methyl phosphate (23) (35 mg, 0.05882 mmol) in CH₃CN (700.0 μL), water (700.0 μL) and AcOH (0.7 mL, 12.31 mmol) was heated at 90° C. for 20 min then evaporated and co-evaporated with CH₃CN (3×). The material was triturated with CH₃CN, filtered, washed with CH₃CN and desiccated to give [4-[[4-chloro-2-(4-fluoro-2-methyl-phenoxy)benzoyl]amino]-2-oxo-1-pyridyl]methyl dihydrogen phosphate (13) (13 mg, 0.02558 mmol, 43.5%) as a white solid. ESI-MS m/z calc. 482.0446, found 483.4 (M+1)+; Retention time: 1.41 minutes. ¹H NMR (400 MHz, DMSO-d₆) δ 10.59 (s, 1H), 7.66 (d, J=8.2 Hz, 1H), 7.60 (d, J=7.5 Hz, 1H), 7.30 (dd, J=8.2, 2.0 Hz, 1H), 7.21 (d, J=9.3 Hz, 1H), 7.16-7.05 (m, 2H), 6.89 (d, J=2.3 Hz, 1H), 6.74 (d, J=2.0 Hz, 1H), 6.44 (dd, J=7.6, 2.3 Hz, 1H), 5.51 (d, J=9.7 Hz, 2H), 2.16 (s, 3H) ppm. ³¹P NMR (162 MHz, DMSO-d₆-85% H₃PO₄ aq. as internal standard–0 ppm) δ–2.15 (t, J=9.7 Hz) ppm.

Example 15M

Di-tert-butyl [4-[[2-(4-fluoro-2-methyl-phenoxy)-5-(trifluoromethyl)benzoyl]amino]-2-oxo-1-pyridyl]methyl phosphate (24)

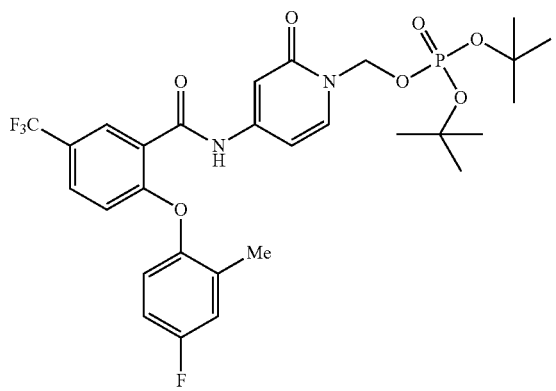 [SMILES: Cc1cc(F)ccc1Oc1ccc(C(F)(F)F)cc1C(=O)Nc1ccn(COP(=O)(OC(C)(C)C)OC(C)(C)C)c(=O)c1]

To a solution of 2-(4-fluoro-2-methyl-phenoxy)-N-(2-oxo-1H-pyridin-4-yl)-5-(trifluoromethyl)benzamide (10a) (102 mg, 0.2510 mmol) and chloromethyl chloroformate (77.67 mg, 52.30 μL, 0.6024 mmol) in CH₂Cl₂ (2 mL) was added DMF (200 μL) and the reaction mixture was stirred at room temperature for 1 hour. At this time, more chloromethyl chloroformate (77.67 mg, 52.30 μL, 0.6024 mmol) was added and the reaction mixture was heated to 70° C. for 25 min. The reaction mixture was diluted with EtOAc, the organic phase washed with sat. aq. NaHCO₃, brine, dried with Na₂SO₄ and evaporated to dryness. The residue was taken up in DMF (3 mL), di-tert-butoxyphosphoryloxypotassium (249.3 mg, 1.004 mmol) and tetrabutylammonium iodide (9.271 mg, 0.02510 mmol) were added and the reaction mixture was stirred at 70° C. for 4 hours. The reaction mixture was cooled, diluted with water and extracted with EtOAc (3×). The organic layers were combined, washed with water then brine, dried with Na₂SO₄ and evaporated to dryness. Purification by column chromatography (12 g silica; 0-100% EtOAc in Hx) gave di-tert-butyl [4-[[2-(4-fluoro-2-methyl-phenoxy)-5-(trifluoromethyl)benzoyl]amino]-2-oxo-1-pyridyl]methyl phosphate (24) (23 mg, 0.03659 mmol, 14.6%) as a clear glass. ESI-MS m/z calc. 628.19617, found 629.5 (M+1)+; Retention time: 0.78 minutes.

Example 15N

[4-[[2-(4-Fluoro-2-methyl-phenoxy)-5-(trifluoromethyl)benzoyl]amino]-2-oxo-1-pyridyl]methyl dihydrogen phosphate (10)

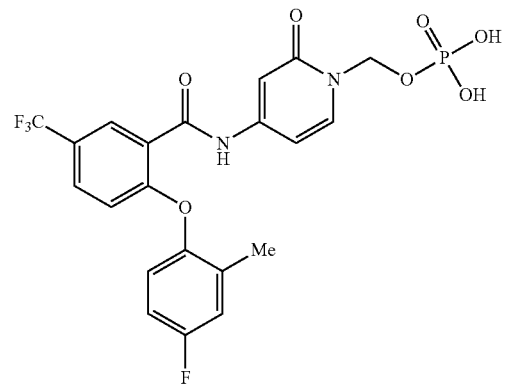 [SMILES: Cc1cc(F)ccc1Oc1ccc(C(F)(F)F)cc1C(=O)Nc1ccn(COP(=O)(O)O)c(=O)c1]

A solution of di-tert-butyl [4-[[2-(4-fluoro-2-methyl-phenoxy)-5-(trifluoromethyl)benzoyl]amino]-2-oxo-1-pyridyl]methyl phosphate (24) (23 mg, 0.03659 mmol) in CH₃CN (460.0 μL), water (460.0 μL) and AcOH (460.0 μL) was heated at 90° C. for 15 min then evaporated and co-evaporated with CH₃CN (3×). The material was triturated with CH₃CN, filtered, washed with CH₃CN and desiccated to give [4-[[2-(4-fluoro-2-methyl-phenoxy)-5-(trifluoromethyl)benzoyl]amino]-2-oxo-1-pyridyl]methyl dihydrogen phosphate (10) (6 mg, 0.01104 mmol, 30.2%) as a white solid. ESI-MS m/z calc. 516.0709, found 517.4 (M+1)+; Retention time: 1.45 minutes. ¹H NMR (400 MHz, DMSO-d₆) δ 11.14 (s, 1H), 8.42 (d, J=2.4 Hz, 1H), 8.22 (dd, J=8.8, 2.2 Hz, 1H), 8.05 (d, J=7.6 Hz, 1H), 7.67 (dd, J=9.5, 3.1 Hz, 1H), 7.65-7.50 (m, 2H), 7.35 (d, J=2.3 Hz, 1H), 7.26 (d, J=8.7 Hz, 1H), 6.88 (dd, J=7.6, 2.4 Hz, 1H), 5.95 (d, J=9.8 Hz, 2H), 2.57 (s, 3H) ppm. ³¹P NMR (162 MHz, DMSO-d₆–85% H₃PO₄ aq. as internal standard–0 ppm) δ–2.17 (t, J=9.7 Hz) ppm.

Example 15O

Di-tert-butyl [4-[[4,5-dichloro-2-(4-fluoro-2-methoxy-phenoxy)benzoyl]amino]-2-oxo-1-pyridyl]methyl phosphate (25)

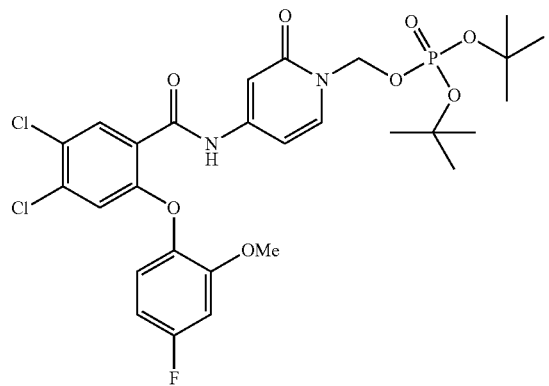 [SMILES: COc1cc(F)ccc1Oc1cc(Cl)c(Cl)cc1C(=O)Nc1ccn(COP(=O)(OC(C)(C)C)OC(C)(C)C)c(=O)c1]

To a solution of 4,5-dichloro-2-(4-fluoro-2-methoxy-phenoxy)-N-(2-oxo-1H-pyridin-4-yl)benzamide (1a) (101 mg, 0.2386 mmol) and chloromethyl chloroformate (36.92 mg, 24.86 µL, 0.2863 mmol) in CH$_2$Cl$_2$ (2 mL) was added DMF (200 µL) and the reaction mixture was stirred at room temperature for 1 hour. At this time, THF (1 mL) was added followed by more chloromethyl chloroformate (36.92 mg, 24.86 µL, 0.2863 mmol) and the reaction mixture stirred at room temperature for 1 h. More DMF (1 mL) and chloromethyl chloroformate (36.92 mg, 24.86 µL, 0.2863 mmol) was added and the reaction mixture was heated to 70° C. for 15 min. The reaction mixture was diluted with EtOAc and the organic phase washed with sat. aq. NaHCO$_3$, brine, dried with Na$_2$SO$_4$ and evaporated to dryness. The residue was taken up in DMF (1.010 mL), di-tert-butoxyphosphoryloxy-potassium (118.5 mg, 0.4772 mmol) and tetrabutylammonium iodide (8.813 mg, 0.02386 mmol) was added and the reaction mixture stirred at 70° C. for 4 h. The reaction mixture was cooled, diluted with water and extracted with EtOAc (3×). The organic layers were combined, washed with water then brine, dried with Na$_2$SO$_4$ and evaporated to dryness. Purification by column chromatography (12 g silica; 0-100% EtOAc in Hx) gave di-tert-butyl [4-[[4,5-dichloro-2-(4-fluoro-2-methoxy-phenoxy)benzoyl]amino]-2-oxo-1-pyridyl]methyl phosphate (25) (40 mg, 0.06197 mmol, 26.0%) as a clear glass. ESI-MS m/z calc. 644.12573, found 647.3 (M+1)+; Retention time: 0.81 minutes.

Example 15P

[4-[[4,5-Dichloro-2-(4-fluoro-2-methoxy-phenoxy)benzoyl]amino]-2-oxo-1-pyridyl]methyl dihydrogen phosphate (1)

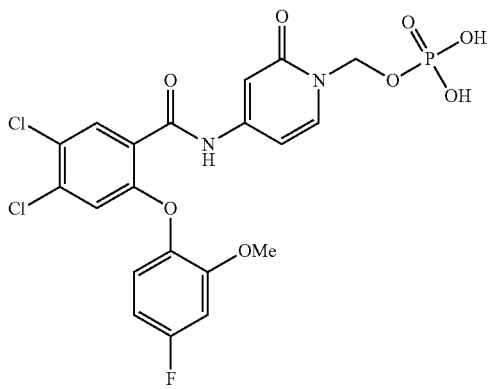 [SMILES: COc1cc(F)ccc1Oc1cc(Cl)c(Cl)cc1C(=O)Nc1ccn(COP(=O)(O)O)c(=O)c1]

A solution of di-tert-butyl [4-[[4,5-dichloro-2-(4-fluoro-2-methoxy-phenoxy)benzoyl]amino]-2-oxo-1-pyridyl]methyl phosphate (40 mg, 0.06197 mmol) in CH$_3$CN (800.0 µL), water (800.0 µL) and AcOH (800 µL, 14.07 mmol) was heated at 90° C. for 15 min then evaporated and co-evaporated with CH$_3$CN (3×). The material was triturated with CH$_3$CN, filtered, washed with CH$_3$CN and desiccated to give [4-[[4,5-dichloro-2-(4-fluoro-2-methoxy-phenoxy)benzoyl]amino]-2-oxo-1-pyridyl]methyl dihydrogen phosphate (1) (19 mg, 0.03385 mmol, 54.6%) as a white solid. ESI-MS m/z calc. 532.00055, found 533.3 (M+1)+; Retention time: 1.5 minutes. $^1$H NMR (400 MHz, DMSO-d$_6$) δ 10.58 (s, 1H), 7.91 (s, 1H), 7.62 (d, J=7.6 Hz, 1H), 7.27 (dd, J=8.9, 5.8 Hz, 1H), 7.13 (dd, J=10.7, 3.0 Hz, 1H), 6.90 (d, J=2.3 Hz, 1H), 6.86 (s, 1H), 6.86-6.81 (m, 1H), 6.44 (dd, J=7.6, 2.4 Hz, 1H), 5.52 (d, J=9.7 Hz, 2H), 3.76 (s, 3H) ppm. $^{31}$P NMR (162 MHz, DMSO-d$_6$–85% H$_3$PO$_4$ aq. as internal standard–0 ppm) δ–2.12 (t, J=9.4 Hz) ppm.

Compounds 3-8, 11, 12 and 14-17 may be prepared using similar procedures as described above for preparing compounds 1, 2, 9, 10, 13 and 18.

Example 15Q

A spray dry dispersion of compound 9 with 50% HPMCAS was prepared as follows. Compound 9 (14 grams) was added to a beaker (1000 ml), followed by 400 mL of THF/H$_2$O (95:5) and 100 mL of MeOH. The material was stirred for 1 h giving a slightly hazy solution. In a separate container, 14 grams of Hydroxypropylmethylcellulose acetate succinate HF grade (HPMCAS-HF) was dissolved in 100 mL of THF and the mixture was stirred for 15 minutes. The two solutions were combined and stirred continuously while spray drying using a Buchi Mini Spray Dryer with the following parameters:

| | |
|---|---|
| T inlet (setpoint) | 78° C. |
| T outlet (start) | 38° C. |
| T outlet (end) | 35° C. |
| Nitrogen Pressure | 75 psi |
| Aspirator | 100% |
| Pump | 20% |
| Rotometer | 60 mm |
| Filter Pressure | −50 mbar |
| Condenser Temp | −5° C. |
| Run Time | 3 h |

Approximately 18.2 g of compound 9 amorphous Form C as a spray dry dispersion (65% yield) was recovered. The amorphous Form C of compound 9 in the spray dry dispersion was confirmed by XRPD (FIG. 5) and DSC, showing a glass transition temperature of 96° C.

Figure 6:
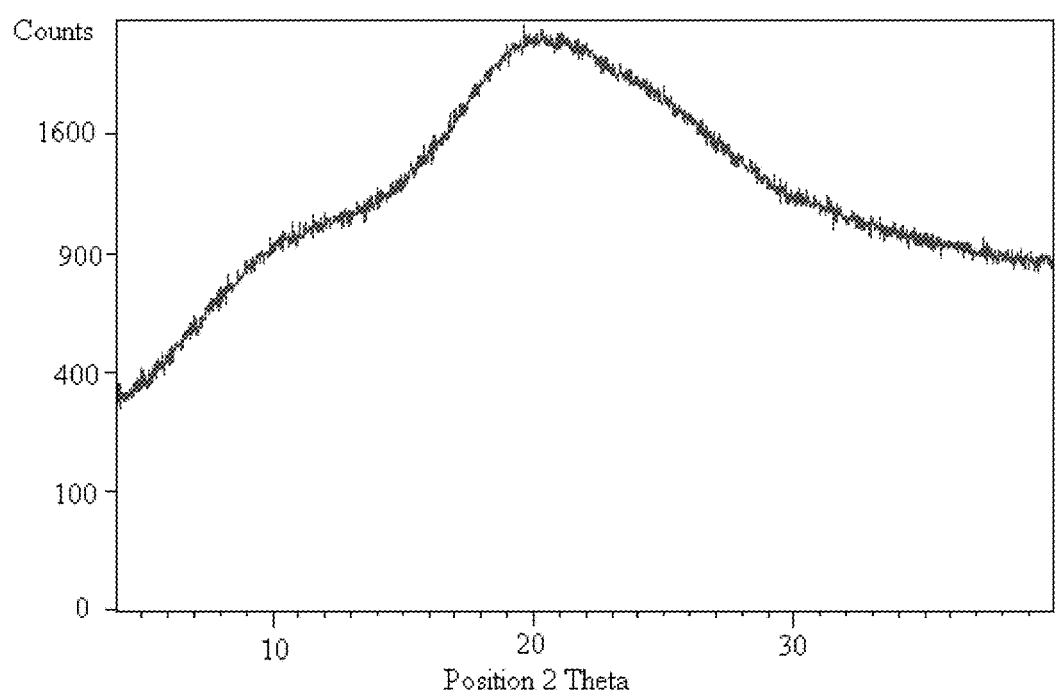
FIG. 6 shows an X-ray powder diffraction pattern of amorphous Form C from a spray dry dispersion of (4-(2-(4-fluoro-2-methylphenoxy)-4-(trifluoromethyl)benzamido)-2-oxopyridin-1(2H)-yl)methyl dihydrogen phosphate.

A neat amorphous Form C of compound 9 was prepared by spray dry dispersion according to the conditions discussed above except that no HPMCAS polymer was added. The neat amorphous Form C of compound 9 in the spray dry dispersion was confirmed by XRPD (FIG. 6).

The structure of crystalline Form B of compound 9 was confirmed by single-crystal x-ray diffraction analysis (FIG. 1). Single crystal diffraction data was acquired on a Bruker Apex II diffractometer equipped with sealed tube Cu K-alpha source (Cu Kα radiation, γ=1.54178 Å) and an Apex II CCD detector. A colorless plate shaped crystal with dimensions of 0.01×0.05×0.05 mm was selected for data collection. Three batches of 40 frames separated in reciprocal space were obtained to provide an orientation matrix and initial cell parameters. Final cell parameters were obtained and refined after data collection was completed based on the full data set.

A diffraction data set of reciprocal space was obtained to a resolution of 0.84 Å using 1.0° steps using 60 seconds exposures for each low angle frame and 120 seconds for each high angle frame. Observation of the crystal after data collection showed no signs of decomposition.

The data was collected, refined and reduced using the Bruker Apex software. The structure was solved using the SHELXS97 (Sheldrick, 1990); program(s) and the structure refined using the SHELXL97 (Sheldrick, 1997) program. The crystal shows monoclinic cell with P2$_1$/c space group. The lattice parameters are a=20.194(9)Å, b=9.205(4)Å, c=11.956(5)Å, β=95.213(8)°. Volume=2213.4(17)Å$^3$. The high angle reflections were weak, leading to a high R factor 9.8%. However, the structure was ordered and there was one symmetry independent molecule in the structure.

TABLE 3

Analytical data for Compounds and Intermediates

| Cmpd. No. | LCMS Ret. Time in minutes | MS (M + 1) | $^1$H-NMR (400 MHz) |
|---|---|---|---|
| 1 | 1.50 | 533.3 | (DMSO-d$_6$) δ 10.58 (s, 1H), 7.91 (s, 1H), 7.62 (d, J = 7.6 Hz, 1H), 7.27 (dd, J = 8.9, 5.8 Hz, 1H), 7.13 (dd, J = 10.7, 3.0 Hz, 1H), 6.90 (d, J = 2.3 Hz, 1H), 6.86 (s, 1H), 6.86-6.81 (m, 1H), 6.44 (dd, J = 7.6, 2.4 Hz, 1H), 5.52 (d, J = 9.7 Hz, 2H), 3.76 (s, 3H) ppm |
| 1a | 1.57 | 423.3 | (DMSO-d$_6$) δ 11.27 (s, 1H), 10.49 (s, 1H), 7.90 (br s, 1H), 7.32 (d, J = 7.2 Hz, 1H), 7.28 (dd, J = 8.9, 5.8 Hz, 1H), 7.14 (dd, J = 10.7, 2.9 Hz, 1H), 6.89-6.82 (m, 2H), 6.77 (s, 1H), 6.39 (dd, J = 7.2, 2.1 Hz, 1H), 3.76 (s, 3H) ppm |
| 2 | 1.54 | 583.4 | (DMSO-d$_6$) δ 10.72 (s, 1H), 7.85 (d, J = 8.0 Hz, 1H), 7.63 (d, J = 7.6 Hz, 1H), 7.51 (d, J = 8.2 Hz, 1H), 7.31 (dd, J = 8.9, 5.9 Hz, 1H), 7.16 (dd, J = 10.7, 2.9 Hz, 1H), 6.94 (d, J = 1.9 Hz, 1H), 6.91-6.84 (m, 1H), 6.77 (s, 1H), 6.47 (dd, J = 7.6, 2.2 Hz, 1H), 5.54 (d, J = 9.7 Hz, 2H), 3.74 (s, 3H) ppm |
| 2a | 1.62 | 473.3 | (DMSO-d$_6$) δ 11.32 (s, 1H), 10.62 (s, 1H), 7.83 (d, J = 7.9 Hz, 1H), 7.51 (d, J = 7.9 Hz, 1H), 7.39-7.27 (m, 2H), 7.17 (dd, J = 10.7, 2.8 Hz, 1H), 6.88 (dd, J = 11.3, 5.7 Hz, 1H), 6.81 (s, 1H), 6.75 (s, 1H), 6.43 (d, J = 7.1 Hz, 1H), 3.73 (s, 3H) ppm |
| 3a | 1.53 | 393.1 | (DMSO-d$_6$) δ 11.32 (s, 1H), 10.57 (s, 1H), 7.95 (s, 1H), 7.34-7.24 (m, 3H), 7.22-7.15 (m, 3H), 6.74 (s, 1H), 6.38 (d, J = 7.2 Hz, 1H) ppm |
| 4a | 1.56 | 423.2 | |
| 5a | 1.8 | 459.5 | |
| 6a | 1.59 | 443.5 | (DMSO-d$_6$) δ 7.87 (d, J = 7.9 Hz, 1H), 7.59 (d, J = 7.6 Hz, 1H), 7.37-7.25 (m, 3H), 7.24-7.16 (m, 2H), 7.07 (s, 1H), 6.73 (s, 1H), 6.37 (d, J = 6.9 Hz, 1H) ppm |
| 7a | 1.52 | 389.1 | |
| 8a | 1.93 | 459.3 | (DMSO-d$_6$) δ 11.29 (s, 1H), 10.62 (s, 1H), 8.02 (d, J = 2.3 Hz, 1H), 7.86 (dd, J = 8.7, 2.4 Hz, 1H), 7.58-7.40 (m, 2H), 7.40-7.21 (m, 3H), 7.11 (d, J = 8.7 Hz, 1H), 6.76 (d, J = 2.1 Hz, 1H), 6.38 (dd, J = 7.2, 2.1 Hz, 1H) ppm |
| 9 | 1.79 | 407.1 | (DMSO-d$_6$) δ 11.27 (s, 1H), 10.63 (s, 1H), 7.84 (d, J = 7.8 Hz, 1H), 7.60 (d, J = 7.8 Hz, 1H), 7.31 (d, J = 7.2 Hz, 1H), 7.23 (m, 1H), 7.10 (m, 2H), 6.97 (s, 1H), 6.76 (d, J = 1.6 Hz, 1H), 6.38 (dd, J = 7.2, 2.0 Hz, 1H), 2.16 (s, 3H) ppm |
| 9a | 1.79 | 407.1 | (DMSO-d$_6$) δ 11.27 (s, 1H), 10.63 (s, 1H), 7.84 (d, J = 7.8 Hz, 1H), 7.60 (d, J = 7.8 Hz, 1H), 7.31 (d, J = 7.2 Hz, 1H), 7.23 (m, 1H), 7.10 (m, 2H), 6.97 (s, 1H), 6.76 (d, J = 1.6 Hz, 1H), 6.38 (dd, J = 7.2, 2.0 Hz, 1H), 2.16 (s, 3H) ppm |
| 10 | 1.45 | 517.4 | (DMSO-d$_6$) δ 11.14 (s, 1H), 8.42 (d, J = 2.4 Hz, 1H), 8.22 (dd, J = 8.8, 2.2 Hz, 1H), 8.05 (d, J = 7.6 Hz, 1H), 7.67 (dd, J = 9.5, 3.1 Hz, 1H), 7.65-7.50 (m, 2H), 7.35 (d, J = 2.3 Hz, 1H), 7.26 (d, J = 8.7 Hz, 1H), 6.88 (dd, J = 7.6, 2.4 Hz, 1H), 5.95 (d, J = 9.8 Hz, 2H), 2.57 (s, 3H) ppm |
| 10a | 1.6 | 407.2 | (DMSO-d$_6$) δ 11.77 (s, 1H), 10.79 (s, 1H), 8.00 (d, J = 2.2 Hz, 1H), 7.80 (dd, J = 8.8, 2.3 Hz, 1H), 7.45 (d, J = 7.2 Hz, 1H), 7.25 (dd, J = 9.3, 3.0 Hz, 1H), 7.16 (m, 2H), 6.95 (d, J = 1.9 Hz, 1H), 6.83 (d, J = 8.7 Hz, 1H), 6.56 (dd, J = 7.2, 2.0 Hz, 1H), 2.14(s, 3H) ppm |
| 11a | 1.57 | 427.2 | (DMSO-d$_6$) δ 11.29 (s, 1H), 10.62 (s, 1H), 8.02 (d, J = 2.2 Hz, 1H), 7.83 (dd, J = 8.8, 2.2 Hz, 1H), 7.69 (dd, J = 8.4, 3.0 Hz, 1H), 7.45 (dd, J = 9.1, 5.3 Hz, 1H), 7.40-7.30 (m, 2H), 6.92 (d, J = 8.7 Hz, 1H), 6.79 (d, J = 1.9 Hz, 1H), 6.42 (dd, J = 7.2, 2.1 Hz, 1H) ppm |
| 12a | 1.57 | 373.1 | |
| 13 | 1.41 | 483.4 | (DMSO-d$_6$) δ 10.59 (s, 1H), 7.66 (d, J = 8.2 Hz, 1H), 7.60 (d, J = 7.5 Hz, 1H), 7.30 (dd, J = 8.2, 2.0 Hz, 1H), 7.21 (d, J = 9.3 Hz, 1H), 7.16-7.05 (m, 2H), 6.89 (d, J = 2.3 Hz, 1H), 6.74 (d, J = 2.0 Hz, 1H), 6.44 (dd, J = 7.6, 2.3 Hz, 1H), 5.51 (d, J = 9.7 Hz, 2H), 2.16 (s, 3H) ppm. |
| 13a | 1.57 | 373.2 | (DMSO-d$_6$) δ 11.48 (s, 1H), 10.57 (s, 1H), 7.65 (d, J = 8.2 Hz, 1H), 7.36 (d, J = 7.2 Hz, 1H), 7.30 (dd, J = 8.2, 1.9 Hz, 1H), 7.21 (d, J = 9.3 Hz, 1H), 7.10 (m, 2H), 6.83 (d, J = 1.9 Hz, 1H), 6.74 (d, J = 1.9 Hz, 1H), 6.45 (dd, J = 7.2, 2.1 Hz, 1H), 2.16 (s, 3H) ppm |
| 14a | 1.64 | 393.1 | |
| 15a | 1.48 | 359.2 | (DMSO-d$_6$) δ 11.25 (s, 1H), 10.48 (s, 1H), 7.65 (t, J = 8.5 Hz, 1H), 7.29 (m, 4H), 7.19 (m, 2H), 6.91 (d, J = 1.9 Hz, 1H), 6.75 (d, J = 1.9 Hz, 1H), 6.38 (dd, J = 7.2, 2.1 Hz, 1H) ppm |

TABLE 3-continued

Analytical data for Compounds and Intermediates

| Cmpd. No. | LCMS Ret. Time in minutes | MS (M + 1) | $^1$H-NMR (400 MHz) |
|---|---|---|---|
| 16a | 1.55 | 411.17 | |
| 17a | 1.83 | 459.3 | (DMSO-$d_6$) δ 11.28 (s, 1H), 10.63 (s, 1H), 8.04 (d, J = 2.3 Hz, 1H), 7.86 (dd, J = 8.7, 2.4 Hz, 1H), 7.60-7.54 (m, 1H), 7.54-7.43 (m, 1H), 7.43-7.34 (m, 1H), 7.34-7.28 (m, 2H), 7.05 (d, J = 8.7 Hz, 1H), 6.75 (d, J = 2.0 Hz, 1H), 6.38 (dd, J = 7.2, 2.1 Hz, 1H) ppm |
| 18 | 1.39 | 503.4 | (DMSO-$d_6$) δ 10.70 (s, 1H), 8.00 (d, J = 2.4 Hz, 1H), 7.83 (dd, J = 8.8, 2.4 Hz, 1H), 7.61 (d, J = 7.6 Hz, 1H), 7.35-7.23 (m, 4H), 7.00 (d, J = 8.7 Hz, 1H), 6.91 (d, J = 2.2 Hz, 1H), 6.45 (dd, J = 7.6, 2.3 Hz, 1H), 5.53 (d, J = 9.7 Hz, 2H) ppm |
| 18a | 1.72 | 393.1 | (DMSO-$d_6$) δ 11.40 (s, 1H), 10.64 (s, 1H), 8.00 (d, J = 2.2 Hz, 1H), 7.83 (dd, J = 8.8, 2.3 Hz, 1H), 7.30 (tdd, J = 6.9, 5.9, 3.4 Hz, 5H), 6.99 (d, J = 8.8 Hz, 1H), 6.82 (d, J = 1.8 Hz, 1H), 6.43 (dd, J = 7.2, 2.0 Hz, 1H) ppm |

Example 16

Assays for Detecting and Measuring $Na_V$ Inhibition Properties of Compounds

E-VIPR Optical Membrane Potential Assay Method with Electrical Stimulation

Sodium channels are voltage-dependent proteins that can be activated by inducing membrane voltage changes by applying electric fields. The electrical stimulation instrument and methods of use are described in Ion Channel Assay Methods PCT/US01/21652, herein incorporated by reference and are referred to as E-VIPR. The instrument comprises a microtiter plate handler, an optical system for exciting the coumarin dye while simultaneously recording the coumarin and oxonol emissions, a waveform generator, a current- or voltage-controlled amplifier, and a device for inserting electrodes in well. Under integrated computer control, this instrument passes user-programmed electrical stimulus protocols to cells within the wells of the microtiter plate. The E-VIPR assay is conducted according to the following procedure (including reagents and solutions, assay protocol, and data analysis). For simplicity, the procedure is described in the past tense, but it will be understood that this procedure applies to such assays conducted in the past (if any) and to such assays conducted in the future (if any).

24 hours before the assay on E-VIPR, HEK cells expressing human NaV1.8 were seeded in 384-well poly-lysine coated plates at 15,000-20,000 cells per well. HEK cells were grown in media (exact composition is specific to each cell type and NaV subtype) supplemented with 10% FBS (Fetal Bovine Serum, qualified; GibcoBRL #16140-071) and 1% Pen-Strep (Penicillin-Streptomycin; GibcoBRL #15140-122). Cells were grown in vented cap flasks, in 90% humidity and 5% $CO_2$.

Reagents and Solutions 100 mg/mL Pluronic F-127 (Sigma #P2443), in dry DMSO

Compound Plates: 384-well round bottom plate, e.g. Corning 384-well Polypropylene Round Bottom #3656

Cell Plates: 384-well tissue culture treated plate, e.g. Greiner #781091-1B 10 mM DiSBAC$_6$(3) (Aurora #00-100-010) in dry DMSO
10 mM CC2-DMPE (Aurora #00-100-008) in dry DMSO
200 mM ABSC1 in $H_2O$ Bath1 buffer: Glucose 10 mM (1.8 g/L), Magnesium Chloride (Anhydrous), 1 mM (0.095 g/L), Calcium Chloride, 2 mM (0.222 g/L), HEPES 10 mM (2.38 g/L), Potassium Chloride, 4.5 mM (0.335 g/L), Sodium Chloride 160 mM (9.35 g/L).

Hexyl Dye Solution: Bath1 Buffer+0.5% β-cyclodextrin (made this prior to use, Sigma #C4767), 8 μM CC2-DMPE+ 2.5 μM DiSBAC$_6$(3). To make the solution added volume of 10% Pluronic F127 stock equal to volumes of CC2-DMPE+ DiSBAC$_6$(3). The order of preparation was first mixing Pluronic and CC2-DMPE, then adding DiSBAC$_6$(3) while vortexing, then adding Bath1+β-Cyclodextrin.

Assay Protocol

1) Pre-spotted compounds (in neat DMSO) into compound plates. Vehicle control (neat DMSO), the positive control (20 mM DMSO stock tetracaine, 125 μM final in assay) and test compounds were added to each well at 160× desired final concentration in neat DMSO. Final compound plate volume was 80 μL (80-fold intermediate dilution from 1 μL DMSO spot; 160-fold final dilution after transfer to cell plate). Final DMSO concentration for all wells in assay was 0.625%.

2) Prepared Hexyl Dye Solution.

3) Prepared cell plates. On the day of the assay, medium was aspirated and cells were washed three times with 100 μL of Bath1 Solution, maintaining 25 μL residual volume in each well.

4) Dispensed 25 μL per well of Hexyl Dye Solution into cell plates. Incubated for 20-35 minutes at room temp or ambient conditions.

5) Dispensed 80 μL per well of Bath1 into compound plates. Acid Yellow-17 (1 mM) was added and Potassium Chloride was altered from 4.5 to 20 mM depending on the NaV subtype and assay sensitivity.

6) Washed cell plates three times with 100 μL per well of Bath1, leaving 25 μL of residual volume. Then transferred 25 μL per well from Compound Plates to Cell Plates. Incubated for 20-35 minutes at room temp/ambient condition.

7) Read Plate on E-VIPR. Used the current-controlled amplifier to deliver stimulation wave pulses for 10 seconds and a scan rate of 200 Hz. A pre-stimulus recording was performed for 0.5 seconds to obtain the un-stimulated intensities baseline. The stimulatory waveform was followed by 0.5 seconds of post-stimulation recording to examine the relaxation to the resting state.

Data Analysis

Data was analyzed and reported as normalized ratios of emission intensities measured in the 460 nm and 580 nm channels. The response as a function of time was reported as the ratios obtained using the following formula:

$$R(t) = \frac{(intensity_{460\,nm} - background_{460\,nm})}{(intensity_{580\,nm} - background_{580\,nm})}$$

The data was further reduced by calculating the initial ($R_i$) and final ($R_f$) ratios. These were the average ratio values during part or all of the pre-stimulation period, and during sample points during the stimulation period. The response to the stimulus $R\square\square = R_f/R_i$ was then calculated and reported as a function of time.

Control responses were obtained by performing assays in the presence of a compound with the desired properties (positive control), such as tetracaine, and in the absence of pharmacological agents (negative control). Responses to the negative (N) and positive (P) controls were calculated as above. The compound antagonist activity A is defined as:

$$A = \frac{R - P}{N - P} * 100.$$

where R is the ratio response of the test compound

Example 17

Electrophysiology Assays for $Na_V$ Activity and Inhibition of Test Compounds

Patch clamp electrophysiology was used to assess the efficacy and selectivity of sodium channel blockers in dorsal root ganglion neurons. Rat neurons were isolated from the dorsal root ganglions and maintained in culture for 2 to 10 days in the presence of NGF (50 ng/ml) (culture media consisted of NeurobasalA supplemented with B27, glutamine and antibiotics). Small diameter neurons (nociceptors, 8-12 µm in diameter) were visually identified and probed with fine tip glass electrodes connected to an amplifier (Axon Instruments). The "voltage clamp" mode was used to assess the compound's $IC_{50}$ holding the cells at −60 mV. In addition, the "current clamp" mode was employed to test the efficacy of the compounds in blocking action potential generation in response to current injections. The results of these experiments contributed to the definition of the efficacy profile of the compounds.

Selected compounds and intermediates of the present invention herein are active against $Na_V1.8$ sodium channels as measured using the assays described herein and as presented in Table 4 below.

TABLE 4

| Cmpd. No | $Na_V1.8$ $IC_{50}$ (µM) |
|---|---|
| 1 | 0.004 |
| 1a | 0.001 |
| 2 | 0.028 |
| 2a | 0.003 |
| 3a | 0.006 |
| 4a | 0.011 |
| 5a | 0.011 |
| 6a | 0.012 |
| 7a | 0.013 |
| 8a | 0.013 |
| 9 | 0.33 |
| 9a | 0.014 |
| 10 | 0.086 |
| 10a | 0.017 |
| 11a | 0.028 |
| 12a | 0.03 |
| 13 | 0.329 |
| 13a | 0.03 |
| 14a | 0.037 |
| 15a | 0.044 |
| 16a | 0.05 |
| 17a | 0.051 |
| 18 | 0.457 |
| 18a | 0.054 |

Example 18

IonWorks Assays.

This assay is performed to determine the activity for the compounds of the present invention against non $Na_V1.8$ channels. This assay is conducted according to the following procedure. For simplicity, the procedure is described in the past tense, but it will be understood that this procedure applies to such assays conducted in the past (if any) and to such assays conducted in the future (if any). Sodium currents were recorded using the automated patch clamp system, IonWorks (Molecular Devices Corporation, Inc.). Cells expressing $Na_V$ subtypes were harvested from tissue culture and placed in suspension at 0.5-4 million cells per mL Bath1. The IonWorks instrument measured changes in sodium currents in response to applied voltage clamp similarly to the traditional patch clamp assay, except in a 384-well format. Using the IonWorks, dose-response relationships were determined in voltage clamp mode by depolarizing the cell from the experiment specific holding potential to a test potential of about 0 mV before and following addition of the test compound. The influence of the compound on currents were measured at the test potential.

Example 19

Aqueous Solubility Study

The aqueous solubility of compound 9 and 9a were determined according to the following procedure. Solubility data was determined at ambient conditions by equilibrating the compound with water on a shaking bed for 24 hours, followed by centrifugation and separation of the saturated solutions. The pH value of each media was measured before centrifugation, and the saturated solutions were assayed by HPLC. The aqueous solubility of compound 9a in water was low (<0.001 mg/ml at pH 6.0) whereas the aqueous solubility of compound 9 in water was approximately 0.3 mg/ml.

TABLE 5

Aqueous Solubility of Compounds 9 and 9a:

| Compound | Solid form | pH | Solubility (mg/mL) |
|---|---|---|---|
| 9a | crystalline | 6.0 | <0.001 |
| 9a | crystalline | 1.2 | <0.001 |
| 9 | crystalline | 1 | 0.002 |
| 9 | crystalline | 3 | 0.11 |
| 9 | crystalline | 3.3 | 0.24 |
| 9 | crystalline | 5 | 0.42 |
| 9 | crystalline | 7 | 0.50 |
| 9 | crystalline | 8 | 2.24 |

Example 20

Pharmacokinetic Studies

The pharmacokinetic parameters of selected compounds of this invention were determined in the experiments described below. General analytic procedures and specific experimental protocols were employed as follows:

General Analytic Procedures

The following general analytic procedures were employed in the pharmacokinetic experiments described below:

Sample Analysis.

Concentrations of compound 9 and compound 9a in plasma were determined using a high performance liquid chromatography/tandem mass spectrometry (HPLC/MS/MS) method. Before extraction, plasma samples were diluted using blank plasma at an appropriate dilution factor, as necessary, depending on the dose level. Compound 9a and compound 9 along with the internal standard (IS) were extracted from (diluted) plasma, 20 µL each, by direct protein precipitation with acetonitrile (1:25 ratio of plasma/acetonitrile). After centrifugation, the supernatant extract (10 µL) was injected onto the LC/MS/MS system. The HPLC system included a Phenomenex Synergy Kinetix C8 column, 2.6 micron, 2.0 mm diameter×75 mm long eluted with a gradient mobile phase consisting of 0.1% formic acid in water or in acetonitrile.

The analytes were detected by MS/MS with Electrospray Ionization (ESI) in the mode of multiple reaction monitoring (MRM). The lower limit of quantitation (LLOQ) was 1 to 10 ng/mL for compound 9a and 2.5 to 25 ng/mL for compound 9. The linear range of the assay was from 1 or 10 to 10000 ng/mL for compound 9a and 2.5 or 25 to 10000 ng/mL for compound 9. The intra-day and inter-day assay accuracy was within 20% of the nominal values. The intra- and inter-day assay variability was ≤20%.

Pharmacokinetic Data Analysis.

Plasma concentration-time profiles of compound 9a and compound 9 were analyzed by noncompartmental pharmacokinetic methods using Watson LIMS version 7.4 SP3 (Thermo Fisher Scientific, Inc., Philadelphia, Pa.)

Key pharmacokinetic parameters such as $AUC_{all}$, $AUC_{extra}$, $C_{max}$, $t_{max}$, Cl, Vss and $t_{1/2}$ were determined.

Statistical Data Analysis.

Descriptive statistical data of pharmacokinetic parameters were calculated, including the mean, standard deviation (SD), using Watson LIMS version 7.4 SP3 or Microsoft Excel 2000.

Monkey Oral Study

Male or female cynomolgus monkeys (n=3 per dose group) were administered single nominal PO doses of 10, 40, 100, 300, 500, 750 and 1000 mg/kg of compound 9 by gavage. Compound 9 was formulated in 30% PEG400 and 10% TPGS in water or 5% TPGS, 5% PVP-K30 in 50 mM Citrate, pH 5. Animals were fasted overnight prior to dosing, and were fed two hours post dose. Water was available before and after dosing.

Blood samples (approximately 0.25 mL each) were collected via a carotid artery catheter prior to dosing and at 0.25, 0.5, 1, 2, 4, 8, 12, 24, 48 and 72 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of compound 9a and compound 9 with a lower limit of quantitation (LLOQ) of 1.00 to 10.0 ng/mL for compound 9a, and 10.0 to 25.0 ng/mL for compound 9. Plasma concentration vs. time data of compound 9a was subjected to noncompartmental pharmacokinetic (PK) analysis. The results of this analysis are provided in Table 7. For compound 9, plasma concentrations were below LLOQ for the majority of the samples, and no PK analysis could be performed.

TABLE 7

Pharmacokinetic Data from Monkey Oral Study

| Nominal Dose (mg/kg) | Formulation | Analyte | $AUC_{extra}$ (µg · hr/mL) | $C_{max}$ (µg/mL) | $T_{max}$ (hr) | $T_{1/2}$ (hr) |
|---|---|---|---|---|---|---|
| 10 | 30% PEG400/10% TPGS/60% water | Cmpd 9a | 21.5 ± 13.7 | 1.13 ± 0.187 | 4.67 ± 3.06 | 8.57 ± 2.75 |
| 40 | 5% TPGS/5% PVP-K30/50 mMCitrate pH5 | Cmpd 9a | 62.4 ± 23.8 | 4.50 ± 0.51 | 3.33 ± 1.15 | 9.58 ± 3.91 |
| 100 | 5% TPGS/5% PVP-K30/50 mMCitrate pH5 | Cmpd 9a | 49.6 ± 10.7 | 3.34 ± 0.34 | 4.00 ± 0.00 | 7.04 ± 0.36 |
| 300 | 5% TPGS/5% PVP-K30/50 mMCitrate pH5 | Cmpd 9a | 93.4 ± 22.7 | 5.77 ± 1.46 | 2.67 ± 1.15 | 11.6 ± 2.3 |
| 500 | 5% TPGS/5% PVP-K30/50 mMCitrate pH5 | Cmpd 9a | 124 ± 6.0 | 5.76 ± 1.69 | 6.00 ± 3.46 | 9.80 ± 1.08 |
| 750 | 5% TPGS/5% PVP-K30/50 mMCitrate pH5 | Cmpd 9a | 138 ± 47.3 | 7.49 ± 3.13 | 6.67 ± 4.62 | 13.1 ± 3.1 |
| 1000 | 5% TPGS/5% PVP-K30/50 mMCitrate pH5 | Cmpd 9a | 176 ± 20.7 | 7.88 ± 0.80 | 4.00 ± 0.00 | 13.5 ± 3.1 |

N = 3 monkeys per dose level,
Mean ± Standard deviation

Rat Oral Study

Groups of male and female Sprague Dawley rats (n=3 per dose group) were administered single nominal oral doses of 10, 100, 400, 640, 1000 mg/kg (for males) and 30, 100, 300, 640, 1000 mg/kg (for females) of compound 9 by gavage. Compound 9 was formulated in either 30% PEG400 and 10% TPGS in water or 5% TPGS, 5% PVP-K30 in 50 mM Citrate, pH 5. Animals had free access to food and water before and after dosing. Blood samples (approximately 0.25 mL each) were collected via a carotid artery catheter prior to dosing and at 0.25, 0.5, 1, 2, 4, 8, 12, 24, 48 and 72 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of compound 9a and compound 9 with a lower limit of quantitation (LLOQ) of 1 to 25 ng/mL for compound 9a and 2.5 to 25 ng/mL for compound 9. Plasma concentration vs. time data of compound 9a was subjected to noncompartmental pharmacokinetic (PK) analysis. The results of this analysis are provided in Table 8. For compound 9, plasma concentrations were below LLOQ for the majority of the samples, and no PK analysis could be performed.

a jugular vein cannula. Compound 9 was formulated in DMI vehicle, consisting of 35% PEG400, 15% ethanol, 10% dimethyl isosorbide and 40% of (5% dextran in water). Animals had free access to food and water before and after dosing. Blood samples (approximately 0.25 mL each) were collected via a carotid artery catheter prior to dosing and at 5 min, 10 min, 0.25, 0.5, 1, 2, 4, 8, 12, 24 hours post dose. Each blood sample was collected into a tube that was kept on wet ice and contained potassium EDTA as the anticoagulant. Plasma was separated and stored at approximately −70° C. until analysis.

Plasma samples were analyzed using a liquid chromatography/tandem mass spectrometry (LC/MS/MS) method to determine the concentrations of compound 9a and compound 9 with a lower limit of quantitation (LLOQ) of 1 ng/mL for compound 9a and 2.5 ng/mL for compound 9. Plasma concentration vs. time data were subjected to noncompartmental pharmacokinetic (PK) analysis. The results of this analysis are provided in Table 9. For compound 9, plasma concentrations were below LLOQ for the majority of the samples, and no PK analysis could be performed.

TABLE 8

Pharmacokinetic Data from Rat Oral Study

| Gender | Nominal Dose (mg/kg) | Formulation | Analyte | $AUC_{extra}$ (µg·hr/mL) | $C_{max}$ (µg/mL) | $T_{max}$ (hr) | $T_{1/2}$ (hr) |
|---|---|---|---|---|---|---|---|
| Male | 10 | 5% TPGS/5% PVP-K30/50 mMCitrate pH5 | Cmpd 9a | 3.6 ± 0.24 | 0.29 ± 0.05 | 5.33 ± 2.31 | 3.80 ± 0.73 |
|  | 100 | 5% TPGS/5% PVP-K30/50 mMCitrate pH5 | Cmpd 9a | 24.8 ± 4.6 | 1.67 ± 0.19 | 8.00 ± 0.00 | 5.36 ± 2.37 |
|  | 400 | 5% TPGS/5% PVP-K30/50 mMCitrate pH5 | Cmpd 9a | 68.6 ± 25.7 | 3.74 ± 1.25 | 5.67 ± 4.04 | 5.20 ± 1.96 |
|  | 640 | 5% TPGS/5% PVP-K30/50 mMCitrate pH5 | Cmpd 9a | 74.9 ± 24.1 | 4.76 ± 0.98 | 6.00 ± 3.46 | 6.91 ± 1.84 |
|  | 1000 | 5% TPGS/5% PVP-K30/50 mMCitrate pH5 | Cmpd 9a | 88.5 ± 41.0 | 4.54 ± 0.91 | 6.67 ± 2.31 | 7.95 ± 2.24 |
| Females | 30 | 5% TPGS/5% PVP-K30/50 mMCitrate pH5 | Cmpd 9a | 99.2 ± 6.88 | 3.33 ± 0.43 | 6.67 ± 2.31 | 10.8 ± 1.60 |
|  | 100 | 5% TPGS/5% PVP-K30/50 mMCitrate pH5 | Cmpd 9a | 187 ± 17.5 | 5.82 ± 0.58 | 12.0 ± 0.00 | 9.15 ± 0.44 |
|  | 300 | 5% TPGS/5% PVP-K30/50 mMCitrate pH5 | Cmpd 9a | 282 ± 74.2 | 7.90 ± 1.30 | 10.7 ± 2.31 | 13.1 ± 2.65 |
|  | 640 | 5% TPGS/5% PVP-K30/50 mMCitrate pH5 | Cmpd 9a | 324 ± 32.8 | 10.0 ± 1.45 | 9.33 ± 2.31 | 7.51 ± 1.86 |
|  | 1000 | 5% TPGS/5% PVP-K30/50 mMCitrate pH5 | Cmpd 9a | 345 ± 69.6 | 10.6 ± 3.58 | 13.3 ± 9.24 | 7.90 ± 3.37 |

N = 3 rats per dose level,
Mean ± Standard deviation

Rat IV Study

Male Sprague Dawley rats (n=3) were administered a single nominal IV bolus dose of 1 mg/kg of compound 9 via

TABLE 9

Pharmacokinetic Data from Rat IV Study

| Dose (mg/kg) | Formulation | Analyte | C0 (µg/ml) | $AUC_{all}$ (µg * hr/ml) | $AUC_{extra}$ (µg * hr/ml) | t½ (hr) | Cl (ml/min/kg) | Vss (L/kg) |
|---|---|---|---|---|---|---|---|---|
| 1 | DMI | Cmpd 9a | 0.259 | 0.592 | 0.611 | 2.43 | 18.7 | 3.77 |

The studies described above, demonstrate that compound 9 is converted in vivo into compound 9a in at least rats and monkeys.

Many modifications and variations of the embodiments described herein may be made without departing from the scope, as is apparent to those skilled in the art. The specific embodiments described herein are offered by way of example only.

We claim:

1. A compound selected from the group consisting of:

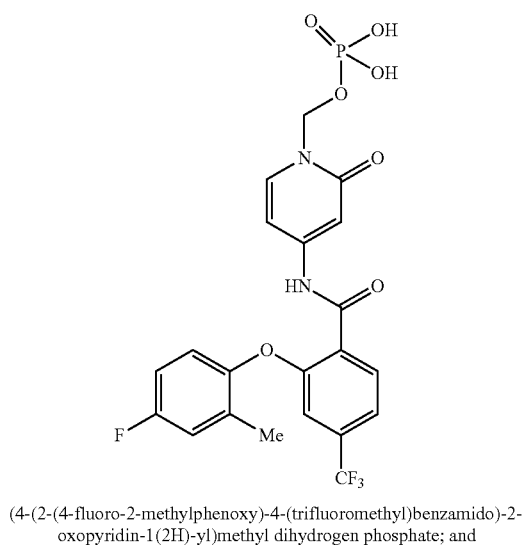 [SMILES: Cc1cc(F)ccc1Oc1cc(C(F)(F)F)ccc1C(=O)Nc1ccn(COP(=O)(O)O)c(=O)c1]

(4-(2-(4-fluoro-2-methylphenoxy)-4-(trifluoromethyl)benzamido)-2-oxopyridin-1(2H)-yl)methyl dihydrogen phosphate; and

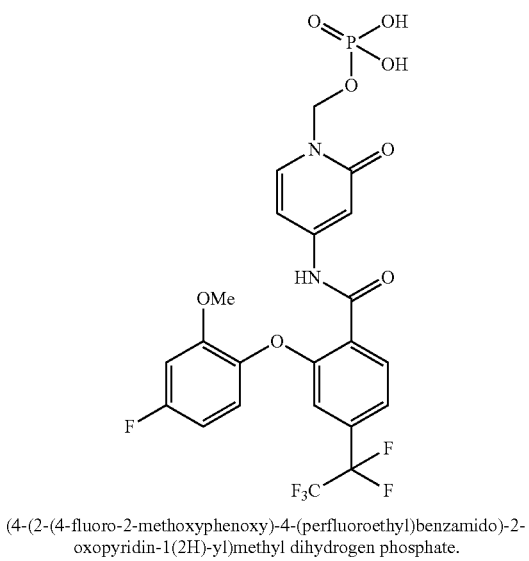

(4-(2-(4-fluoro-2-methoxyphenoxy)-4-(perfluoroethyl)benzamido)-2-oxopyridin-1(2H)-yl)methyl dihydrogen phosphate.

2. A method of inhibiting a voltage-gated sodium channel in a subject comprising administering to the subject a compound according to claim 1.

3. The method of claim 2, wherein the voltage-gated sodium channel is $Na_V1.8$.

4. The method of claim 2, wherein the compound is:

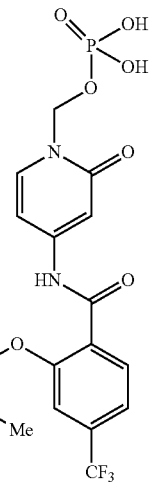

(4-(2-(4-fluoro-2-methylphenoxy)-4-(trifluoromethyl)benzamido)-2-oxopyridin-1(2H)-yl)methyl dihydrogen phosphate.

5. The method of claim 4, wherein the voltage-gated sodium channel is $Na_V1.8$.

6. The method of claim 2, wherein the compound is:

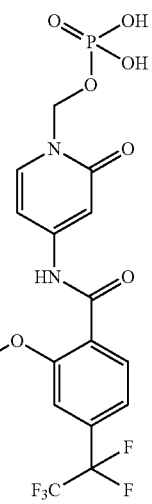

(4-(2-(4-fluoro-2-methoxyphenoxy)-4-(perfluoroethyl)benzamido)-2-oxopyridin-1(2H)-yl)methyl dihydrogen phosphate.

7. The method of claim 6, wherein the voltage-gated sodium channel is $Na_V1.8$.

8. A method of treating or lessening the severity in a subject of chronic pain, gut pain, neuropathic pain, musculoskeletal pain, acute pain, inflammatory pain, cancer pain, idiopathic pain, postsurgical pain, visceral pain, multiple sclerosis, Charcot-Marie-Tooth syndrome, incontinence, pathological cough, or cardiac arrhythmia comprising administering to the subject an effective amount of a compound according to claim 1.

9. The method of claim 8, wherein the compound is:

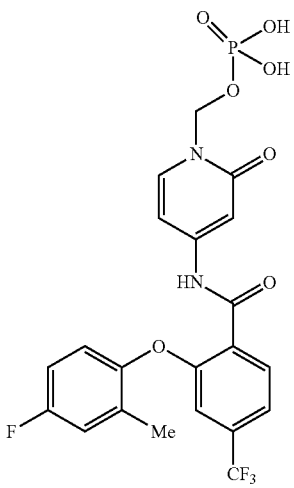

(4-(2-(4-fluoro-2-methylphenoxy)-4-(trifluoromethyl)benzamido)-2-oxopyridin-1(2H)-yl)methyl dihydrogen phosphate.

10. The method of claim 9, wherein the method comprises treating or lessening the severity in a subject of gut pain, wherein gut pain comprises inflammatory bowel disease pain, Crohn's disease pain or interstitial cystitis pain.

11. The method of claim 9, wherein the method comprises treating or lessening the severity in a subject of neuropathic pain.

12. The method of claim 11, wherein neuropathic pain comprises trigeminal neuralgia.

13. The method of claim 11, wherein neuropathic pain comprises idiopathic small-fiber neuropathy.

14. The method of claim 11, wherein neuropathic pain comprises postherpetic neuralgia.

15. The method of claim 9, wherein the method comprises treating or lessening the severity in a subject of musculoskeletal pain.

16. The method of claim 15, wherein musculoskeletal pain comprises osteoarthritis pain.

17. The method of claim 9, wherein the method comprises treating or lessening the severity in a subject of inflammatory pain, wherein inflammatory pain comprises rheumatoid arthritis pain.

18. The method of claim 9, wherein the method comprises treating or lessening the severity in a subject of idiopathic pain, wherein idiopathic pain comprises fibromyalgia pain.

19. The method of claim 9, wherein the method comprises treating or lessening the severity in a subject of acute pain.

20. The method of claim 19, wherein acute pain comprises acute post-operative pain.

21. The method of claim 9, wherein the method comprises treating or lessening the severity in a subject of postsurgical pain.

22. The method of claim 9, wherein the method comprises treating or lessening the severity in a subject of visceral pain.

23. The method according to claim 9, wherein said subject is treated with one or more additional therapeutic agents administered concurrently with, prior to, or subsequent to treatment with the compound.

24. The method of claim 8, wherein the compound is:

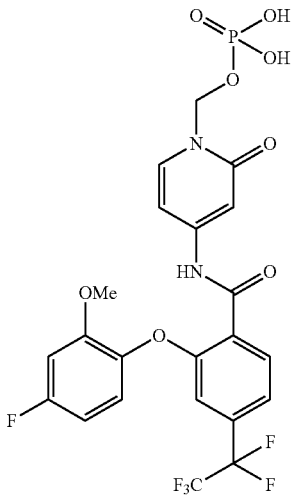

(4-(2-(4-fluoro-2-methoxyphenoxy)-4-(perfluoroethyl)benzamido)-2-oxopyridin-1(2H)-yl)methyl dihydrogen phosphate.

25. The method of claim 24, wherein the method comprises treating or lessening the severity in a subject of gut pain, wherein gut pain comprises inflammatory bowel disease pain, Crohn's disease pain or interstitial cystitis pain.

26. The method of claim 24, wherein the method comprises treating or lessening the severity in a subject of neuropathic pain.

27. The method of claim 26, wherein neuropathic pain comprises trigeminal neuralgia.

28. The method of claim 26, wherein neuropathic pain comprises idiopathic small-fiber neuropathy.

29. The method of claim 26, wherein neuropathic pain comprises postherpetic neuralgia.

30. The method of claim 24, wherein the method comprises treating or lessening the severity in a subject of musculoskeletal pain.

31. The method of claim 30, wherein musculoskeletal pain comprises osteoarthritis pain.

32. The method of claim 24, wherein the method comprises treating or lessening the severity in a subject of inflammatory pain, wherein inflammatory pain comprises rheumatoid arthritis pain.

33. The method of claim 24, wherein the method comprises treating or lessening the severity in a subject of idiopathic pain, wherein idiopathic pain comprises fibromyalgia pain.

34. The method of claim 24, wherein the method comprises treating or lessening the severity in a subject of acute pain.

35. The method of claim 34, wherein acute pain comprises acute post-operative pain.

36. The method of claim 24, wherein the method comprises treating or lessening the severity in a subject of postsurgical pain.

37. The method of claim 24, wherein the method comprises treating or lessening the severity in a subject of visceral pain.

38. The method according to claim 24, wherein said subject is treated with one or more additional therapeutic agents administered concurrently with, prior to, or subsequent to treatment with the compound.

* * * * *